US010512667B2

(12) United States Patent
Kerppola et al.

(10) Patent No.: US 10,512,667 B2
(45) Date of Patent: Dec. 24, 2019

(54) COMPOSITIONS AND METHODS FOR TREATING CONDITIONS RELATED TO ADRENOCORTICAL ACTIVITY AND/OR EXCESSIVE STEROID PRODUCTION

(71) Applicant: The Regents of the University of Michigan, Ann Arbor, MI (US)

(72) Inventors: Tom K. Kerppola, Ann Arbor, MI (US); Veronica E. Burns, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/020,457

(22) Filed: Jun. 27, 2018

(65) Prior Publication Data

US 2018/0369321 A1 Dec. 27, 2018

Related U.S. Application Data

(60) Provisional application No. 62/525,529, filed on Jun. 27, 2017.

(51) Int. Cl.
| | |
|---|---|
| *A61K 38/12* | (2006.01) |
| *A61P 5/46* | (2006.01) |
| *A61P 5/42* | (2006.01) |
| *A61K 45/06* | (2006.01) |
| *A61P 35/00* | (2006.01) |
| *A61K 38/13* | (2006.01) |
| *A61K 31/17* | (2006.01) |
| *A61K 31/277* | (2006.01) |
| *A61K 31/352* | (2006.01) |
| *A61K 31/496* | (2006.01) |
| *A61K 31/4965* | (2006.01) |
| *A61K 31/5685* | (2006.01) |
| *A61K 31/64* | (2006.01) |
| *A61K 31/4725* | (2006.01) |
| *A61K 31/18* | (2006.01) |
| *A61K 35/04* | (2006.01) |

(52) U.S. Cl.
CPC .............. *A61K 38/12* (2013.01); *A61K 31/17* (2013.01); *A61K 31/277* (2013.01); *A61K 31/352* (2013.01); *A61K 31/4725* (2013.01); *A61K 31/496* (2013.01); *A61K 31/4965* (2013.01); *A61K 31/5685* (2013.01); *A61K 31/64* (2013.01); *A61K 38/13* (2013.01); *A61K 45/06* (2013.01); *A61P 5/42* (2018.01); *A61P 5/46* (2018.01); *A61P 35/00* (2018.01); *A61K 31/18* (2013.01); *A61K 35/04* (2013.01); *A61K 2300/00* (2013.01)

(58) Field of Classification Search
CPC ... A61K 38/12; A61P 5/42; A61P 5/46; A61P 35/00; A61P 35/04

USPC ............................................................ 514/635
See application file for complete search history.

(56) References Cited

FOREIGN PATENT DOCUMENTS

WO WO-9008541 A1 * 8/1990 ........... A61K 31/185

OTHER PUBLICATIONS

Chen et al., "Detection of in Vivo P-Glycoprotein Inhibition by PSC 833 Using Tc-99m Sestamibi", Clinical Cancer Research, vol. 3, No. 4, pp. 545-552 (1997).*
Nilubol et al., "Four clinically utilized drugs were identified and validated for treatment of adrenocortical cancer using quantitative high-throughput screening", Journal of Translation Medicine, vol. 10, No. 198, pp. 1-15 (2012).*
Altuvia, S, et al., Targeted disruption of the mouse mdr1b gene reveals that steroid hormones enhance mdr gene expression. J Biol Chem 1993;268(36):27127-32.
An, S, et al., Inhibition of acyl-coenzyme A:cholesterol acyltransferase stimulates cholesterol efflux from macrophages and stimulates farnesoid X receptor in hepatocytes. Exp Mol Med 2008;40(4):407-17.
Assie, G, et al., Integrated genomic characterization of adrenocortical carcinoma. Nat Genet 2014;46(6):607-12.
Bose, HS, et al., Rapid regulation of steroidogenesis by mitochondrial protein import. Nature 2002;417(6884):87-91.
Brecher, PI, et al., Effect of 4-am inopyrazolopyrim idine and aminoglutethimide on cholesteryl metabolism and steroidogenesis in the rat adrenal. Endocrinology 1978;102(5):1404-13.
Cheng, Y, et al., ATR-101 disrupts mitochondrial functions in adrenocortical carcinoma cells and in vivo. Endocrine-Related Cancer 2016;23(4):1-19.
Christiansen-Weber, TA, et al., Functional loss of ABCA1 in mice causes severe placental malformation, aberrant lipid distribution, and kidney glomerulonephritis as well as high-density lipoprotein cholesterol deficiency. Am J Pathol 2000;157(3):1017-29.

(Continued)

*Primary Examiner* — Kevin E Weddington
(74) *Attorney, Agent, or Firm* — Casimir Jones, SC; Robert Goetz

(57) ABSTRACT

Provided herein are methods for treating subjects having conditions related to adrenocortical activity and/or excessive steroid production. In particular, provided herein are methods for treating subjects having conditions related to adrenocortical activity and/or excessive steroid production through administration of at least one of the following agents: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity.

3 Claims, 26 Drawing Sheets
Specification includes a Sequence Listing.

(56) References Cited

OTHER PUBLICATIONS

Creemers, SG, et al., Future directions in the diagnosis and medical treatment of adrenocortical carcinoma. Endocr Relat Cancer 2016;23(1):R43-69.
Debry, P, et al., Role of multidrug resistance P-glycoproteins in cholesterol esterification. J Biol Chem 1997;272(2):1026-31.
Dibartolomeis, MJ, et al., Inhibition of ACTH action on cultured bovine adrenal cortical cells by 2,3,7,8-tetrachlorodibenzo-p-dioxin through a redistribution of cholesterol. J Biol Chem 1986;261(10):4432-7.
Dominick, et al., Subacute toxicity of a novel inhibitor of acyl-CoA: cholesterol acyltransferase in beagle dogs. Fundam Appl Toxicol. Feb. 1993;20(2):217-24.
Fallahsharoudi, A, et al., Domestication Effects on Stress Induced Steroid Secretion and Adrenal Gene Expression in Chickens. Sci Rep 2015;5:15345.
Goldstein, JL, et al., The LDL receptor. Arterioscler Thromb Vasc Biol 2009;29(4):431-8.
Ikonen, E. Cellular cholesterol trafficking and compartmentalization. Nat Rev Mol Cell Biol 2008;9(2):125-38.
Junquero, D, et al., Lack of toxic effects of F 12511, a novel potent inhibitor of acyl-coenzyme A: cholesterol O-acyltransferase, on human adrenocortical cells in culture. Biochem Pharmacol 2001;61(4):387-98.
Lapensee, CR, et al., ATR-101, a Selective and Potent Inhibitor of Acyl-CoA Acyltransferase 1, Induces Apoptosis in H295R Adrenocortical Cells and in the Adrenal Cortex of Dogs. Endocrinology 2016;157(5):1775-88.
Le Goff W, et al., Reevaluation of the role of the multidrug-resistant P-glycoprotein in cellular cholesterol homeostasis. J Lipid Res 2006;47(1):51-8.
Le Goff, et al., Cyclosporin A traps ABCA1 at the plasma membrane and inhibits ABCA1-mediated lipid efflux to apolipoprotein A-I. Arterioscler Thromb Vasc Biol. Nov. 2004;24(11):2155-61.
Lehoux, JG, et al., Short-term effects of ACTH on the low-density lipoprotein receptor mRNA level in rat and hamster adrenals. J Mol Endocrinol 1991;6(3):223-30.
Luker, GD, et al., Multidrug resistance (MDR1) P-glycoprotein enhances esterification of plasma membrane cholesterol. J Biol Chem 1999;274(11):6979-91.
Maiter, D, et al., Efficacy and safety of mitotane in the treatment of adrenocortical carcinoma: A retrospective study in 34 Belgian patients. Ann Endocrinol (Paris) 2016;77(5):578-85.
Matsuo, M, et al., Difference between normal and WHHL rabbits in susceptibility to the adrenal toxicity of an acyl-CoA:cholesterol acyltransferase inhibitor, FR145237. Toxicol Appl Pharmacol 1996;140(2):387-92.
McNeish, J, et al., High density lipoprotein deficiency and foam cell accumulation in mice with targeted disruption of ATP-binding cassette transporter-1. Proc Natl Acad Sci U S A 2000;97(8):4245-50.
Meiner, VL, et al., Disruption of the acyl-CoA:cholesterol acyltransferase gene in mice: evidence suggesting multiple cholesterol esterification enzymes in mammals. Proc Natl Acad Sci U S A 1996;93(24):14041-6.
Meuwese, MC, et al., ACAT inhibition and progression of carotid atherosclerosis in patients with familial hypercholesterolemia: the CAPTIVATE randomized trial. JAMA 2009;301(11):1131-9.
Miller, WL, et al., Early steps in steroidogenesis: intracellular cholesterol trafficking. J Lipid Res 2011;52(12):2111-35.
Mitsche, MA, et al., Flux analysis of cholesterol biosynthesis in vivo reveals multiple tissue and cell-type specific pathways. Elife 2015;4:e07999.
Morita, SY, et al., Bile salt-dependent efflux of cellular phospholipids mediated by ATP binding cassette protein B4. Hepatology 2007;46(1):188-99.
Muller, MB, et al., ABCB1 (MDR1)-type P-glycoproteins at the blood-brain barrier modulate the activity of the hypothalamic-pituitary-adrenocortical system: implications for affective disorder. Neuropsychopharmacology 2003;28(11):1991-9.
Orso, E, Transport of lipids from golgi to plasma membrane is defective in tangier disease patients and Abc1-deficient mice. Nat Genet 2000;24(2):192-6.
Out, R, et al., Coexistence of foam cells and hypocholesterolemia in mice lacking the ABC transporters A1 and G1. Circ Res 2008;102(1):113-20.
Pandey, A, et al., Analysis of endocrine disruption effect of Roundup® in adrenal gland of male rats. Toxicology Reports 2015;2:1075-85.
Pokhrel, L, et al., Inhibition of Acyl-CoA: cholesterol acyltransferase (ACAT), overexpression of cholesterol transporter gene, and protection of amyloid β (Aβ) oligomers-induced neuronal cell death by tricyclic pyrone molecules. J Med Chem 2012;55(20):8969-73.
Porto, AF. Lysosomal acid lipase deficiency: diagnosis and treatment of Wolman and Cholesteryl Ester Storage Diseases. Pediatr Endocrinol Rev 2014;12 Suppl 1:125-32.
Reaven, E, et al., Expression of scavenger receptor class B type 1 (SR—BI) promotes microvillar channel formation and selective cholesteryl ester transport in a heterologous reconstituted system. Proc Natl Acad Sci U S A 2001;98(4):1613-8.
Reindel, JF, et al., Toxicologic effects of a novel acyl-CoA:cholesterol acyltransferase inhibitor in cynomolgus monkeys. Toxicol Pathol 1994;22(5):510-8.
Rodriguez, A, et al., Anti-atherogenic effects of the acyl-CoA:cholesterol acyltransferase inhibitor, avasimibe (CI-1011), in cultured primary human macrophages. Atherosclerosis 2002;161(1):45-54.
Sahakitrungruang, T. Clinical and molecular review of atypical congenital adrenal hyperplasia. Ann Pediatr Endocrinol Metab 2015;20(1):1-7.
Sbiera, S, et al., Mitotane Inhibits Sterol-O-Acyl Transferase 1 Triggering Lipid-Mediated Endoplasmic Reticulum Stress and Apoptosis • in Adrenocortical Carcinoma Cells. Endocrinology 2015;156(11):3895-908.
Sliskovic, DR, et al., ACAT inhibitors: the search for a novel and effective treatment of hypercholesterolemia and atherosclerosis. Prog Med Chem 2002;39:121-71.
Sliskovic, et al., alpha-Substituted malonester amides: tools to define the relationship between ACAT inhibition and adrenal toxicity. J Med Chem. Feb. 26, 1998;41(5):682-90.
Tanaka, et al., Inhibitors of acyl-CoA:cholesterol O-acyltransferase. 3. Discovery of a novel series of N-alkyl-N-[(fluorophenoxy)benzyl]-N'-arylureas with weak toxicological effects on adrenal glands. J Med Chem. Oct. 22, 1998;41(22):4408-20.
Tardif, JC, et al., Effects of the acyl coenzyme A:cholesterol acyltransferase inhibitor avasimibe on human atherosclerotic lesions. Circulation 2004;110(21):3372-7.
Tarling, EJ, et al., ATP binding cassette transporter G1 (ABCG1) is an intracellular sterol transporter. Proc Natl Acad Sci U S A 2011;108(49):19719-24.
Tessner, TG, et al., Overexpression of MDR1 in an intestinal cell line results in increased cholesterol uptake from micelles. Biochem Biophys Res Commun 2000;267(2):565-71.
Vanier, MT. Niemann-Pick disease type C. Orphanet J Rare Dis. Jun. 3, 2010;5:16. doi: 10.1186/1750-1172-5-16.
Wang, X, et al., Macrophage ABCA1 and ABCG1, but not SR—BI, promote macrophage reverse cholesterol transport in vivo. J Clin Invest 2007;117(8):2216-24.
Wolfgang, GH, et al., Biochemical alterations in guinea pig adrenal cortex following administration of PD 132301-2, an inhibitor of acyl-CoA:cholesterol acyltransferase. Life Sci 1995;56(13):1089-93.
Yamauchi, Y, et al., Deficiency in the Lipid Exporter ABCA1 Impairs Retrograde Sterol Movement and Disrupts Sterol Sensing at the Endoplasmic Reticulum. J Biol Chem 2015;290(39):23464-77.
Zheng, S. et al., Comprehensive Pan-Genomic Characterization of Adrenocortical Carcinoma. Cancer Cell 2016;29(5):723-36.

\* cited by examiner

FIG. 3A
FIG. 3B
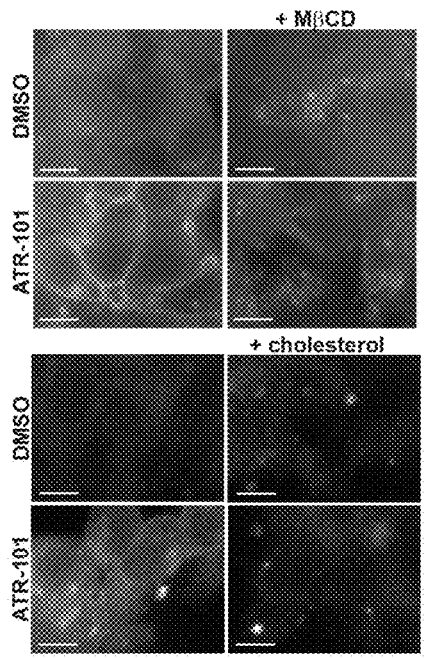
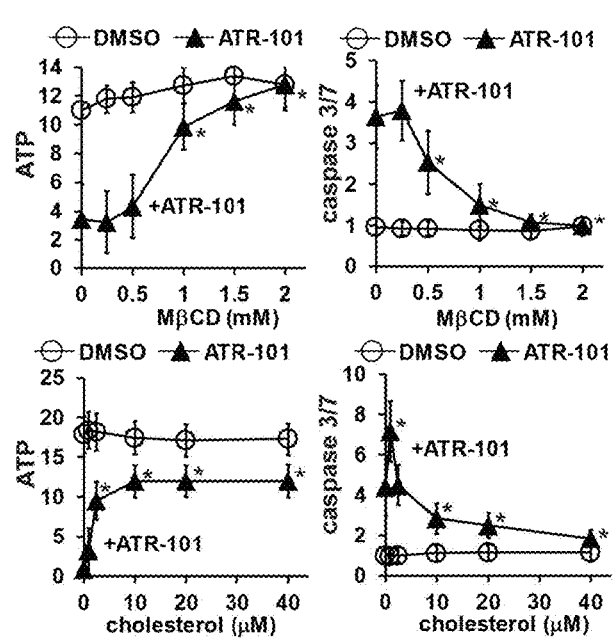
FIG. 3C
FIG. 3D
FIG. 3E
FIG. 3F
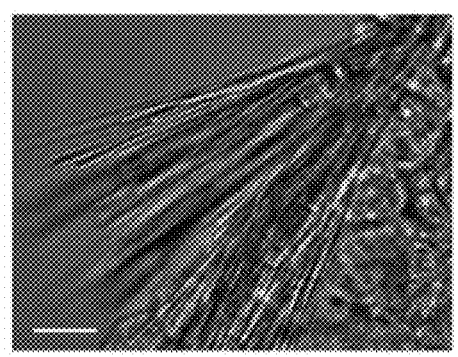
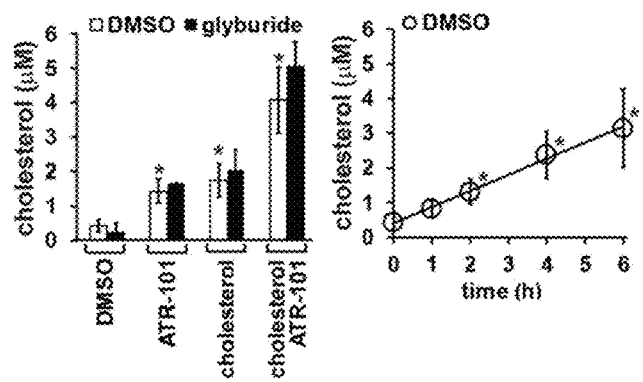

FIG. 8B
FIG. 8C
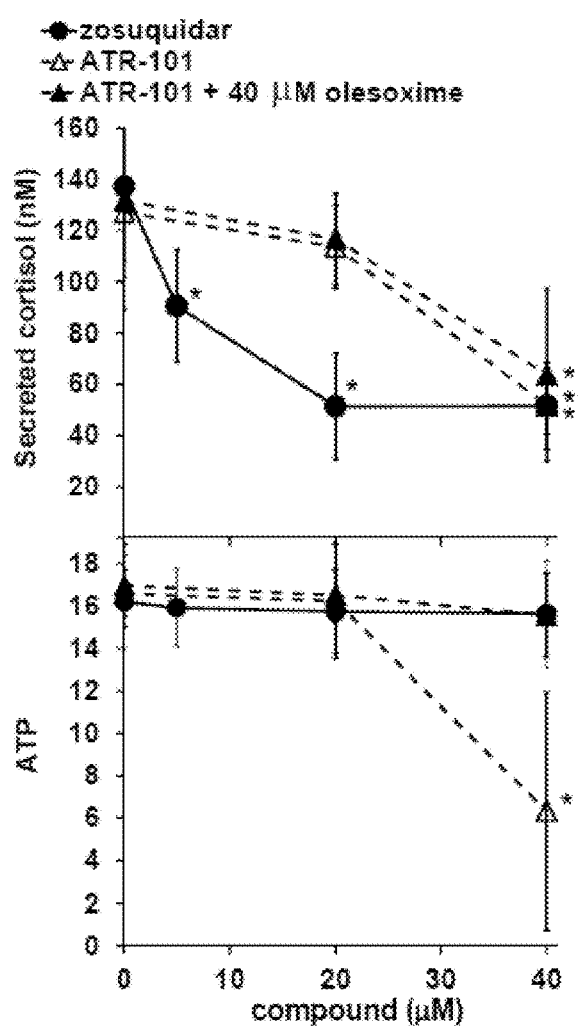
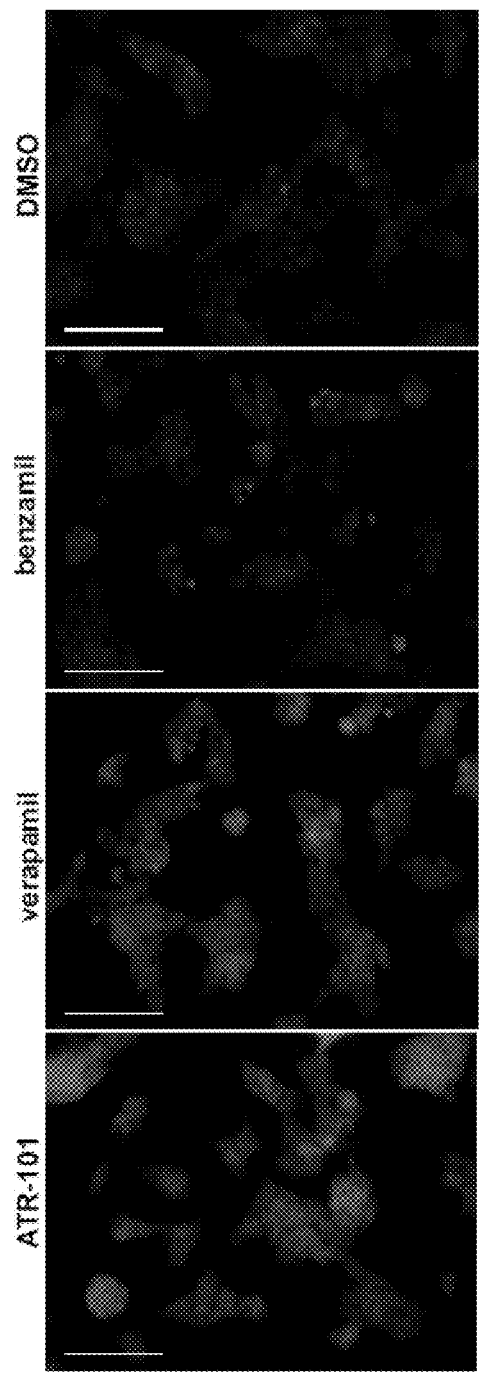

FIG. 12A
FIG. 12B
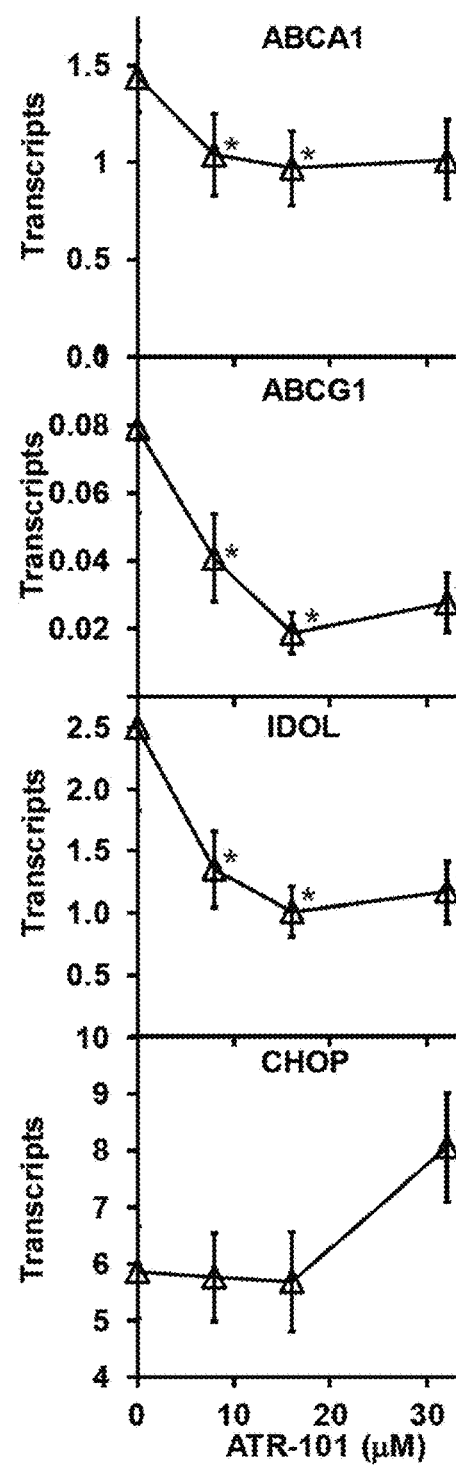
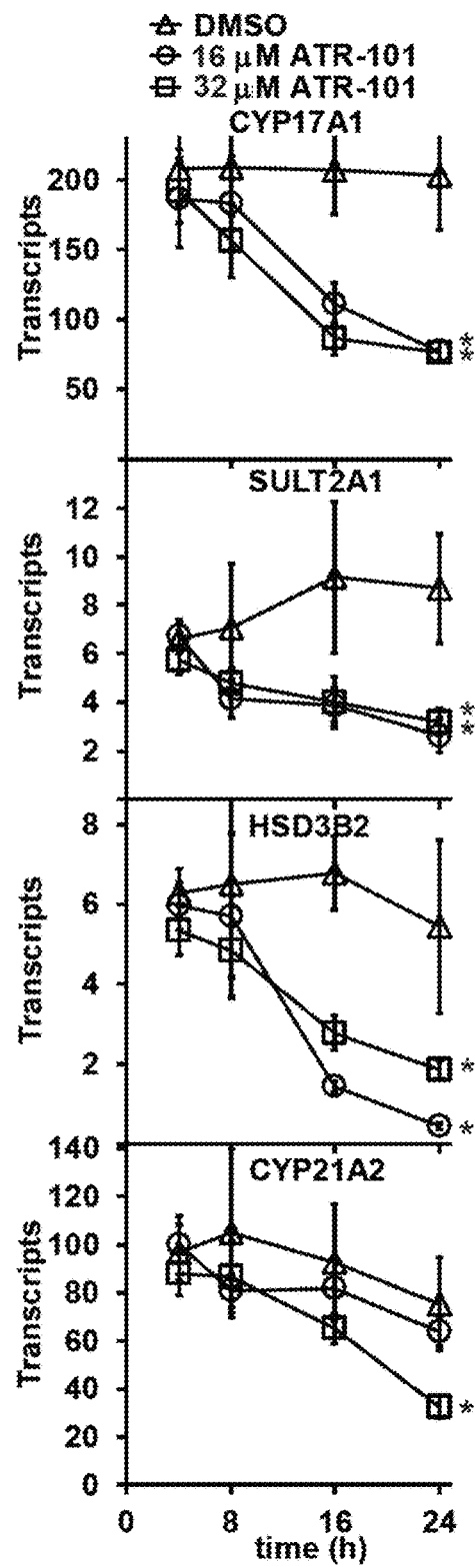

COMPOSITIONS AND METHODS FOR TREATING CONDITIONS RELATED TO ADRENOCORTICAL ACTIVITY AND/OR EXCESSIVE STEROID PRODUCTION

The present application claims priority to U.S. Provisional application Ser. No. 62/525,529, filed Jun. 27, 2017, which is herein incorporated by reference in its entirety.

STATEMENT REGARDING FEDERALLY SPONSORED RESEARCH OR DEVELOPMENT

This invention was made with government support under Grant No. DA030339 awarded by the National Institutes of Health. The government has certain rights in the invention.

FIELD OF THE INVENTION

Provided herein are methods for treating subjects having conditions related to adrenocortical activity and/or excessive steroid production. In particular, provided herein are methods for treating subjects having conditions related to adrenocortical activity and/or excessive steroid production through administration of at least one of the following agents: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity.

BACKGROUND OF THE INVENTION

The adrenal gland produces hormones that affects development and stress, growth, and also helps to regulate kidney function. There are two parts of the adrenal glands, the adrenal cortex and the adrenal medulla. The adrenal cortex produces mineralocorticoids, which regulate salt and water balance within the body, glucocorticoids (including cortisol) which have a wide number of roles within the body, and androgens, hormones with testosterone-like function. The adrenal medulla produces epinephrine and norepinephrine.

Conditions related to adrenal gland activity interfere with the normal functioning of the adrenal glands. Examples of such conditions include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension, virilization, congenital syndromes leading to excessive corticosteroid production, Conns or other syndromes of excessive steroid production, and adrenocortical cancer (ACC).

ACC is a malignancy of the adrenal cortex with a poor 5-year survival rate of 10-20%. A majority of cases are metastatic at the time of diagnosis, with the most common sites of spread being the local periadrenal tissue, lymph nodes, lungs, liver, and bone. AC is relatively rare, however, accounting for just 0.02-0.2% of all cancer-related deaths. Detection of tumors at an early clinical stage is crucial for curative resection. Many ACC patients have no symptoms until their tumors reach a large size.

Currently, there is no reasonably sensitive or specific way to distinguish ACC from the much more common benign adenomas. Diagnosis is made on the basis of tumor size and histopathological features that can be summarized by the Weiss score. Weiss scores of 0 or 1 are considered benign, 2 and 3 are ambiguous, and 4 or larger are cancerous. Histological diagnosis of AC is difficult to make, which makes treatment decisions complicated.

Current therapy is often ineffective and may also be associated with intolerable side effects. Indeed, ACC has a poor prognosis in most cases because no existing drugs can halt tumor growth indefinitely and because the high levels of circulating steroids that are produced by many tumors suppress immune responses and disrupt other physiological functions. Current combination treatments that are used to counteract tumor growth and to suppress excess steroid production are plagued by adverse effects, treatment resistance, and drug interactions that can compromise efficacy.

Improved treatments for condition related to adrenocortical activity and/or excessive steroid production are needed. The present invention addresses this need.

BRIEF SUMMARY OF THE INVENTION

Experiments conducted during the course of developing embodiments for the present invention determined that combinations of compounds that caused cholesterol accumulation in ACC-derived cells were cytotoxic. Indeed, it was shown that prevention of the cholesterol accumulation suppressed the cytotoxicity. It was shown that cholesterol accumulation could be caused by single compounds such as ATR-101, or could be caused by combinations of compounds, such as verapamil, benzamil and glyburide. The enhanced cytotoxicity of verapamil, benzamil and glyburide in combination suggested that cytotoxicity required the simultaneous inhibition of ABCA1, ABCG1 and MDR1 ABC transporters. The adrenalytic compound ATR-101 also inhibited cholesterol efflux and cortisol secretion.

Accordingly, the present invention provides methods for treating subjects having conditions related to adrenocortical activity and/or excessive steroid production. In particular, provided herein are methods for treating subjects having conditions related to adrenocortical activity and/or excessive steroid production through administration of at least one (e.g., one, two, three, etc.) of the following agents: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity.

In certain embodiments, the present invention provides methods of treating, ameliorating, or preventing a condition related to adrenocortical activity (e.g., functional activity) (e.g., dysfunctional activity) and/or excessive steroid production comprising administering to a patient a therapeutically effective amount of one or more agents that simultaneously inhibit at least two of the following cellular functions: 1) cholesterol efflux; 2) cortisol secretion; and 3) mitochondrial activity or ATP synthesis. In some embodiments, the patient is a human patient.

In some embodiments, the agent capable of inhibiting cholesterol efflux is capable of inhibiting cholesterol efflux related to ABCA1 and/or ABCG1 (e.g., ABCA1/ABCG1 transporters). In some embodiments, inhibiting cholesterol efflux related to ABCA1 and/or ABCG1 results in, for example, free cholesterol accumulation, increased caspase activity, and decreased ATP.

In some embodiments, the agent capable of inhibiting cortisol secretion is capable of inhibiting MDR1 related cortisol secretion and/or inhibiting MDR1 P-glycoprotein multiple drug transporter activity. In some embodiments, inhibiting cortisol secretion and/or inhibiting MDR1 related cortisol secretion and/or inhibiting MDR1 P-glycoprotein multiple drug transporter activity results in, for example, decreased steroid circulation.

In some embodiments, the agent capable of inhibiting mitochondrial activity or ATP synthesis. In some embodiments, inhibiting mitochondrial activity or ATP synthesis includes, but is not limited to, inhibiting mitochondrial electron transport chain activity related to cholesterol accumulation, and mitochondrial F1F0 ATPase activity related to cholesterol accumulation.

In some embodiments, the administering to said patient a therapeutically effective amount of one or more agents is administering to said patient a therapeutically effective amount of two or more agents. In some embodiments, the administering to said patient a therapeutically effective amount of one or more agents is administering to said patient a therapeutically effective amount of three or more agents. In some embodiments, the two or three or more agents are concurrently co-administered. In some embodiments, the two or three or more agents are not co-administered concurrently.

In some embodiments, the condition related to adrenocortical activity and/or excessive steroid production is selected from aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension, virilization, congenital syndromes leading to excessive corticosteroid production, Conns or other syndromes of excessive steroid production, and adrenocortical cancer (ACC).

The present invention contemplates that treatment involving administration of one or more of the following agents: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity satisfies an unmet need for the treatment of conditions related to adrenocortical activity (e.g., functional activity) (e.g., dysfunctional activity) and/or excessive steroid production, either when administered as monotherapy (e.g., to induce ACC related cell growth inhibition), (e.g., apoptosis and/or cell cycle arrest in ACC cells), or when administered in a temporal relationship with further additional agent(s) (e.g., additional agents capable of causing cytotoxic cholesterol accumulation) (e.g., cell death-inducing or cell cycle disrupting cancer therapeutic drugs or radiation therapies (combination therapies)), so as to render a greater proportion of the adrenal cells or supportive cells susceptible to the treatment (e.g., treatment for executing the apoptosis program) compared to the corresponding proportion of cells in an animal treated only with the additional therapy alone.

Moreover, the present invention contemplates that treatment involving co-administration of two or more of the following agents: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity satisfies an unmet need for the treatment of conditions related to adrenocortical activity (e.g., functional activity) (e.g., dysfunctional activity) and/or excessive steroid production, either when co-administered as monotherapy (e.g., to induce ACC related cell growth inhibition), (e.g., apoptosis and/or cell cycle arrest in ACC cells), or when administered in a temporal relationship with further additional agent(s) (e.g., additional agents capable of causing cytotoxic cholesterol accumulation) (e.g., cell death-inducing or cell cycle disrupting cancer therapeutic drugs or radiation therapies (combination therapies)), so as to render a greater proportion of the adrenal cells or supportive cells susceptible to the treatment (e.g., treatment for executing the apoptosis program) compared to the corresponding proportion of cells in an animal treated only with the additional therapy alone.

In certain embodiments of the invention, treatment of animals with a therapeutically effective amount one or more agents that simultaneously inhibit at least two of the following cellular functions: 1) cholesterol efflux; 2) cortisol secretion; and 3) mitochondrial activity or ATP synthesis produces a greater therapeutic response (e.g., therapeutic tumor response) and clinical benefit in such animals compared to those treated with an agent not capable of simultaneously inhibiting at least two of the following cellular functions: 1) cholesterol efflux; 2) cortisol secretion; and 3) mitochondrial activity or ATP synthesis.

In certain embodiments of the invention, combination treatment of animals with a therapeutically effective amount of two or more of 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity produces a greater therapeutic response (e.g., therapeutic tumor response) and clinical benefit in such animals compared to those treated with either agent alone.

In cases involving the treatment of ACC and/or cancers related to adrenocortical activity, the invention also provides the use of treatments involving administration of one or more agents that simultaneously inhibit at least two of the following cellular functions: 1) cholesterol efflux; 2) cortisol secretion; and 3) mitochondrial activity or ATP synthesis to induce cell cycle arrest and/or apoptosis in ACC cells. The invention also relates to the use of such administration treatments for sensitizing ACC cells to additional agent(s), such as inducers of apoptosis and/or cell cycle arrest, and chemoprotection of normal cells through the induction of cell cycle arrest prior to treatment with chemotherapeutic agents.

Moreover, in cases involving the treatment of ACC and/or cancers related to adrenocortical activity, the invention also provides the use of treatments involving co-administration of two or more of 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity to induce cell cycle arrest and/or apoptosis in ACC cells. The invention also relates to the use of such co-administration treatments for sensitizing ACC cells to additional agent(s), such as inducers of apoptosis and/or cell cycle arrest, and chemoprotection of normal cells through the induction of cell cycle arrest prior to treatment with chemotherapeutic agents.

Such co-administration of agents are useful for the treatment, amelioration, or prevention of disorders, such as those responsive to induction of apoptotic cell death, e.g., disorders characterized by dysregulation of apoptosis, including hyperproliferative diseases such as ACC. In certain embodiments, such co-administration can be used to treat, ameliorate, or prevent ACC that is characterized by resistance to ACC therapies (e.g., those cancer cells which are chemoresistant, radiation resistant, hormone resistant, and the like).

Such methods are not limited to a particular agent capable of causing cytotoxic cholesterol accumulation and/or capable of inhibiting cholesterol efflux related to ABCA1 and/or ABCG1 (e.g., ABCA1/ABCG1 transporters). In some embodiments, inhibiting cholesterol efflux related to ABCA1 and/or ABCG1 results in, for example, free cholesterol accumulation, increased caspase activity, and decreased ATP. In some embodiments, agents capable of causing cytotoxic cholesterol accumulation and/or capable of inhibiting cholesterol efflux related to ABCA1 and/or ABCG1 (e.g., ABCA1/ABCG1 transporters) include, but are not limited to, Valspodar, Glyburide, Cyclosporine A (see, e.g., Le Goff, et al., Arteriosclerosis, Thrombosis, and Vascular Biology. 2004; 24:2155-2161).

In some embodiments, the agent is capable of inhibiting cortisol secretion and/or inhibiting MDR1 related cortisol secretion and/or inhibiting MDR1 P-glycoprotein multiple drug transporter activity. In some embodiments, inhibiting cortisol secretion and/or inhibiting MDR1 related cortisol secretion and/or inhibiting MDR1 P-glycoprotein multiple drug transporter activity results in, for example, decreased steroid circulation. In some embodiments, agents capable of inhibiting cortisol secretion and/or inhibiting MDR1 related cortisol secretion and/or inhibiting MDR1 P-glycoprotein multiple drug transporter activity include, but are not limited to, Tariquidar, MK-571 (CAS 115103-85-0), Niguldipine hydrochloride (CAS 113317-61-6), Matairesinol (CAS 580-72-3), Reversin 121 ($C_{34}H_{47}N_3O_9$), Elacridar (CAS 143664-11-3), Pyrimethamine ($C_{12}H_{13}ClN_4$), Pyrimethamine Biotin ($C_{27}H_{39}N_7O_3S$), Pyrimethamine-d3 ($C_{12}H_{10}D_3ClN_4$), 8-isopentenylnaringenin (CAS 68682-02-0), JS-2190 (Boc-Glu(OBzl)-N,N'-dicyclohexylurea, $C_{30}H_{45}N_3O_6$), P-Glycoprotein Inhibitor C-4 ($C_{23}H_{18}ClNO_4$), PGP-4008 (CAS 365565-02-2), Sipholenol A (CAS 365565-02-2), Reversan (CAS 313397-13-6), CP 100356 hydrochloride (CAS 142716-85-6), PSC 833 (CAS121584-18-7), Zosuquidar trihydrochloride (CAS 167465-36-3), and Vismodegib (CAS 879085-55-9).

In some embodiments, the agent is capable of inhibiting mitochondrial activity or ATP synthesis. In some embodiments, inhibiting mitochondrial activity or ATP synthesis includes, but is not limited to, inhibiting mitochondrial electron transport chain activity related to cholesterol accumulation, and mitochondrial F1F0 ATPase activity related to cholesterol accumulation. In some embodiments, agents capable of inhibiting mitochondrial activity include, but are not limited to, rhodamine-123, MKT-077, decoquinate, isoniazid, suramin, erythrosine, toltrazuril, enilconazole, and metformin.

In some embodiments, any of the methods recited herein involve further administration of ATR-101.

The invention also provides pharmaceutical compositions comprising one or more of the following: 1) cholesterol efflux; 2) cortisol secretion; and 3) mitochondrial activity or ATP synthesis in a pharmaceutically acceptable carrier. The invention also provides pharmaceutical compositions comprising two or more of such agent in a pharmaceutically acceptable carrier. The invention also provides pharmaceutical compositions comprising three of such agents in a pharmaceutically acceptable carrier.

The invention also provides pharmaceutical compositions comprising one or more of the following: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity in a pharmaceutically acceptable carrier. The invention also provides pharmaceutical compositions comprising two or more of such agent in a pharmaceutically acceptable carrier. The invention also provides pharmaceutical compositions comprising three of such agents in a pharmaceutically acceptable carrier.

The invention also provides kits comprising two or more of the following: The invention also provides pharmaceutical compositions comprising two or more of 1) cholesterol efflux; 2) cortisol secretion; and 3) mitochondrial activity or ATP synthesis in a pharmaceutically acceptable carrier. In some embodiments, such kits further comprise instructions for administering the pharmaceutical compositions to an animal. The kits may optionally contain other therapeutic agents, e.g., anticancer agents or apoptosis-modulating agents or additional agents capable of causing cytotoxic cholesterol accumulation.

The invention also provides kits comprising two or more of the following: The invention also provides pharmaceutical compositions comprising two or more of 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity in a pharmaceutically acceptable carrier. In some embodiments, such kits further comprise instructions for administering the pharmaceutical compositions to an animal. The kits may optionally contain other therapeutic agents, e.g., anticancer agents or apoptosis-modulating agents or additional agents capable of causing cytotoxic cholesterol accumulation.

BRIEF DESCRIPTION OF THE DRAWINGS

For any colors described in relation to the drawings, the colors have been gray-scaled.

Effects of ATR-101 versus PD129337 on cholesterol accumulation, cholesterol esterification, ATP levels and caspase 3/7 activities in ACC-derived cells.

Effects of ATR-101 versus PD129337 on the cholesterol levels, cholesterol esterification, ATP levels, and caspase 3/7 activities in H295R cells.

Figure 2A:
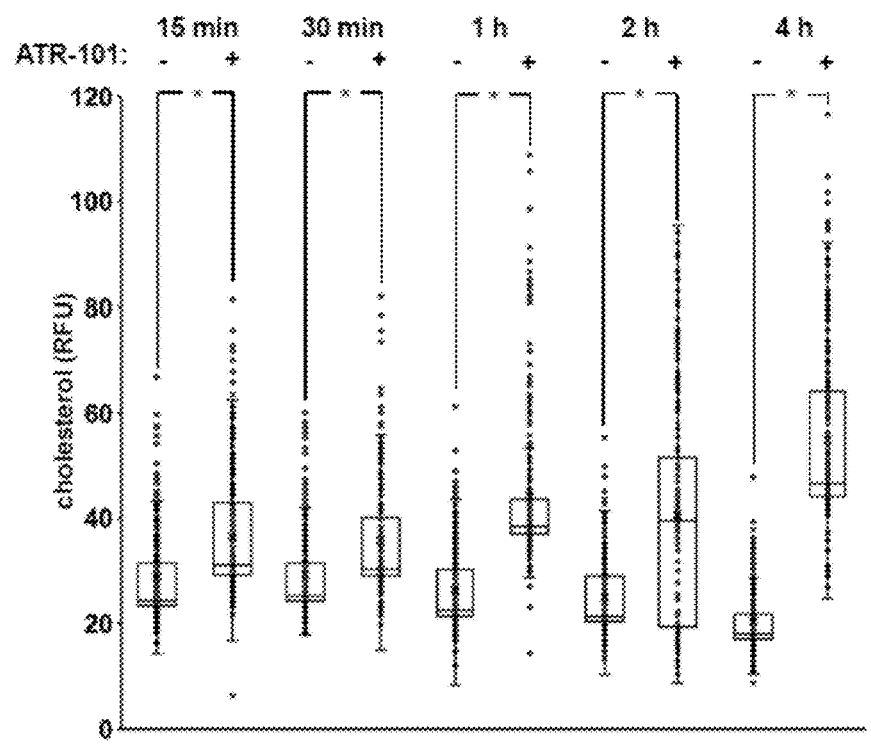

FIG. 2A. Quantitation of the time-dependence of the change in cholesterol levels in H295R cells after ATR-101 addition. H295R cells were cultured with DMSO vehicle (−) or with 60 μM ATR-101 (+) for the indicated times. The cells were fixed and stained with filipin III. Filipin III fluorescence was visualized by fluorescence microscopy using a 4× objective. The mean fluorescence intensities and areas of 220 to 310 individual H295R cell clusters (approximately 5500-7800 cells) for each time and condition were quantified using ImageJ v1.50i software. To quantify the areas and intensities of the clusters, manual fluorescence intensity thresholding was used to divide each image into signal comprising the cell clusters and background. The intensity divided by the area was plotted for each cell cluster. The mean, quartiles and standard deviation were plotted at each time after ATR-101 addition. The statistical significance of the differences in fluorescence intensity after ATR-101 addition were evaluated by using unpaired two-tailed Student's t-tests (Cells cultured with ATR-101 versus corresponding control cells; *$P<0.05$). The data are representative of two experiments.

ATR-101 caused an increase in cholesterol accumulation within 15 minutes after addition to H295R cells. There was a wide range of filipin III intensities among different cell clusters, but the majority of cell clusters had a narrower range of intensities as indicated by the quartiles shown.

Figure 2B:
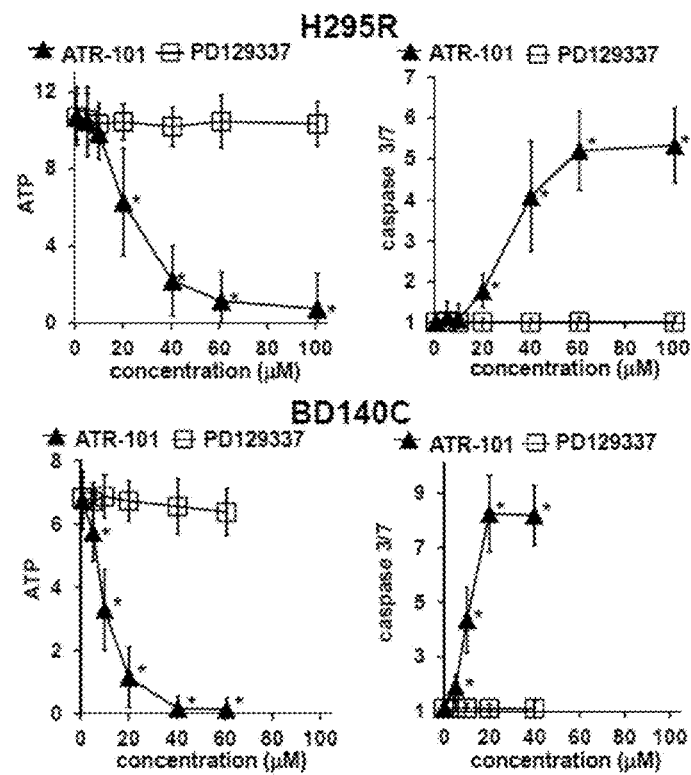

FIG. 2B: Effects of different concentrations of ATR-101 versus PD129337 on the ATP levels and on the caspase 3/7 activities in H295R (upper graphs) and BD140C (lower graphs) cells. The cells were cultured with the indicated concentrations of ATR-101 (closed triangles) or PD129337 (open squares) for 24 h. The ATP levels (left graphs) and the caspase 3/7 activities (right graphs) were measured in cells that were cultured in parallel. The graphs show the means and the standard deviations of six samples from three experiments. The statistical significance of the differences in ATP levels and caspase 3/7 activities in cells that were cultured with each concentration of ATR-101 or PD129337 were evaluated by using two-way analysis of variance followed by Sidak's post hoc tests (ATR-101 vs. PD129337, *$P<0.05$).

ATR-101 reduced the ATP levels and increased the caspase 3/7 activities in H295R and BD140C cells. The concentrations of ATR-101 that were required for ATP depletion and for caspase 3/7 activation were similar in each of the cells lines, but they were slightly different between H295R and BD140C cells. PD129337 had no detectable effect on the ATP levels or the caspase 3/7 activities in these cells. ACAT inhibition was therefore not sufficient to cause ATP depletion or caspase 3/7 activation in these cells.

Figure 2C:
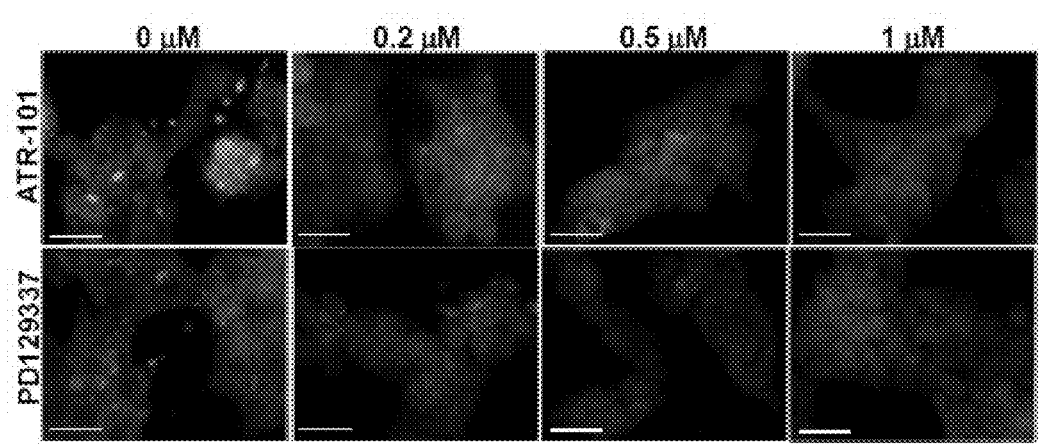

FIG. 2C: Effects of different concentrations of ATR-101 versus PD129337 on NBD-cholesterol esterification in H295R cells. The cells were incubated with the indicated concentrations of ATR-101 or PD129337 for 2 h, followed by 2 h with added NBD-cholesterol (1 μg/ml). The images show NBD (green) and Hoechst (blue) fluorescence captured with a 20× objective and are representative of two independent experiments. The concentrations of ATR-101 and PD129337 that inhibited cholesterol esterification in H295R and BD140C cells were similar to the concentrations that inhibit ACAT enzyme activity in vitro (see, e.g., Trivedi, et al., 1993, J Med Chem, 36, 3300-7; Trivedi, et al., 1994, J Med Chem, 37, 1652-9). The scale bars denote 30 μm.

Experiments were conducted that compared the effects of ATR-101 and of PD129337 on cholesterol esterification in ACC-derived cells by imaging NBD-cholesterol accumulation in lipid droplets. PD129337 inhibited NBD-cholesterol accumulation more effectively than ATR-101. The inhibition of NBD-cholesterol esterification by low concentrations of ATR-101 and by PD129337 does not correlate with cholesterol accumulation or with ATP depletion or caspase 3/7 activation in H295R cells. The inhibition of cholesterol esterification as well as other effects of PD129337 in H295R cells (Fig. S7A) indicate that PD129337 accessed the same locations as ATR-101 in cells.

Figure 1C:
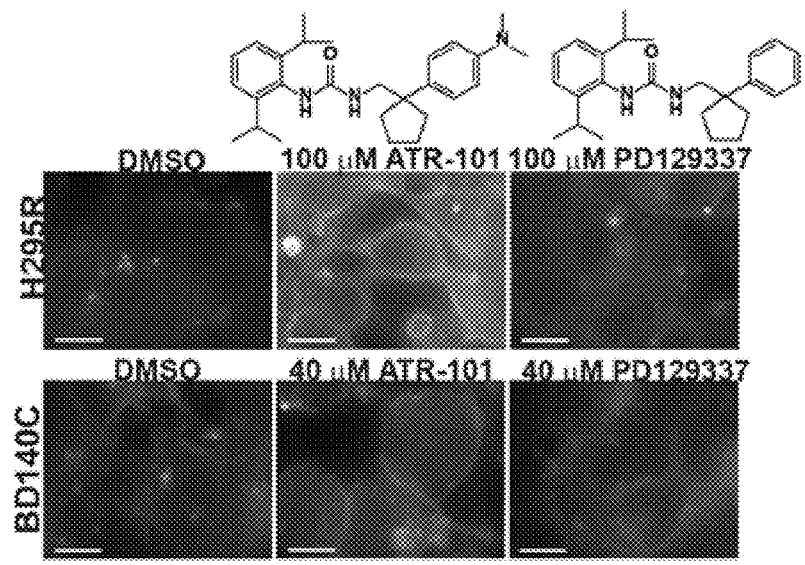
FIG. 1C: Effects of ATR-101 versus PD132997 on the cholesterol levels in H295R and BD140C cells. H295R (upper images) and BD140C (lower images) cells were cultured with DMSO vehicle, ATR-101, or PD129337 at the indicated concentrations for 4 h. The images show filipin III binding to cholesterol, and are representative of images collected in two separate experiments for each cell line. The scale bars denote 10 μm. The full fields from which the images were cropped are shown in FIG. 2D.
Figure 2D:
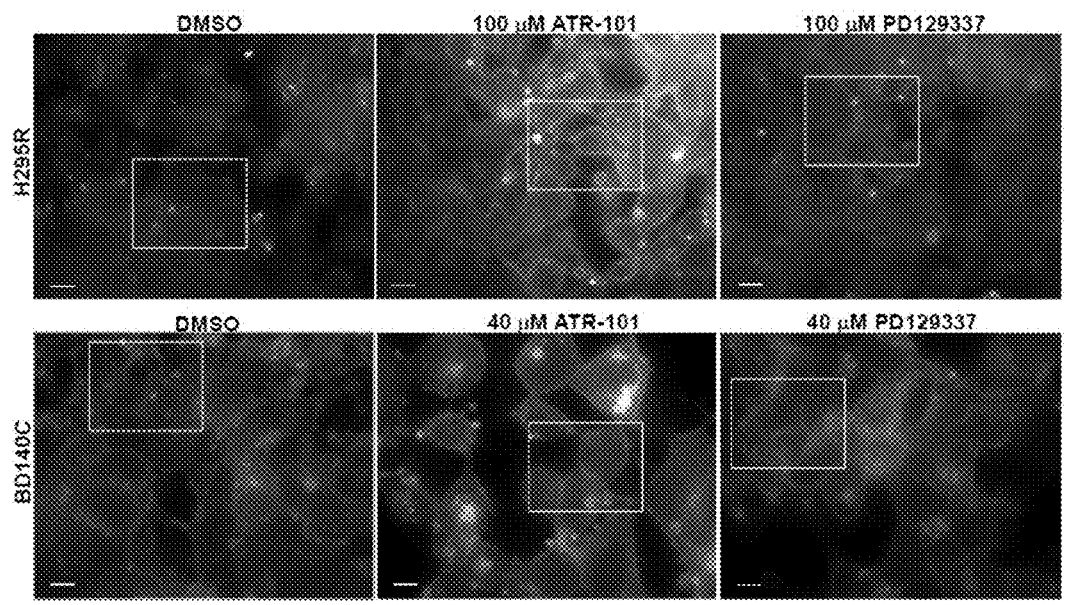

FIG. 2D: The entire fields from which the images in FIG. 1C were cropped are shown for H295R (upper images) and for BD140C (lower images) cells. H295R and BD140C cells were cultured with DMSO vehicle or with the indicated concentrations of ATR-101 or of PD129337 for 4 h. After 4 h, the media was removed from the cells and immediately replaced with 4% paraformaldehyde and fixed at room temperature for 20 min. Cells were washed twice in PBS. Prior to staining, a stock solution of filipin III was prepared in DMSO (10 mg/ml). The filipin III stock solution was diluted 100× in PBS for a final concentration of 100 μg/ml and added directly to cells. Cells were incubated with filipin III at 37 C in the dark for 2 h, washed twice in PBS. Filipin III fluorescence was visualized by confocal fluorescence microscopy using an excitation wavelength of 387/11 nm with a 60× oil objective. The images show filipin III fluorescence and are representative of two independent experiments for each cell line. The scale bars denotes 10 µm.

ATR-101 caused an increase in cholesterol accumulation in the plasma membrane. The filipin III staining intensities of individual cells in a cluster varied, and the overall filipin III staining intensities of H295R cells that were cultured with ATR-101 were significantly different from control cells and cells that were cultured with PD129337.

Figure 1E:
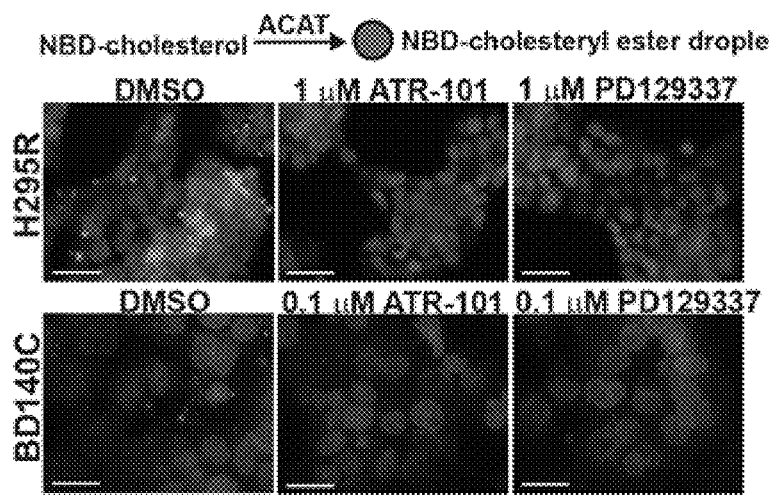
FIG. 1E: Effects of ATR-101 versus PD129337 on cholesterol esterification in H295R and BD140C cells. H295R (upper images) and BD140C (lower images) cells were cultured with DMSO vehicle, or with the indicated concentrations of ATR-101 or PD129337 for 2 h, followed by an additional 2 h after the addition of 1 μg/ml NBD-cholesterol. The images show NBD-cholesterol ester (green) and Hoechst (blue) fluorescence and are representative of images collected in five separate experiments for each cell line. The scale bars denote 30 μm. The effects of different concentrations of ATR-101 and of PD129337 on cholesterol esterification are shown in FIG. 2C. The full fields from which the images were cropped are shown in FIG. 2E.
Figure 2E:
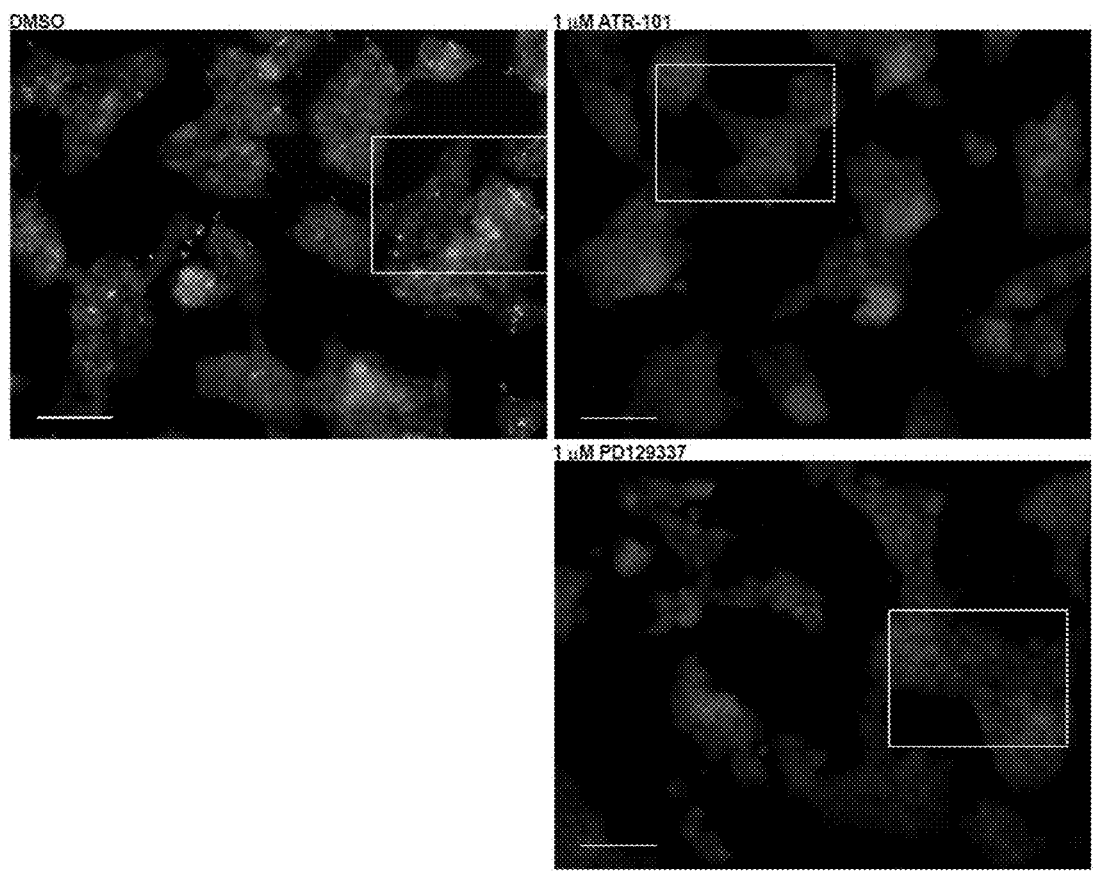

FIG. 2E: The entire fields from which the images in FIG. 1E were cropped are shown. H295R cells were incubated with 1 µM of ATR-101 or PD129337 for 2 h, followed by 1.5 h with added NBD-cholesterol (1 µg/ml). After 1.5 h, Hoechst 33342 was added at a final concentration of 3 µg/ml. After 30 min, the media was removed and replaced with fresh media. The cells were visualized using confocal fluorescence microscopy using excitation wavelengths of either 485/20 nm (NBD) or 387/11 nm (Hoechst) with a 20× objective. The images show NBD (green) and Hoechst (blue) fluorescence and are representative of images collected in five independent experiments for each cell line. The scale bars denote 30 µm. NBD-cholesterol produced a variable number of foci with intense fluorescence and a diffuse fluorescence of variable intensity in control H295R cells. ATR-101 and PD129337 at low concentrations eliminated both the intense foci and the diffuse fluorescence.

Effects of MβCD and of exogenous cholesterol in combination with ATR-101 on cholesterol accumulation and on cytotoxicity.

Figure 4A:
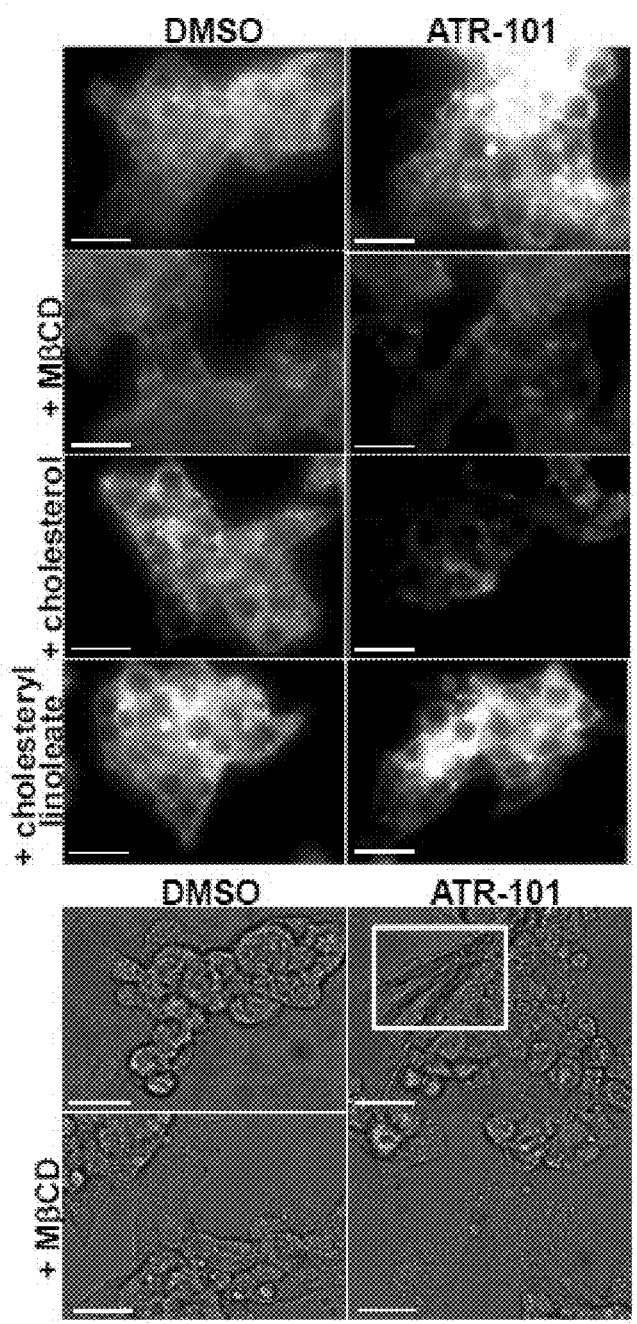
Figure 4B:
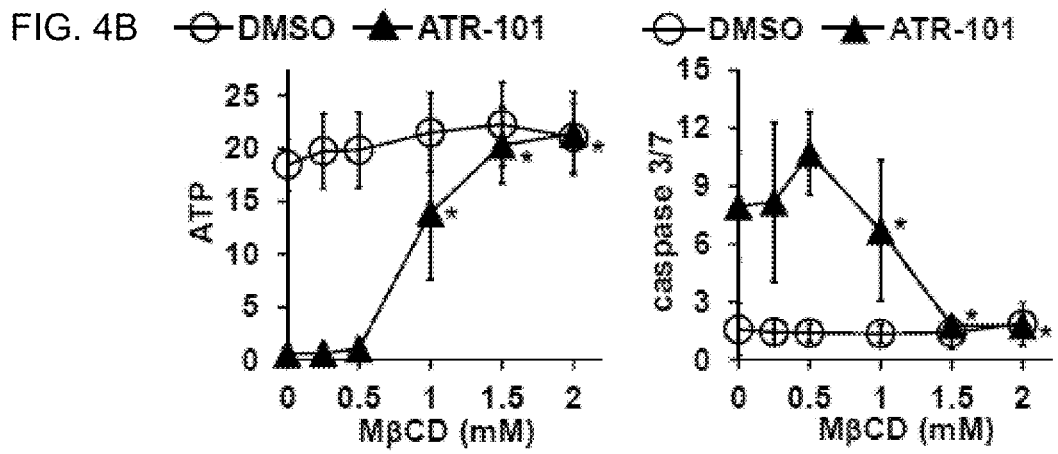
Figure 4C:
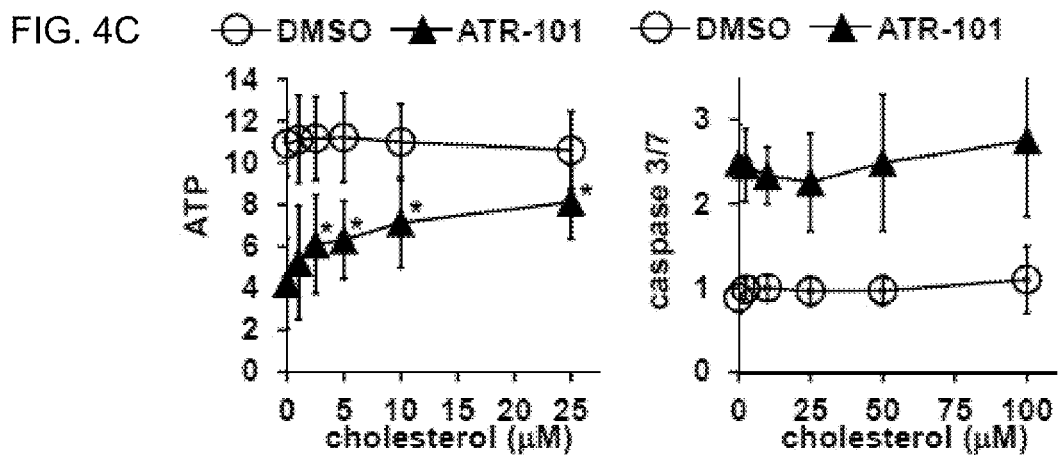

FIG. 3A: Effects of MβCD and ATR-101 separately and in combination on the cholesterol levels in H295R cells. The cells were cultured with DMSO vehicle (upper images) or with 100 µM ATR101 (lower images), alone (left images) or together with of 2 mM MβCD (right images) for 4 h. The images show filipin III binding to cholesterol, and are representative of images from four separate experiments. The cholesterol levels of H295R cells that were cultured with ATR-101 and MβCD for 24 h are shown in FIG. S2A. The full fields from which the images were taken are shown in FIG. 4J. The scale bars denote 10 µm.

FIG. 3B: Effects of MβCD on ATP depletion and caspase 3/7 activation by ATR-101 in H295R cells. The cells were cultured with DMSO vehicle or 50 µM ATR-101 together with the indicated concentrations of MβCD for 4 h. The ATP levels (left graphs) and the caspase 3/7 activities (right graphs) were measured in cells that were grown in parallel. The graphs show the means and the standard deviations of six samples from three experiments. The statistical significance of the differences in ATP levels and the caspase 3/7 activities in cells cultured with each concentration of MβCD were evaluated by using one-way analysis of variance followed by Dunnett's post hoc tests (cells cultured with MβCD vs. corresponding controls, *P<0.05). The ATP levels and the caspase 3/7 activities of cells that were cultured with ATR-101 and MβCD for 24 h are shown in FIG. 4B. Representative fields of cells that were cultured with ATR-101 and MβCD separately and in combination are shown in FIG. 4E.

FIG. 3C: Effects of exogenous cholesterol and ATR-101 separately and in combination on the cholesterol levels in H295R cells. The cells were cultured with DMSO vehicle (upper images) or with 50 µM ATR-101 (lower images) together with ethanol control (left images) or 10 µM exogenous cholesterol (right images) for 4 h. The images show filipin III binding to cholesterol, and are representative of two separate experiments. The scale bars denote 10 µm. The levels of cholesterol in H295R cells that were cultured with ATR-101 and exogenous cholesterol for 24 h are shown in FIG. 4A. The full fields from which the images were cropped are shown in FIG. 4K.

FIG. 3D: Effects of exogenous cholesterol on ATP depletion and caspase 3/7 activation by ATR-101 in H295R cells. The cells were cultured with DMSO vehicle or 50 µM ATR-101 together with the indicated concentrations of exogenous cholesterol for 24 h. The ATP levels (left graph) and the caspase 3/7 activities (right graph) were measured in cells that were grown in parallel. The graphs show the means and the standard deviations of five samples from three experiments. The statistical significance of the differences in ATP levels and the caspase 3/7 activities in cells that were cultured with each concentration of exogenous cholesterol were evaluated by using one-way analysis of variance followed by Dunnett's post hoc tests (cells that were cultured with with exogenous cholesterol vs. corresponding controls, *P<0.05). The ATP levels and the caspase 3/7 activities of H295R cells that were cultured with ATR-101 and exogenous cholesterol for 4 h are shown in FIG. 4C. Representative fields of cells that were cultured with ATR-101 and exogenous cholesterol separately and in combination are shown in FIG. 4E.

FIG. 3E: Cholesterol crystallization at the plasma membrane of cells cultured with ATR-101. H295R cells were cultured with 40 µM ATR-101 for 24 h. The scale bar denotes 10 µm.

FIG. 3F: Comparison of the amounts of extracellular cholesterol that were associated with H295R cells that were cultured with ATR-101 and exogenous cholesterol separately and in combination (left graph), and the rate of cholesterol efflux from control cells (right graph). The cells were cultured for 4 h in serum-containing medium containing 100 µM ATR-101 or 40 µM cholesterol separately and in combination. The culture medium was removed, and the extracellular cholesterol that was associated with the cells (left graph) was recovered by washing the cells in serum-free medium with (solid bars) or without (open bars) 50 µM glibenclamide (left graph). The rate of cholesterol efflux (right graph) was measured by removing the medium and adding serum-free medium to control cells. This medium was removed at the times indicated and the cholesterol concentration was measured. The statistical significance of the differences in the cholesterol levels associated with cells that were cultured with ATR-101 or exogenous cholesterol without glibenclamide (left graph) as well the cholesterol levels in the medium of control cells (right graph) were evaluated by using one-way analysis of variance followed by Dunnett's post hoc tests (left graph: cells cultured with with ATR-101 and/or cholesterol vs. cells cultured with DMSO; right graph: cells cultured for different times vs. controls at time 0, *P<0.05).

Effects of MβCD and of exogenous cholesterol in combination with ATR-101 on cholesterol levels, ATP levels, caspase 3/7 activities, and cholesterol crystallization.

FIG. 4A: Effects of MβCD and of exogenous cholesterol in combination with ATR-101 on the cholesterol levels of H295R cells. The cells were cultured with DMSO vehicle (left images) or with 40 µM ATR101 (right images) alone (top row), together with 2 µM MβCD (second row), 160 µM cholesterol (third row), or 160 µM cholesterol linoleate (fourth row) for 24 h. MβCD is a cholesterol-binding compound that removes unesterified cholesterol from cell membranes (see, e.g., Yu, et al., 2005, J Biol Chem, 280, 11731-9; Le Goff, et al., 2006, J Lipid Res, 47, 51-8; Mahammad and Parmryd, 2008, Biochim Biophys Acta, 1778, 1251-8). Cholesterol was visualized using filipin III. The images show filipin III fluorescence (upper set of images) and phase contrast (lower set of images), and are representative of two independent experiments. The scale bars denote 30 μm.

ATR-101 caused an increase in intracellular cholesterol and in cholesterol crystallization at the plasma membrane. MβCD blocked the effects of ATR-101 on cholesterol accumulation and on cholesterol crystallization at the plasma membrane. The cholesterol crystals were not visualized by filipin III, suggesting that the crystalline cholesterol is either inaccessible to filipin III binding, or is dislodged during the staining procedure. Exogenous cholesterol linoleate did not prevent the accumulation of cellular cholesterol in response to ATR-101.

FIG. 4B: Effects of MβCD on ATP depletion and caspase 3/7 activation by ATR-101 in H295R cells. The cells were cultured with the indicated concentrations of MβCD together with DMSO vehicle or 50 μM ATR-101 for 24 h. The ATP levels (left graph) and the caspase 3/7 activities (right graph) were measured in cells that were grown in parallel. The graphs show the means and the standard deviations of six samples from three experiments. The statistical significance of the differences in ATP levels and caspase 3/7 activities in cells that were cultured with each concentration of MβCD were evaluated by using one-way analysis of variance followed by Dunnett's post hoc tests (cells cultured with MβCD vs. corresponding controls, *P<0.05).

MβCD suppressed the depletion of ATP and caspase 3/7 activation by ATR-101 in a concentration-dependent manner after 4 h.

FIG. 4C: Effects of exogenous cholesterol on ATP depletion and the caspase 3/7 activation by ATR-101 in H295R cells. The cells were incubated with DMSO or with 50 μM ATR-101 together with the indicated concentrations of exogenous cholesterol for 4 h. The ATP levels (left graph) and the caspase 3/7 activities (right graph) were measured in cells that were grown in parallel. The graphs show the means and the standard deviations of six samples from three experiments. The statistical significance of the differences in ATP levels and caspase 3/7 activities in cells that were cultured with each concentration of exogenous cholesterol were evaluated by using one-way analysis of variance followed by Dunnett's post hoc tests (cells cultured with exogenous cholesterol vs. vs. corresponding controls, *P<0.05).

Exogenous cholesterol reduced ATP depletion, but did not affect caspase 3/7 activation by ATR-101 after 4 h. The differential effects of exogenous cholesterol on ATP depletion versus caspase 3/7 activation by ATR-101 demonstrate that ATP depletion and caspase 3/7 activation by ATR-101 are independent.

Figure 4D:
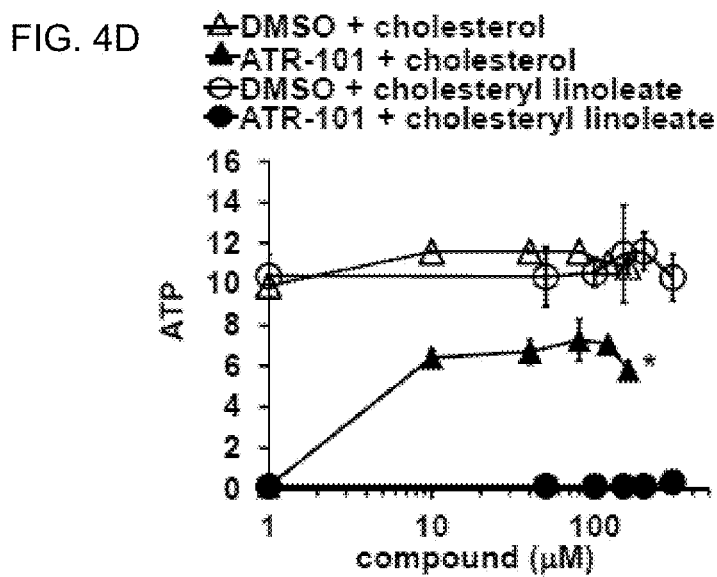
Figure 4E:
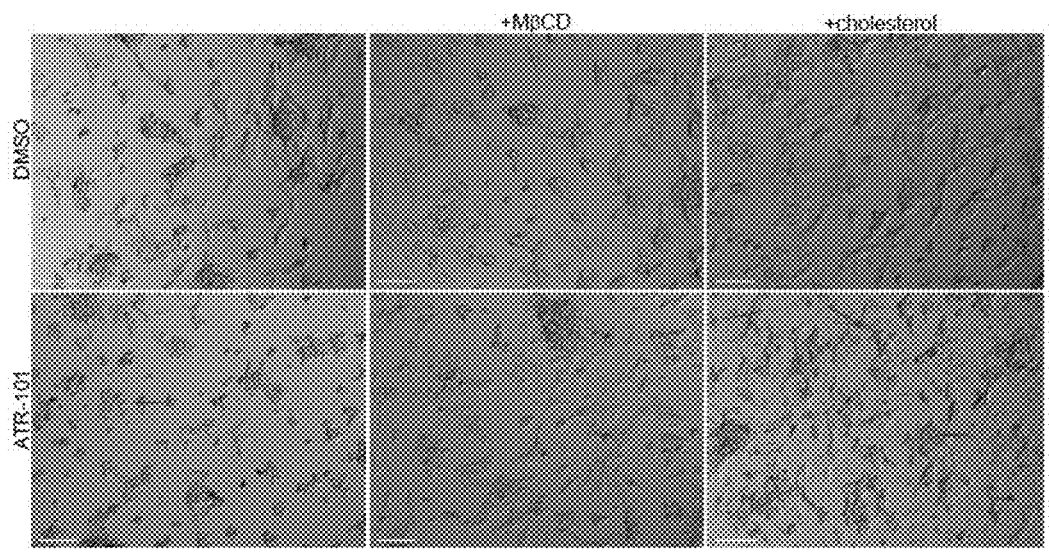

FIG. 4D: Comparison of the effects of exogenous cholesterol and exogenous cholesterol linoleate on ATP depletion by ATR-101. H295R cells were cultured with DMSO or with 40 μM ATR-together with the indicated concentrations of exogenous cholesterol or exogenous cholesterol linoleate for 24 h and the ATP levels were measured. The graphs show the means and the standard deviations of two samples from one experiment and are representative of two experiments. The statistical significance of the difference in ATP levels in cells that were cultured with ATR-101 and cholesterol or ATR-101 and cholesterol linoleate was evaluated by using unpaired two-tailed Student's t-test (n=6, *P<0.05). The ATP levels that are shown in FIG. 4D were measured in parallel with the visualization of cholesterol by filipin III binding in FIG. 4A.

Exogenous cholesterol but not exogenous cholesterol linoleate inhibits ATP depletion by ATR-101 after 24 h. The distinct effects of the exogenous cholesterol versus the cholesterol linoleate as well as the accumulated cellular cholesterol indicate that the exogenous cholesterol suppressed ATR-101 cytotoxicity by acting through a mechanism or at a location that was not accessible to the cholesterol that was generated inside cells that were cultured with ATR-101.

FIG. 4E: Visualization of the effects of ATR-101 alone and in combination with MβCD or exogenous cholesterol on cell morphology after 30 h. The cells were cultured with DMSO vehicle (upper images) or with 40 μM ATR-101 (lower images) alone (left images), or in combination with 1.5 mM MβCD (middle images), or in combination with 40 μM cholesterol (right images). Cell morphology was visualized by phase contrast microscopy using a 10× objective. The images are representative of 5 fields under each set of culture conditions. The scale bars denote 100 μm.

H295R cells incubated with ATR-101 were small, rounded and weakly attached to the plate after 30 h. These changes in morphology are consistent with the loss of cell viability. The effects of ATR-101 on cell morphology were prevented in cells that were cultured with ATR-101 in combination with either MβCD or cholesterol.

Figure 4F:
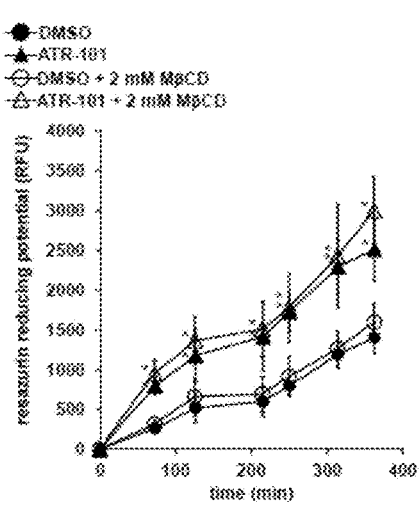

FIG. 4F: Effect of ATR-101 on resazurin reducing potential in H295R cells. The cells were cultured with DMSO vehicle or 32 μM ATR-101 alone, or together with 2 mM MβCD. Resazurin fluorescence intensity was measured using a microplate reader at the indicated times at 37 C. The background signal of wells without resazurin was subtracted. The graph shows the means and the standard deviations of six samples from three experiments. The statistical significance of the differences in resazurin reducing potential at each time after ATR-101 addition in either the absence or presence of MβCD were evaluated by using two-way analysis of variance followed by Sidak's post hoc tests (ATR-101 vs. DMSO control, *P<0.05).

ATR-101 caused a sustained increase in resazurin fluorescence 1 h after addition to the culture medium. The increase in resazurin fluorescence caused by ATR-101 was not inhibited by MβCD, indicating that it was independent of cholesterol accumulation or ATP depletion by ATR-101.

Figure 4G:
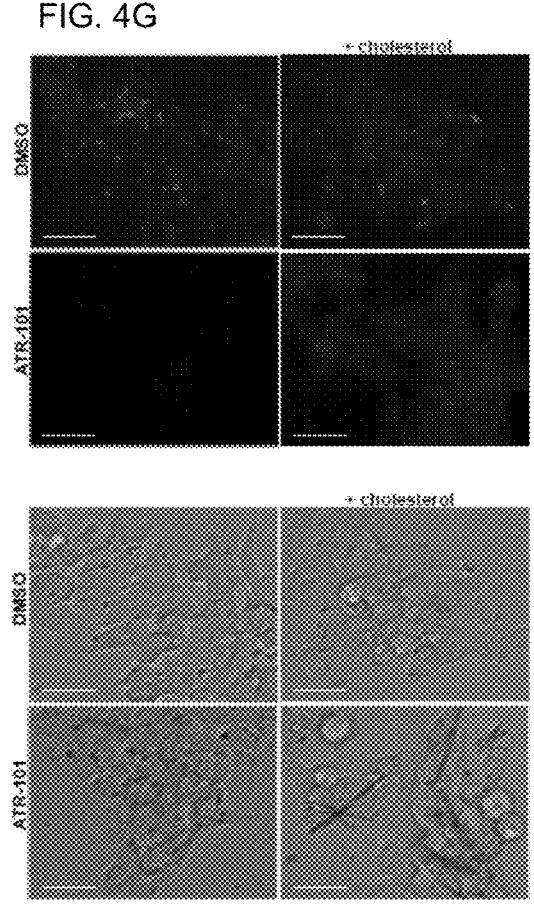

FIG. 4G: Effects of ATR-101 in combination with exogenous cholesterol on NBD-cholesterol esterification and on extracellular cholesterol crystal formation in H295R cells. H295R cells were incubated with DMSO or with 100 μM ATR-101 alone or together with 40 μM of exogenous cholesterol for 2 h, followed by 2 h with added NBD-cholesterol (1 μg/ml). The images show NBD (green) fluorescence (left images) and phase contrast (right images) captured with a 60× objective. The scale bars denote 30 μm.

ATR-101 inhibits NBD-cholesterol esterification in the absence and in the presence of exogenous cholesterol. This indicates that exogenous cholesterol did not prevent ATR-101 entry into cells, or the inhibition of cholesterol esterification by ATR-101.

Exogenous cholesterol in combination with ATR-101 increased the amount of extracellular cholesterol crystals and prevented intracellular cholesterol accumulation. Abundant crystals were observed at cells that were cultured with ATR-101 together with exogenous cholesterol for 4 h, whereas cholesterol crystals were not visible at cells that were cultured with ATR-101 or exogenous cholesterol separately for 4 h. It was hypothesized that the exogenous cholesterol nucleates cholesterol crystallization at the plasma membrane. The increase in cholesterol crystallization at cells that were cultures with ATR-101 and exogenous cholesterol was corroborated by measurement of the amount of cell-associated cholesterol that was associated with the cells (FIG. 3F). The amount of cholesterol that was released into the wash medium during the 30 second wash is a minimum estimate of the extracellular cholesterol that was associated with the cells since a larger amount of cholesterol was released during a longer incubation with the wash medium. It is unlikely that the extracellular cholesterol was released by cell lysis since cells that were cultured with ATR-101 together with exogenous cholesterol had a higher ATP level and a lower caspase 3/7 activity than cells that were cultures with ATR-101 alone. This indicates that the protection from ATR-101 cytotoxicity by exogenous cholesterol correlates with cholesterol crystal formation and an increase in the amount of extracellular cholesterol that is associated with the cells.

Figure 4H:
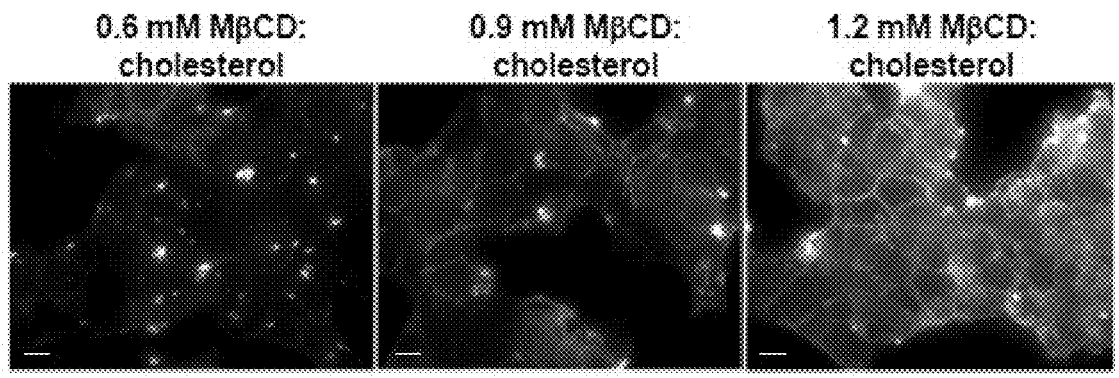

FIG. 4H: Effects of cholesterol:MβCD on the cholesterol levels of H295R cells. The cells were cultured with the indicated concentrations of cholesterol:MβCD for 4 h. The images show filipin III fluorescence and are representative of images from two separate experiments. The scale bars denote 10 μm.

Experiments were conducted that investigated the effects of cholesterol accumulation independently of ATR-101 by culturing H295R cells in the presence of cholesterol:MβCD. Cholesterol:MβCD concentrations that were 10-100 fold higher than the concentrations of exogenous cholesterol increased the intracellular cholesterol levels of H295R cells. At moderate cholesterol:MβCD concentrations (0.6 mM), the cholesterol was localized mainly to intracellular foci, and at the highest cholesterol:MβCD concentrations (1.2 mM), the cholesterol accumulated mainly in the plasma membrane. Experiments were unable to visualize the cholesterol in cells that were cultured with cholesterol:MβCD in combination with ATR-101 since the cells that were cultured under these conditions did not adhere to slides under the conditions that are required to visualize filipin III binding.

Figure 4I:
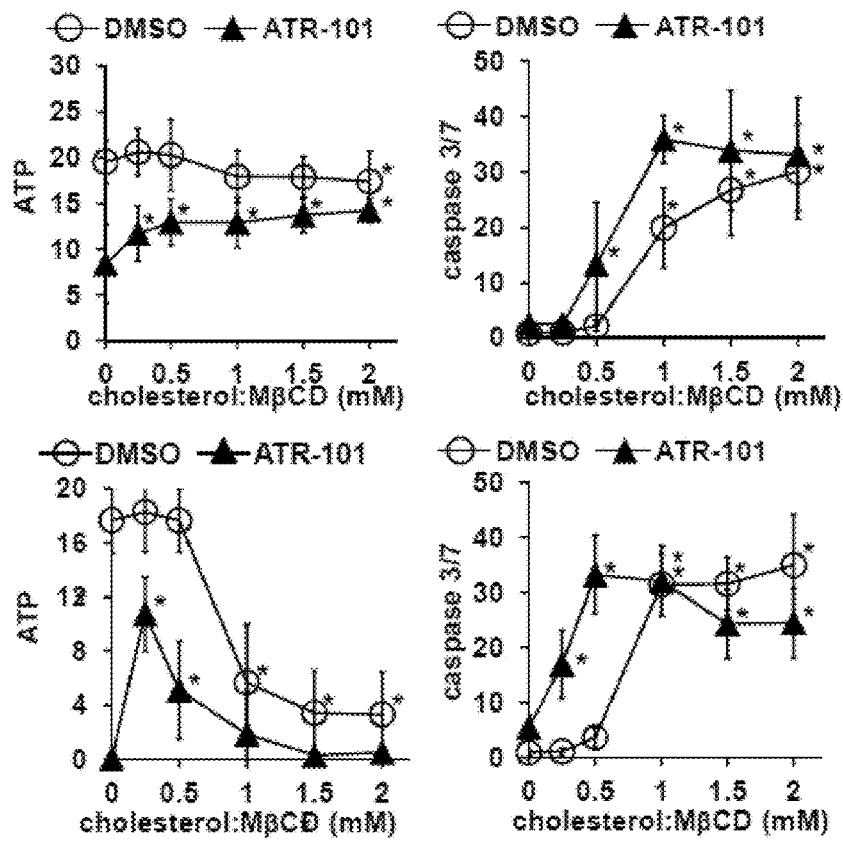
Figure 4J:
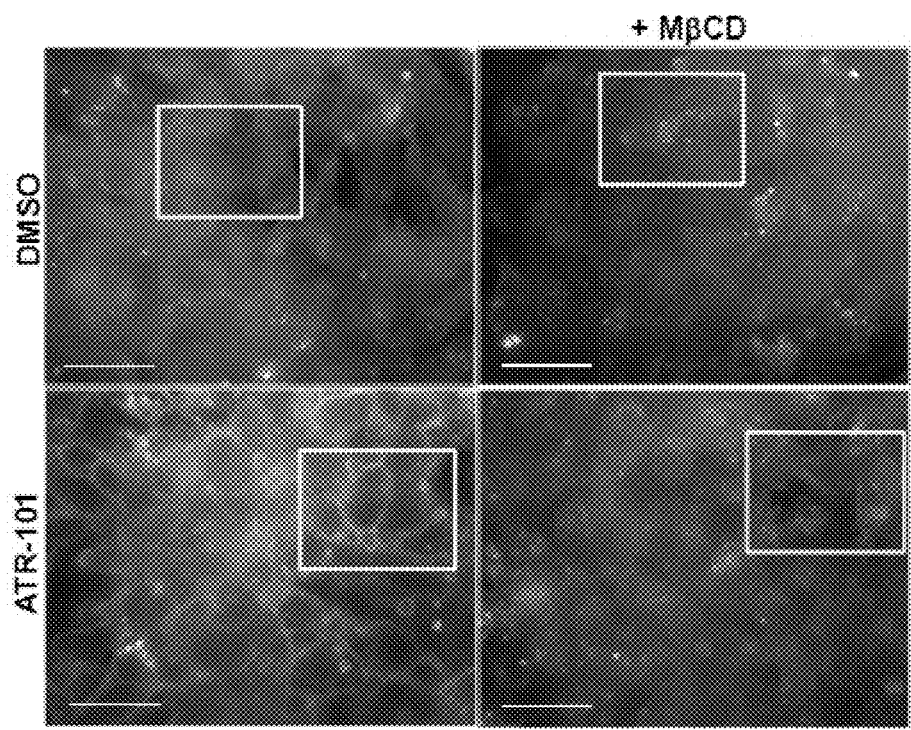
Figure 4K:
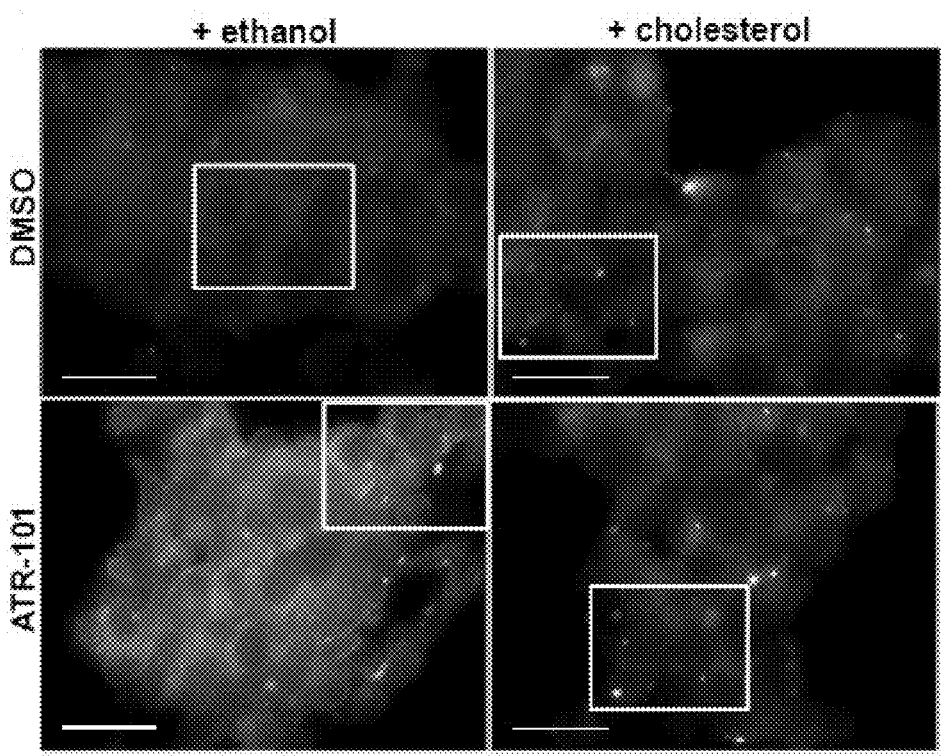

FIG. 4I: Effects of ATR-101 in combination with cholesterol:MβCD on the ATP levels and the caspase 3/7 activities of H295R cells. The cells were cultured with the indicated concentrations of cholesterol:MβCD together with DMSO vehicle or 50 μM ATR-101 for 4 h (upper graphs) or 24 h (lower graphs), followed by measurement of the ATP levels (left graph) and caspase 3/7 activities (right graph). The graphs show the means and the standard deviations of six samples from three experiments. The statistical significance of the differences in ATP levels and caspase 3/7 activities in cells that were cultured with each concentration of cholesterol:MβCD were evaluated by using two-way analysis of variance followed by Dunnett's post hoc tests (cells cultured with cholesterol:MβCD vs. corresponding controls, *P<0.05).

Moderate cholesterol:MβCD concentrations (≤0.5 mM) reduced ATP depletion by ATR-101 at 4 h and 24 h after addition to H295R cells, consistent with the reduction in ATR-101 dependent ATP depletion by exogenous cholesterol (FIG. 3C). The highest cholesterol:MβCD concentrations (≥1 mM) reduced ATP depletion by ATR-101 after 4 h, but they caused ATP depletion both alone and in combination with ATR-101 after 24 h. Cholesterol:MβCD increased the caspase 3/7 activity both alone and in combination with ATR-101 both at 4 h and at 24 h after addition to H295R cells. Cholesterol:MβCD therefore had effects in combination with ATR-101 that were distinct from the effects of MβCD and of exogenous cholesterol separately. The differences between these effects are likely to be due to the distinct activities of the low concentrations of exogenous cholesterol alone and the high concentrations of cholesterol complexed with MβCD FIG. 4J: The full fields from which the images in FIG. 3A (white rectangles) were taken. The scale bars denote 30 μm. H295R cells that were cultured with ATR-101 have higher levels of filipin III binding to the plasma membrane than control cells. Cells that were cultured with ATR-101 together with MβCD did not have a higher level of filipin III binding to the plasma membrane.

FIG. 4K: The full fields from which the images shown in FIG. 3C (white rectangles) were taken. The scale bars denote 30 μm. H295R cells that were cultured with ATR-101 have higher levels of filipin III binding to the plasma membrane than control cells. Cells that were cultured with ATR-101 together with exogenous cholesterol did not have a higher level of filipin III binding to the plasma membrane.

Effects of ATR-101 on cortisol efflux and on doxorubicin accumulation.

Figure 5A:
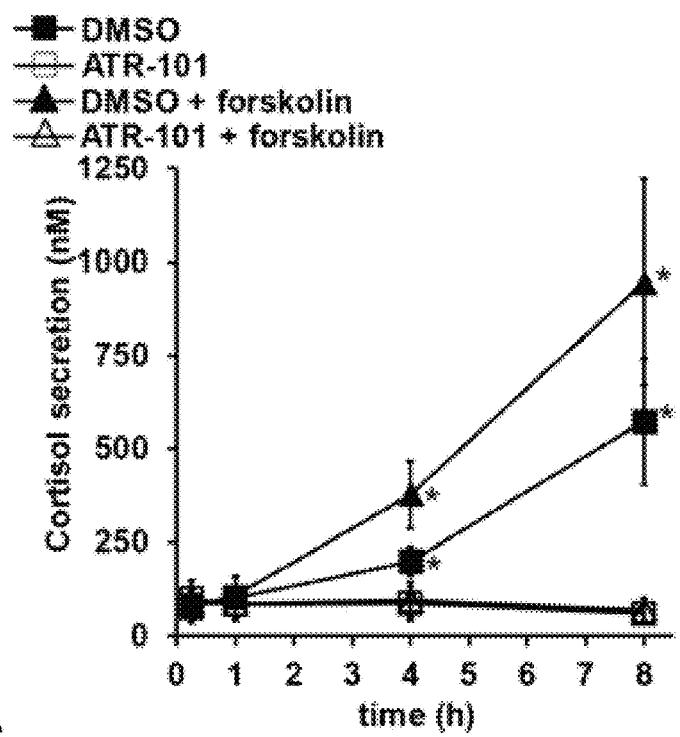

FIG. 5A. Effects of ATR-101 on the rate of cortisol secretion from H295R cells cultured with or without forskolin. The medium of the cells was replaced with media containing DMSO vehicle or 100 μM ATR-101 alone, or together with 100 μM forskolin. The cortisol levels in the media were measured at the times indicated. The graph shows the means and the standard deviations of five samples from two experiments. The statistical significance of the differences in the cortisol concentrations in the medium of cells that were cultured in the absence and in the presence of ATR-101 for the indicated times were evaluated by using two-way analysis of variance followed by Sidak's post hoc tests (cells cultured with DMSO vs. cells cultured with ATR-101, *P<0.05).

Figure 5B:
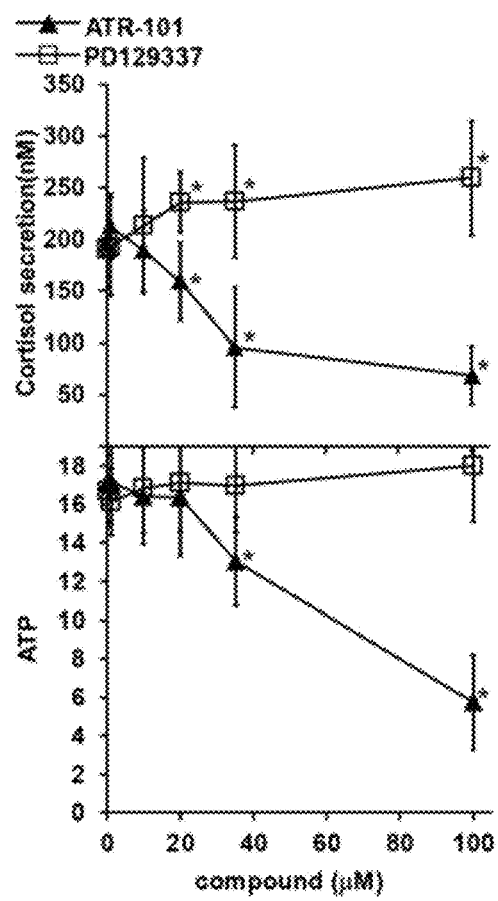

FIG. 5B: Effects of ATR-101 and of PD129337 on cortisol secretion and on ATP levels. The medium of H295R cells was replaced with media containing the indicated concentrations of ATR-101 or PD129337, and the levels of cortisol in the media (upper graph) and of ATP in the cells (lower graph) were measured in the same cultures after 4 h. The graphs show the means and the standard deviations of six samples from two experiments and five samples from two experiments for the cortisol secretion and ATP assays, respectively. The statistical significance of the differences in the cortisol concentrations in the medium and the ATP levels in the cells that were cultured with the indicated concentrations of the compounds were evaluated by using two-way analysis of variance followed by Sidak's post hoc tests (ATR-101 or PD129337 vs. DMSO control, *P<0.05).

Figure 5C:
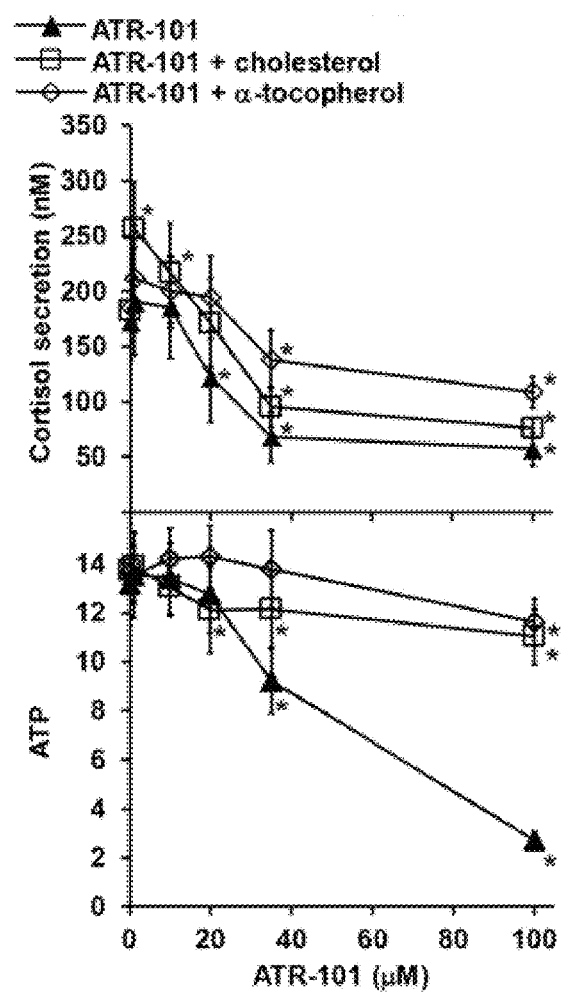

FIG. 5C: Effects of ATR-101 in combination with exogenous cholesterol or α-tocopherol on cortisol secretion and ATP depletion. The medium of H295R cells was replaced with media containing the indicated concentrations of ATR-101 together with vehicle, 40 μM exogenous cholesterol, or 40 μM α-tocopherol. The levels of cortisol in the media (upper graph) and of ATP in the cells (lower graph) were measured in the same cultures after 4 h. The graphs show the means and the standard deviations of six samples from two experiments. The statistical significance of the differences in the cortisol concentrations in the medium and the ATP levels in the cells that were cultured with each concentration of ATR-101 alone or in combination with cholesterol or α-tocopherol were evaluated by using one-way analysis of variance followed by Dunnett's post hoc tests (cells cultured with ATR-101 vs. corresponding controls without ATR-101, *P<0.05).

Figure 5D:
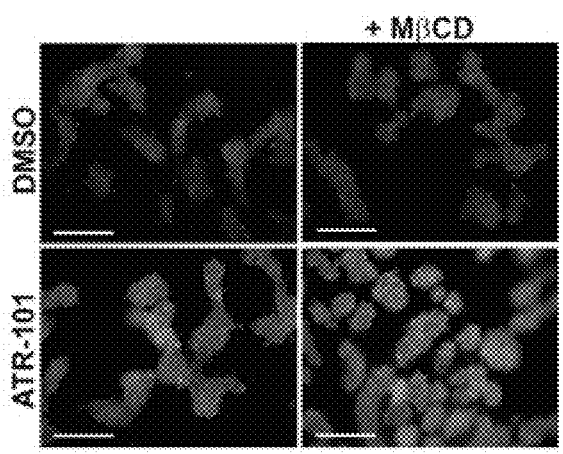

FIG. 5D: Effects of ATR-101 and MβCD separately and in combination on doxorubicin accumulation in H295R cells. The cells were cultured in the presence of 25 µM doxorubicin together with DMSO vehicle (upper images) or 100 µM ATR-101 (lower images) alone (left images) or in combination with 4 mM MβCD (right images). The levels of doxorubicin in the cells were imaged by fluorescence microscopy after 2 h. The images show doxorubicin fluorescence and are representative of images from two separate experiments. The scale bars denote 200 µm.

Effects of ATR-101 on cholesterol trafficking and efflux.

Figure 6A:
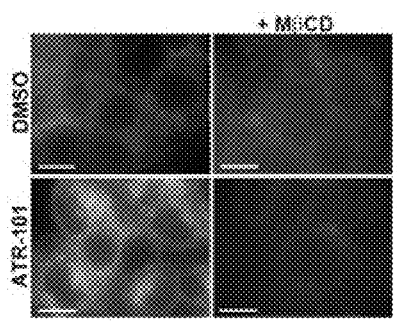

FIG. 6A: Effects of ATR-101 and MβCD separately and in combination on the cholesterol levels in H295R cells that were cultured for 4 h in serum-free medium. The medium of cells that were cultured under standard conditions was replaced with serum-free media containing apoA-I with either DMSO vehicle (upper images) or 100 µM ATR-101 (lower images), alone (left images) or in combination with of 4 mM MβCD (right images). The images show filipin III binding to cholesterol, and are representative of two separate experiments. The full fields from which the images were cropped are shown in Figure S3B. The scale bars denote 10 µm.

Figure 6B:
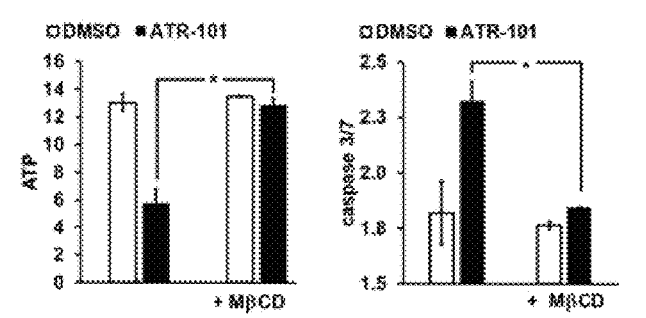

FIG. 6B: Effects of MβCD on ATP depletion and caspase 3/7 activation by ATR-101 in H295R cells that were cultured in serum-free medium. The cells were cultured as described in part A and the ATP levels and caspase 3/7 activities were measured. The graphs show the means and the standard deviations of eight samples from four experiments and six samples from three experiments for the ATP and caspase 3/7 assays, respectively. The statistical significance of the differences in ATP levels and the caspase 3/7 activities in cells that were cultured with ATR-101 in the presence or the absence of MβCD were evaluated by using unpaired two-tailed Student's t-tests (cells cultured with MβCD vs. corresponding controls, $*P<0.05$).

Figure 6C:
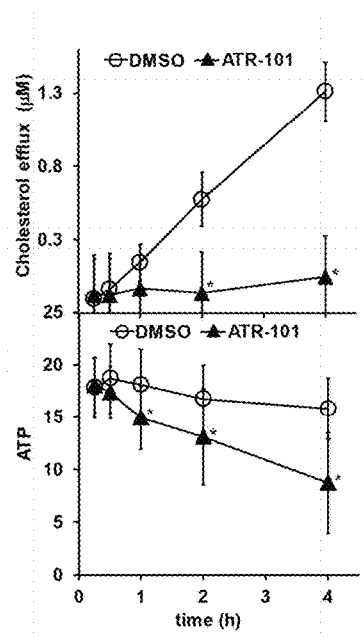

FIG. 6C: Effects of ATR-101 on the rates of cholesterol efflux and on the ATP levels of H295R cells during culture in serum-free medium. The medium of cells that were cultured under standard conditions was replaced with serum-free medium containing apoA-I with DMSO vehicle or 100 µM ATR-101. At the indicated times, the cholesterol level in the medium (upper graph) and the ATP level in the cells (lower graph) were measured. The graphs show the means and standard deviations of six samples from two experiments. The statistical significance of the differences in the cholesterol concentrations in the medium and the ATP levels of cells that were cultured for the indicated times with ATR-101 were evaluated by using two-way analysis of variance followed by Sidak's post hoc tests (ATR-101 vs. DMSO control, $*P<0.05$).

Figure 6D:
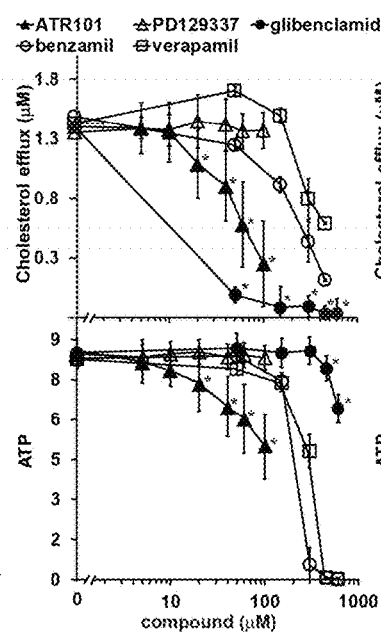

FIG. 6D: Effects of ATR-101 and of ABC transporter inhibitors on cholesterol efflux and on the ATP levels of H295R cells during culture in serum-free medium. The levels of cholesterol in the medium (upper graph) and of cellular ATP (lower graph) were measured in the same cultures 4 h after replacing the standard culture medium with serum-free media containing apoA-I and the indicated concentrations of ATR-101, PD129337, glibenclamide, benzamil, or verapamil. The graphs show the means and standard deviations of six samples from three experiments for cells cultured with ATR-101, PD129337, or glibenclamide and two samples from one experiment for cells cultured with benzamil or verapamil. The statistical significance of the differences in cholesterol concentrations in the medium and the ATP levels of cells that were cultured with the indicated concentrations of ATR-101, PD129337, or glibenclamide were evaluated by using one-way analysis of variance followed by Dunnett's post hoc tests (cells cultured with ABC inhibitors vs. cells cultured with DMSO, $*P<0.05$).

Figure 6E:
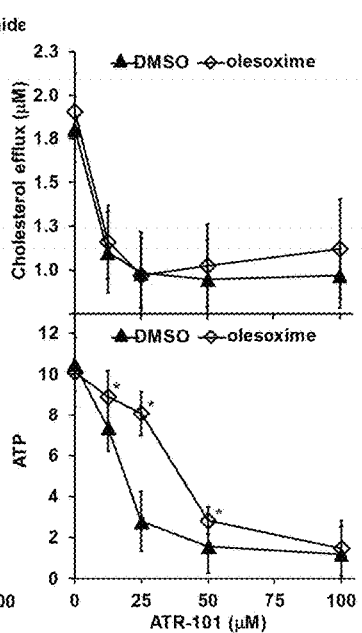

FIG. 6E: Effects of ATR-101 in combination with olesoxime on cholesterol efflux and on the ATP levels in H295R cells. The cells were cultured with the indicated concentrations of ATR-101 alone or ATR-101 in combination with 40 µM olesoxime for 4 h. The media were replaced with serum-free medium containing apoA-I, and the levels of cholesterol in the medium (upper graph) and of cellular ATP (lower graph) were measured after incubation for an additional 4 h. The graphs show the means and standard deviations of six samples from two experiments and nine samples from three experiments for the cholesterol efflux and ATP assays, respectively. The statistical significance of the differences in cholesterol concentrations in the medium and the ATP levels of cells that were cultured with ATR-101 in the presence versus the absence of olesoxime were evaluated using two-way analysis of variance followed by Sidak's post hoc tests (cells cultured with AT-101 and olesoxime vs. corresponding controls without olesoxime $*P<0.05$).

Combined effects of ABC transporter inhibitors with each other and with ATR-101 on the ATP levels of H295R cells.

Figure 7A:
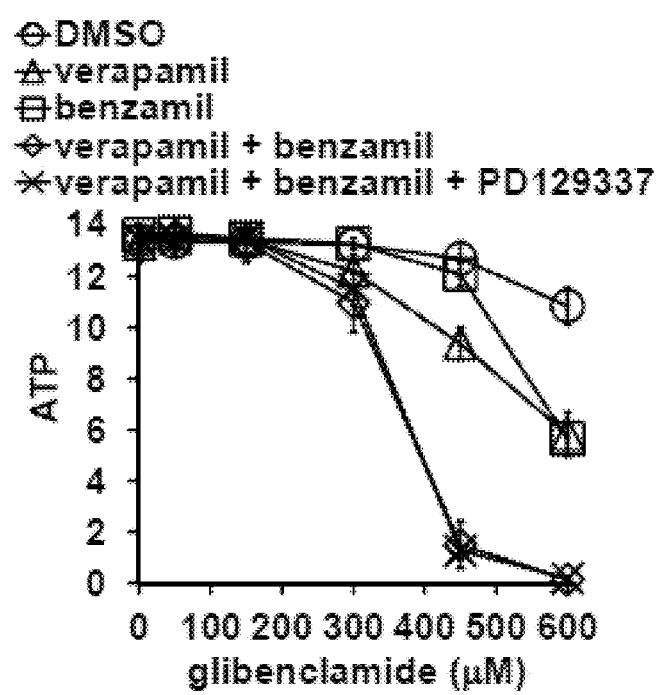

FIG. 7A: Effects of different combinations of ABC transporter inhibitors on the ATP level of H295R cells. The cells were cultured with the indicated concentrations of glibenclamide in combination with DMSO vehicle or with verapamil (50 µM), benzamil (50 µM), and PD129337 (1 µM). The ATP levels of the cells were measured 4 h after addition of the compounds. The data show the means and standard deviations of two cultures of cells with each concentration of each combination of inhibitors, and are representative of the results from two experiments.

Inhibitors of ABCA1, ABCG1 and MDR1 had a synergistic effect on ATP depletion in H295R cells. ATP depletion by these ABC inhibitors was not enhanced by ACAT inhibition.

Figure 7B:
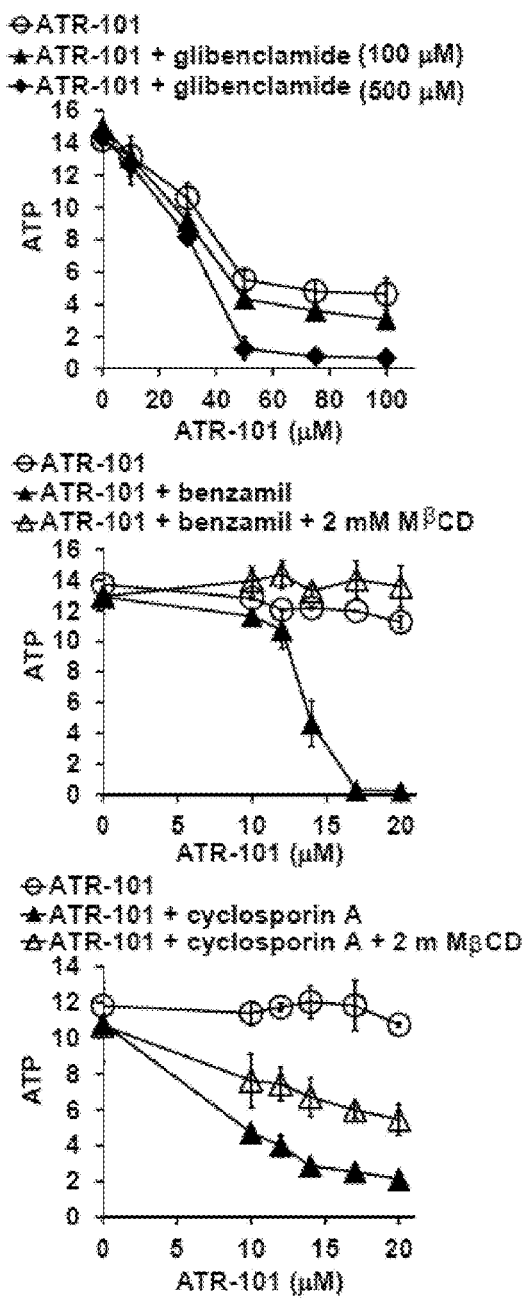
Figure 7B:
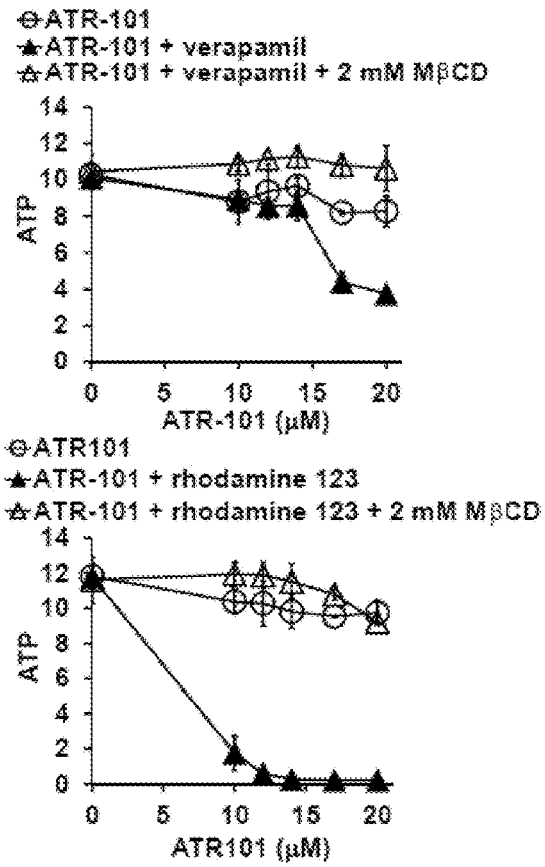

FIG. 7B: Effects of ATR-101 in combination with selective ABC transporter inhibitors on H295R cells. H295R cells were cultured with the indicated concentrations of ATR-101 together with DMSO vehicle, glibenclamide (100 µM or 500 µM), benzamil, rhodamine 123, or cyclosporine A (20 µM each), in the absence and in the presence of 2 mM MβCD. The ATP levels of the cells were measured after 4 h. The graphs show the means and the standard deviations of two cultures of cells with each concentration of each combination of inhibitors, and are representative of the results from two experiments. The data for the graphs shown with different ABC transporter inhibitors were obtained in separate experiments.

ATR-101 in combination with ABCG1 (benzamil) and MDR1 (cyclosporine A, verapamil) inhibitors caused larger than additive reductions in the ATP levels of cells. ATR-101 in combination with an ABCA1 inhibitor (glibenclamide) did not cause a larger than additive reduction in the ATP levels of cells. The combined effects of ATR-101 with selected ABC transporter inhibitors on ATP depletion were suppressed by MβCD, indicating that the combined cytotoxicity required cholesterol accumulation. ATR-101 in combination with the mitochondrial inhibitor and MDR1 substrate rhodamine-123 also caused larger than additive reductions in the ATP levels of cells. These result suggest that the potency of ATR-101 was enhanced when it was used in combination with inhibitors of ABCG1, MDR1, or mitochondrial functions.

Figure 7C:
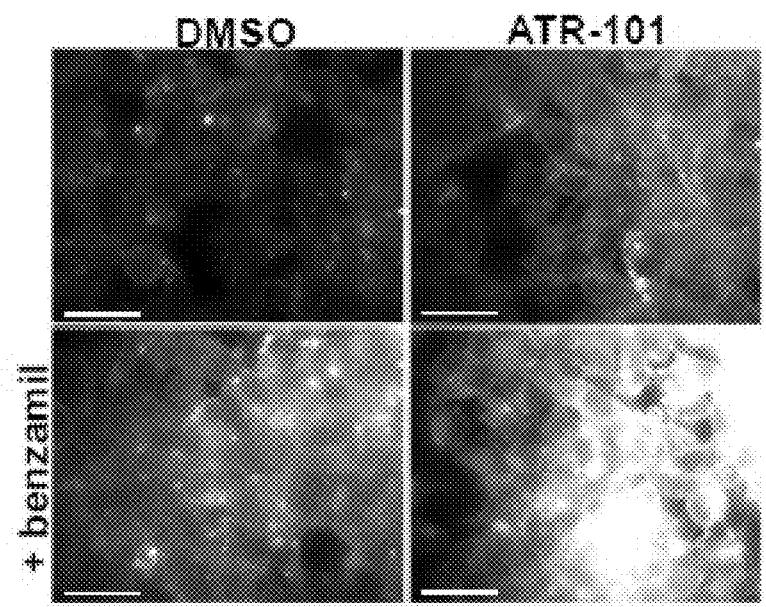

FIG. 7C: Effects of ATR-101 and benzamil on the cholesterol level of H295R cells. The cells were cultured with DMSO vehicle or 20 µM ATR-101 and 5 µM benzamil, separately and in combination for 1 h. The cells were fixed and the cholesterol was visualized using filipin III. The images show filipin III fluorescence captured with a 60× oil objective and are representative of two independent experiments. The scale bars denote 30 μm.

Benzamil and ATR-101 in combination caused a larger than additive increase in cholesterol accumulation.

Effects of MDR1 inhibitors on cortisol secretion and on doxorubicin accumulation.

Figure 8A:
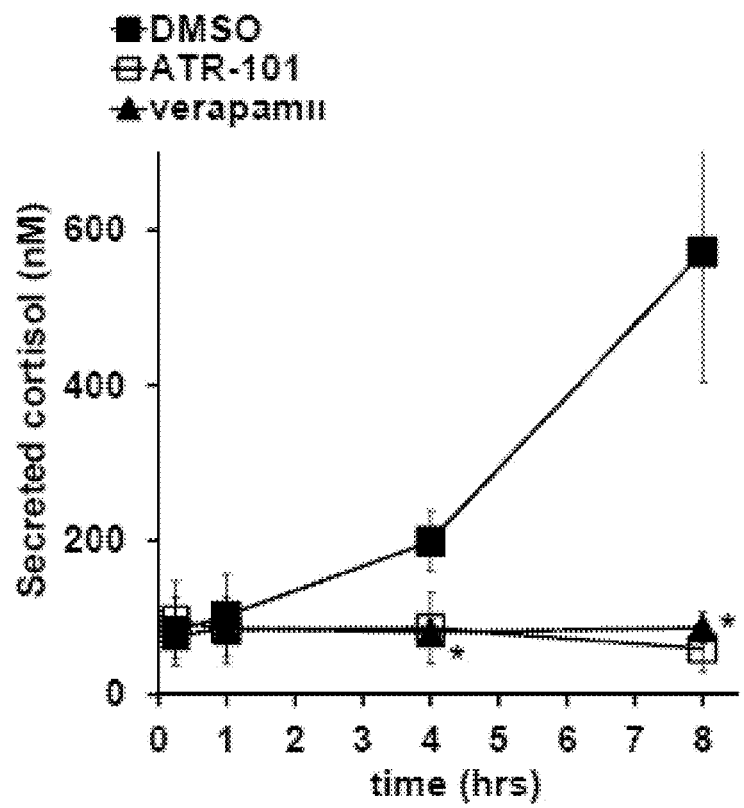

FIG. 8A: Comparison of the effects of ATR-101 and verapamil on cortisol secretion. The cells were switched to media with DMSO vehicle, 100 μM ATR-101, or 100 μM verapamil. The levels of cortisol secreted into the media were measured at the indicated times. The graph shows the means and the standard deviations of five samples from two experiments. The statistical significance of the differences in the cortisol concentrations in the medium at each time after verapamil addition were evaluated by using two-way analysis of variance followed by Sidak's post hoc tests (verapamil vs. DMSO controls, *$P<0.05$).

ATR-101 and verapamil inhibited cortisol secretion from H295R cells with similar efficiencies. The inhibition of cortisol secretion by verapamil suggests that MDR1 is required for the cortisol secretion that is detected in the ACC-derived cells. Cortisol secretion from H295R cells was increased by forskolin, consistent with the induction of corticosteroid biosynthesis by cAMP signaling (see, e.g., Rainey, et al., 1993 J Clin Endocrinol Metab, 77, 731-7).

FIG. 8B: Comparison of the effects of zosuquidar, ATR-101, and ATR-101 together with olesoxime on cortisol secretion and on the ATP levels of H295R cells. The cells were switched to media containing indicated concentrations of zosuquidar, ATR-101, or ATR-101 together with 40 μM olesoxime. The levels of cortisol secreted into the media (upper graph) and the cellular ATP levels (bottom graph) were measured after 4 h. The graphs show the means and the standard deviations of five samples from two experiments. The statistical significance of the differences in the cortisol concentrations in the medium and the ATP levels in the cells that were cultured with the indicated concentrations of the compounds were evaluated by using one-way analysis of variance followed by Dunnett's post hoc tests (clls cultured with ATR-101 or zosuquidar vs. corresponding controls, *$P<0.05$).

Zosuquidar inhibited cortisol secretion from H295R cells. Zosuquidar selectively inhibits MDR1 and does not inhibit the closely related MRP1, MRP2, or BCRP ABC transporters (see, e.g., Shepard, et al., 2003 Int J Cancer, 103, 121-5). An 8-fold higher concentration of of zosuquidar did not cause ATP depletion. MDR1 inhibition was therefore not sufficient for ATP depletion. Perturbations to mitochondrial functions can affect steroidogenesis and cholesterol efflux (see, e.g., Graham, et al., 2015 Free Radic Biol Med, 89, 982-92; Midzak, et al., 2011 Biol Reprod, 84, 976-85). ATR-101 inhibited cholesterol efflux (FIG. 6E) and cortisol secretion (FIG. 8B) in the absence and in the presence of the mitoprotective compound olesoxime (see, e.g., Bordet, et al., 2010 Pharmaceuticals (Basel), 3, 345-368) to the same extent. Olesoxime reduced ATP depletion by ATR-101 (FIG. 6E, 8B). ATR-101 therefore inhibited cholesterol efflux and cortisol secretion by mechanisms that did not require full ATP depletion.

FIG. 8C: Effects of different ABC transporter inhibitors on doxorubicin accumulation in H295R cells. The cells were cultured in the presence of 25 μM doxorubicin together with DMSO vehicle, 20 μM benzamil, 20 μM verapamil, or 20 μM ATR-101. The levels of doxorubicin in the cells were imaged after 2 h by fluorescence microscopy using a 20× objective. The images show doxorubicin fluorescence and are representative of images from two independent experiments. The scale bars denote 100 μm.

A low level of doxorubicin fluorescence was detected in H295R cells that were cultured with doxorubicin in the absence of MDR1 inhibitors. ATR-101 and verapamil increased doxorubicin accumulation suggesting that they inhibited MDR1 activity. Benzamil did not increase doxorubicin accumulation, consistent with the export of doxorubicin primarily by MDR1 and the lack of MDR1 inhibition by benzamil.

Effects of ATR-101 and ABC Transporter Inhibitors on the Cholesterol Levels of H295R Cells that Were Cultured in Serum Free Medium for 4 h.

Figure 9A:
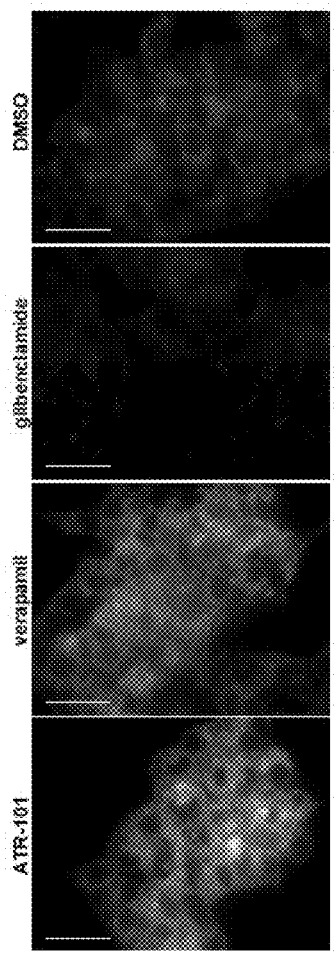

FIG. 9A: Comparison of the effects of glibenclamide, verapamil, and ATR-101 on the cholesterol levels in H295R cells that were cultured in serum-free medium. The medium of cells that were cultured under standard conditions was replaced with serum-free media containing apoA-I with either DMSO vehicle, 50 μM glibenclamide, 50 μM verapamil, or 50 μM ATR-101 for 4 h. The cholesterol in the cells was visualized by filipin III binding. The images show filipin III fluorescence and are representative of two independent experiments. The scale bars denote 30 μm.

Verapamil and ATR-101 but not glibenclamide increased the level of cholesterol in intracellular membranes of H295R cells that were cultured in serum-free medium. The lack of cholesterol accumulation in cells that were cultured with glibenclamide indicates that the inhibition of cholesterol efflux was not sufficient to cause cholesterol accumulation in H295R cells. The increase in cholesterol in cells that were cultured with verapamil indicates that the inhibition of cholesterol efflux was not necessary for cholesterol accumulation. The increase in cholesterol efflux caused by verapamil under these same conditions is an independent indicator of the increase in intracellular cholesterol caused by verapamil (FIG. 6D). The increase in cholesterol efflux caused by verapamil likely represents a compensatory mechanism in response to MDR1 inhibition by verapamil.

Figure 9B:
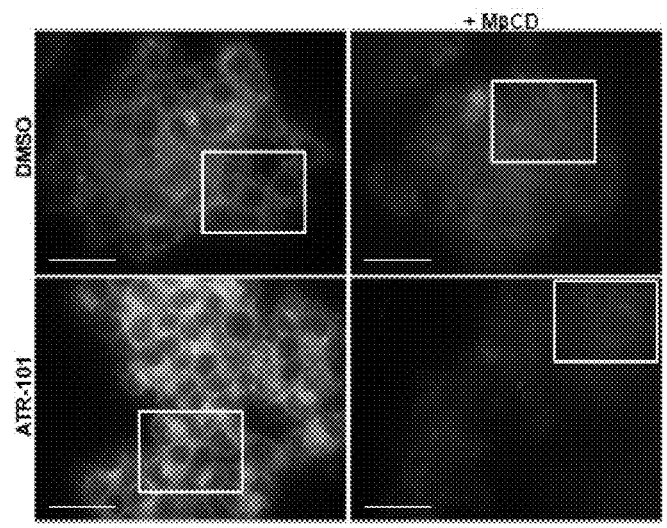

FIG. 9B: The full fields from which the images in FIG. 6A (white rectangles) were taken. The scale bars denote 30 μm.

ATR-101 increased the cholesterol levels in H295R cells that were cultured in serum-free medium. MβCD suppressed the cholesterol accumulation that was caused by ATR-101 in serum-free medium. MβCD also reduced the basal level of cholesterol in H295R cells that were cultured in serum-free medium.

The rate of cholesterol efflux in the absence of ATR-101 corresponded to 5% of the total amount of cholesterol and cholesterol esters per hour in H295R cells. The inhibition of cholesterol efflux alone was therefore unlikely to account for the accumulation of cholesterol in cells that were cultured with ATR-101. Additional activities of ATR-101 likely contributed to cholesterol accumulation and cytotoxicity.

Figure 9C:
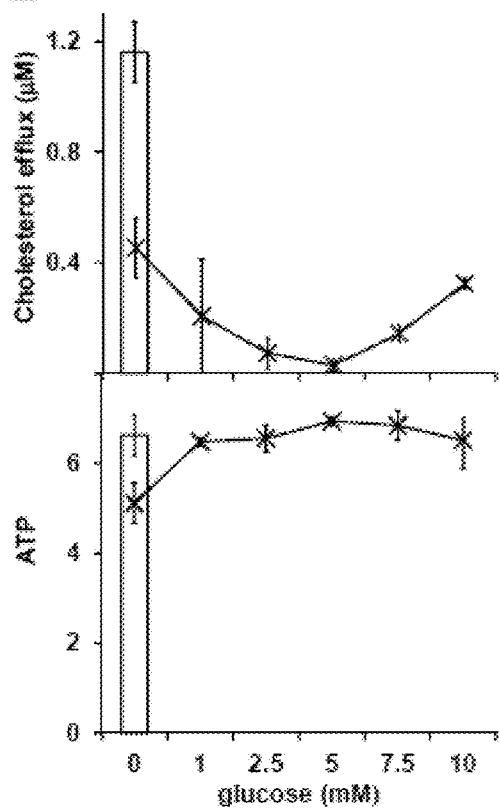
Figure 9C:
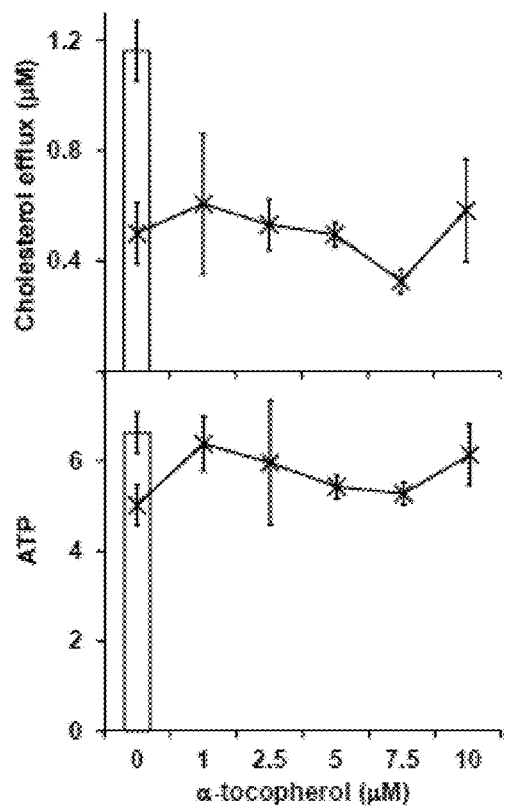

FIG. 9C: Effects of glucose and α-tocopherol on cholesterol efflux versus ATP levels in H295R cultured with ATR-101. The levels of cholesterol in the medium (upper graphs) and of cellular ATP (lower graphs) were measured in the same cultures 4 h after replacing the standard culture medium with serum-free media containing apoA-I and DMSO vehicle (white bars) or 100 μM ATR-101 (line graphs) and the indicated concentrations of glucose (left) or α-tocopherol (right).

ATR-101 inhibited cholesterol efflux under conditions in which ATP levels were restored by either glucose or α-tocopherol.

Combined effects of ABC transporter inhibitors and of ATR-101 on ATP levels, caspase 3/7 activities and cholesterol levels in H295R cells.

Figure 10A:
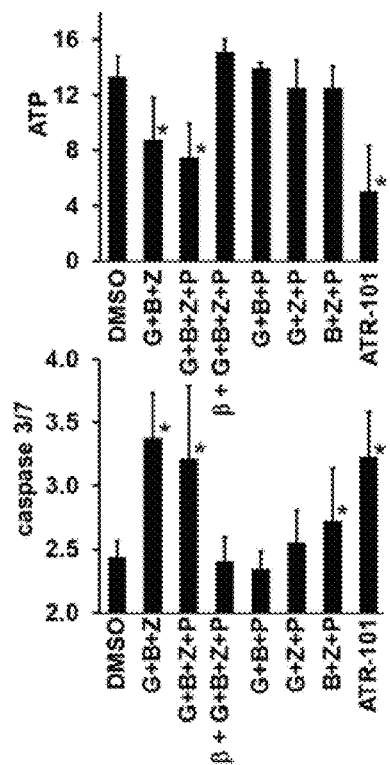

FIG. 10A: Effects of different combinations of ABC transporter inhibitors on the ATP level and on the caspase 3/7 activity of H295R cells. The cells were cultured in serum-free media containing 50 µM each of the indicated combinations of glibenclamide (G), benzamil (B) and zosuquidar (Z), 10 µM PD129337 (P), and 4 mM MβCD (β). The ATP levels (upper graph) and caspase 3/7 activities (lower graph) were measured in parallel cultures. The graphs show the means and the standard deviations of six samples from three experiments. The statistical significance of the differences in ATP levels and caspase 3/7 activities of cells that were cultured with different combinations of ABC inhibitors were evaluated by using one-way analysis of variance followed by Dunnett's post hoc tests (cells cultured with ABC inhibitors vs. cells cultured with DMSO, *P<0.05).

Figure 10B:
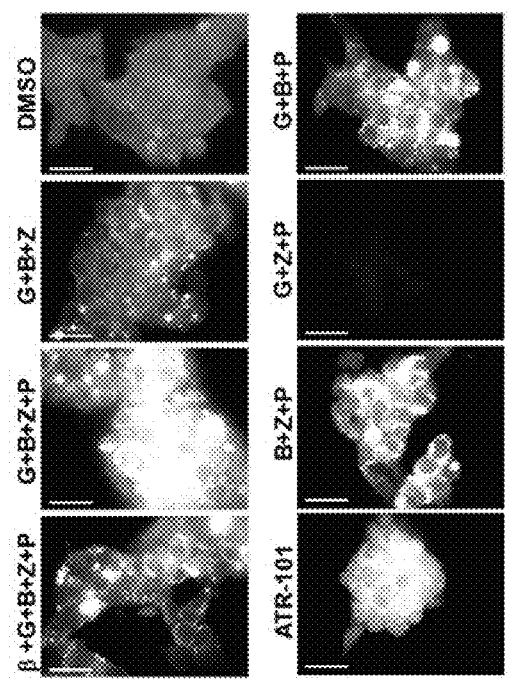

FIG. 10B: The cholesterol levels of H295R cells that were cultured as described in panel A were visualized by filipin III binding. The scale bars denote 30 µm.

Figure 10C:
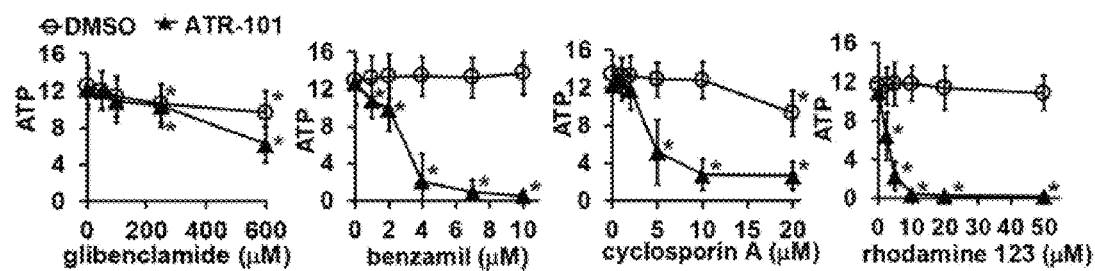

FIG. 10C: Effects of ATR-101 in combination with glibenclamide, benzamil, cyclosporine A, or rhodamine 123 on the ATP levels of H295R cells. H295R cells were cultured with DMSO vehicle or 20 µM ATR-101 together with the indicated concentrations of glibenclamide, benzamil, cyclosporin A, or rhodamine 123. The ATP levels were measured 4 h after addition of each compound, and were obtained in separate experiments. The graphs show the means and standard deviations of six samples from three experiments. The statistical significance of the differences in the ATP levels of cells that were cultured with each concentration of the ABC inhibitors or substrate alone or in combination with ATR-101 were evaluated by using one-way analysis of variance followed by Dunnett's post hoc tests (cells cultures with glibenclamide, benzamil, cyclosporine A, or rhodamine 123 vs. corresponding controls, *P<0.05).

Effects of steroids and inhibitors of steroidogenesis on ATR-101 cytotoxicity.

Figure 11A:
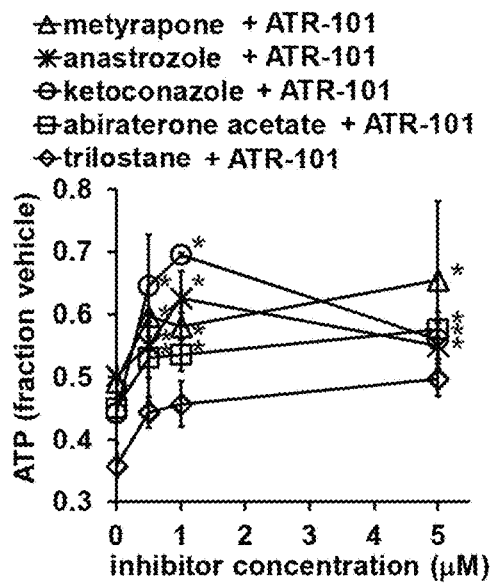

FIG. 11A: Effects of inhibitors of steroidogenic enzymes on ATP depletion by ATR-101 in H295R cells. The cells were cultured with 35 µM ATR-101 or DMSO vehicle together with different concentrations the indicated inhibitors of steroidogenesis. The ATP levels of the cells were measured after 4 h, and the ratio of the ATP levels in cells cultured with each concentration of each inhibitor together with ATR-101 versus cells that were cultured with DMSO vehicle was calculated. The graph shows the means and the standard deviations of the ratios between the ATP levels of two pairs of cells cultures for each concentration of each inhibitor of steroidogenesis. The statistical significance of the differences in the ATP level ratios were evaluated by using two-way analysis of variance followed by Sidak's post hoc tests (cells that were cultured with each inhibitor of steroidogenesis in combination with ATR-101 vs. cells cultured with ATR-101 alone, n=10, *P<0.05). The data prior to normalization are shown in FIG. 14.

Figure 11B:
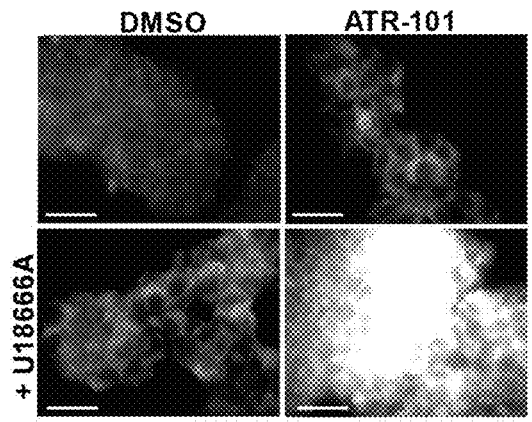

FIG. 11B: Effects of ATR-101 and U18666A on the cholesterol levels in H295R cells. The cells were cultured with 20 µM ATR-101 and 8 µM U18666A, separately and in combination in serum-free medium. The images show filipin III binding to cholesterol, and are representative of two separate experiments. The scale bars denote 30 µm.

Figure 11C:
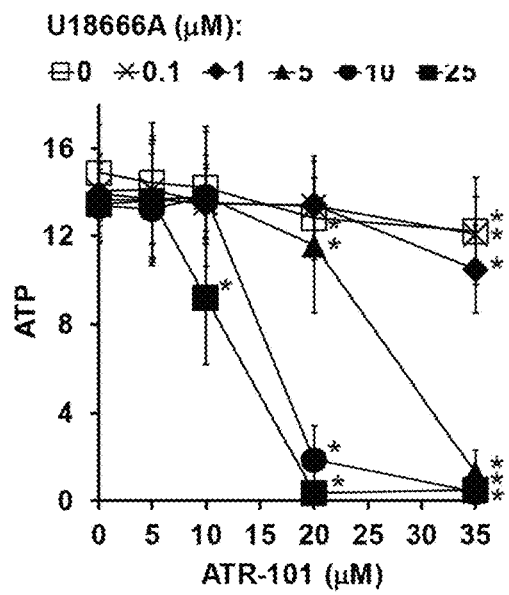

FIG. 11C: Combined effects of ATR-101 and U18666A on the ATP level of H295R cells. The cells were cultured with DMSO vehicle or the indicated concentrations of U18666A and ATR-101 in serum-free medium for 4 h and the ATP levels were measured. The graph shows the means and standard deviations of six samples from three experiments. The statistical significance of the differences in the ATP levels of cells that were cultured with ATR-101 together with each U18666A concentration were evaluated by using two-way analysis of variance followed by Dunnett's post hoc tests (ATR-101 with U18666A vs. U18666A alone, *P<0.05).

Figure 11D:
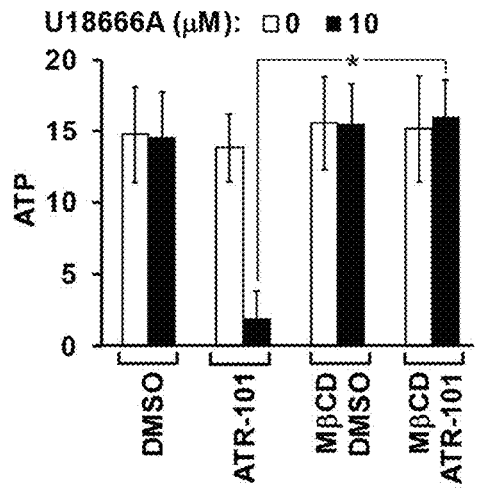

FIG. 11D: Effects of MβCD on ATP depletion by the combined effects of ATR-101 together with U18666A. The cells were cultured with 20 µM ATR-101 and 10 µM U18666A, separately and in combination, in the absence and in the presence of 2 mM MβCD in serum-free medium. The graphs show the means and the standard deviations of six samples from three experiments. The statistical significance of the differences in ATP levels of cells that were cultured with ATR-101 and U18666A with or without MβCD was evaluated using unpaired two-tailed Student's t-tests (cells cultured with ATR-101 and/or U18666A together with MβCD vs. corresponding controls without MβCD, *P<0.05).

ATR-101 effects on the transcription of genes that affect cholesterol and steroid levels.

FIG. 12A: Effects of ATR-101 on ABCA1, ABCG1, IDOL and CHOP transcript levels. The levels of the transcripts indicated in each graph were measured in cells that were cultured with the indicated concentrations of ATR-101 for 1 h. The transcript levels were normalized by the RPL9 transcript levels. The graphs show the means and the standard deviations of five samples from four experiments. The statistical significance of the differences in transcript levels of cells that were cultured with each concentration of ATR-101 were evaluated by using one-way analysis of variance followed by Dunnett's post hoc tests (cells cultured with ATR-101 vs. cells cultured with DMSO, *P<0.05).

FIG. 12B: Effects of ATR-101 on steroidogenic gene transcription. The levels of the transcripts indicated in each graph were measured in cells that were cultured for the times indicated at the bottom of the figure with the concentrations of ATR-101 indicated by the symbols shown at the top of the figure. The transcript levels were normalized by the RPL9 transcript levels. The graphs show the means and the standard deviations of two samples from two experiments. The statistical significance of the differences in transcript levels of cells that were cultured with each concentration of ATR-101 were evaluated by using one-way analysis of variance followed by Dunnett's post hoc tests (all samples with ATR-101 vs. all samples without ATR-101, n=8, *P<0.05).

Effects of ATR-101 vs. PD129337 on transcript levels.

Figure 13A:
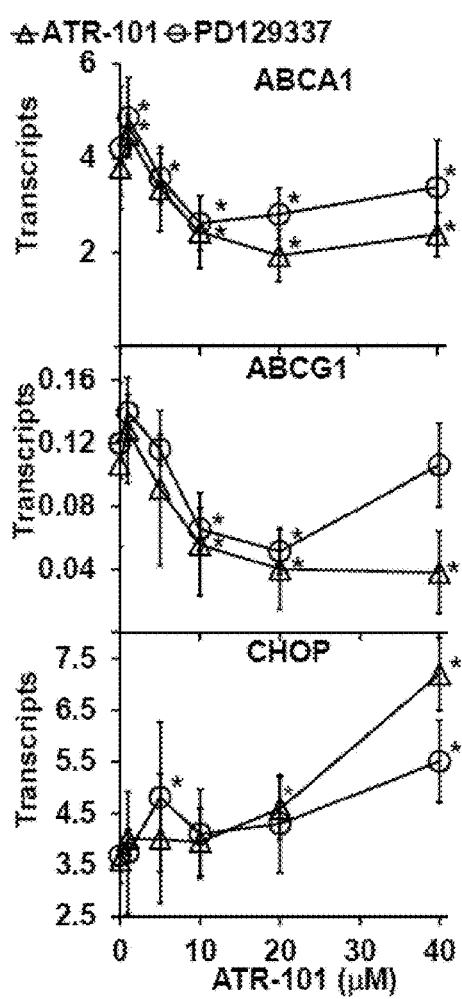

FIG. 13A: Comparison of the effects of ATR-101 and PD129337 on transcription of ABCA1, ABCG1 and CHOP. The levels of the transcripts indicated in each graph are plotted in cells that were cultured with the concentrations of ATR-101 or PD129337 indicated at the bottom of the figure for 4 h. The transcript levels were normalized by the RPL9 transcript levels. The graphs show the means and the standard deviations of five samples from four experiments. The statistical significance of the differences in transcript levels in cells that were cultured with each concentration of ATR-101 or PD129337 were evaluated by one-way analysis of variance followed by Dunnett's post hoc tests (cells cultured with ATR-101 or PD129337 vs. cells cultured with DMSO, *P<0.05).

ATR-101 and PD129337 inhibited liver X receptor target genes (ABCA1 and ABCG1) and activated the ER-stress response gene (CHOP) within 4 h after drug exposure. The effects of PD129337 on these transcripts levels indicate that they are not a result of cytotoxicity.

Figure 13B:
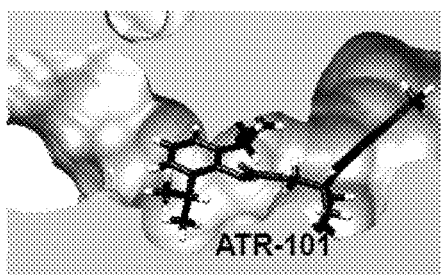

FIG. 13B: Model for ATR-101 binding to LXRa. A web-based docking program (see, e.g., Grosdidier, et al., 2007 Proteins, 67, 1010-25) was used to simulate ATR-101 binding to LXRa (PDB ID: 1UHL).

The LXRα ligand binding pocket is displayed in surface area representation. ATR-101 is displayed in stick representation. The ATR-101 docking shown is representative of 24 dockings inside of the ligand binding pocket out of a total of 256 dockings.

Effects of inhibitors of steroidogenesis on ATR-101 cytotoxicity.

Figure 14A:
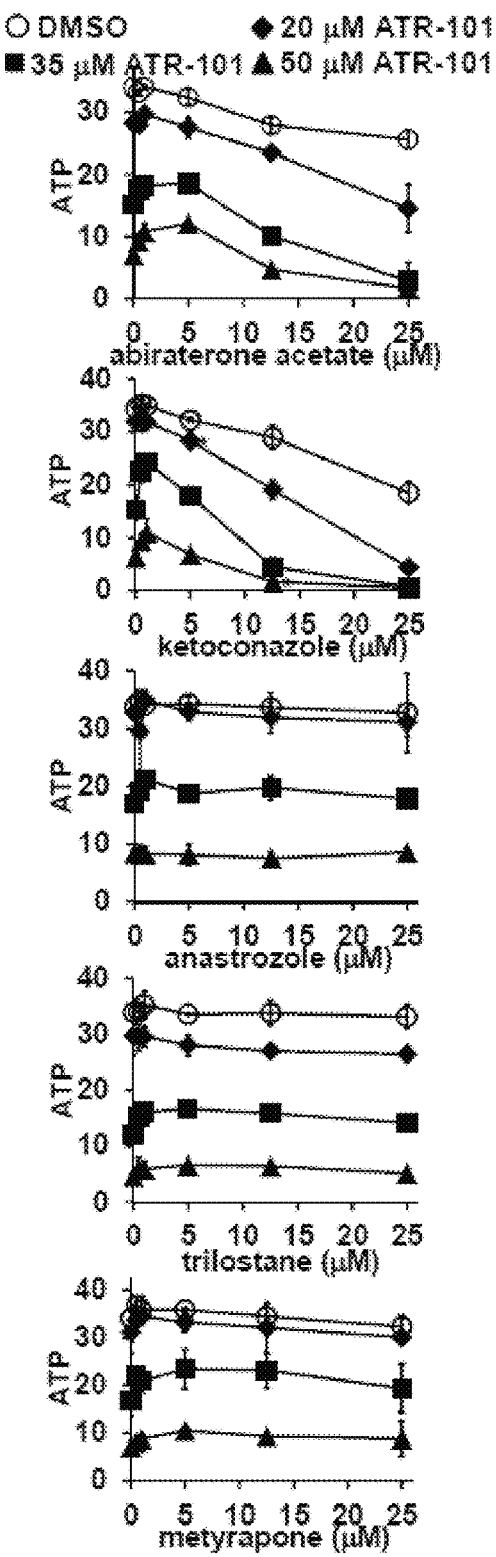
Figure 14B:
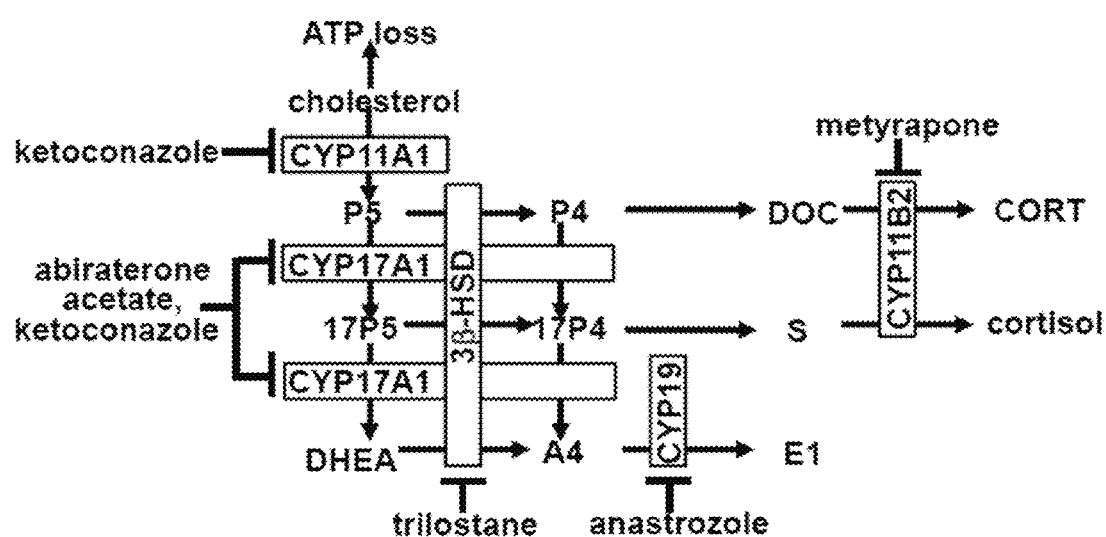

FIG. 14A and FIG. 14B: Effects of inhibitors of steroidogenesis on ATP depletion by ATR-101. H295R cells were cultured with DMSO vehicle or the indicated concentrations of ATR-101 together with the indicated concentrations of abiraterone acetate, ketoconazole, anastrozole, trilostane, metyrapone for 4 h and the ATP levels were measured. The graphs show the means and the standard deviations of two cultures of cells with each concentration of each combination of inhibitors shown, and are representative of results from two experiments. The data for the graphs shown were obtained from parallel cultures with all inhibitors.

The diagram on the right shows the principal targets of abiraterone acetate, ketoconazole, anastrozole, trilostane, and metyrapone in the major branches of adrenocortical steroidogenesis. The enzymes are indicated inside the rectangles and the rectangles are superimposed on the reactions (arrows) that they catalyze. Only a subset of the intermediates are shown. Pregnenolone (P5); 17-hydroxypregnenolone (17-OHP), dihydroepiandrostenedione (DHEA), dihydroepiandrostenedione sulfate (DHEAS), progesterone (P4), 17-hydroxyprogesterone (17-OHP4), androstenedione (A4), corticosterone (DOC), 11-deoxycortisol (S), estrone (E1), corticosterone (CORT).

Low concentrations of many different inhibitors of steroidogenesis reduced ATP depletion by ATR-101. The concentrations of the inhibitors that reduced ATP depletion by ATR-101 were consistent with their inhibitory coefficients for different steroidogenic enzymes (see, e.g., Garrido, et al., 2014 J Steroid Biochem Mol Biol, 143, 1-10; Johansson, et al., 1998 Pharmacol Toxicol, 83, 225-30; Takahashi, et al., 1990 J Steroid Biochem Mol Biol, 37, 231-6). High concentrations of some of these inhibitors enhanced ATP depletion both alone and in combinatioin with ATR-101. The concentrations of ketoconazole and abiraterone acetate that enhanced ATP depletion were consistent with the concentrations that inhibit MDR1 (see, e.g., Siegsmund, et al., 1994 J Urol, 151, 485-91; Benoist, et al., 2016 Clin Pharmacokinet, 55, 1369-1380).

Exogenous steroids and synthetic androgen derivatives can influence cholesterol trafficking and metabolism (see, e.g., Butler, et al., 1992 J Biol Chem, 267, 23797-805; Debry, et al., 1997 J Biol Chem, 272, 1026-31; Lange, et al., 1997 J Biol Chem, 272, 17018-22; Midzak et al., 2011 J Biol Chem, 286, 9875-87; Midzak, et al., 2012 Steroids, 77, 1327-34; Liscum and Faust, 1989, J Biol Chem, 264, 11796-806; Hartgens, et al., 2004 Br J Sports Med, 38, 253-9; Garevik, et al., 2012 Subst Abuse Treat Prey Policy, 7, 12; Lucken-Ardjomande, et al., 2008 Cell Death Differ, 15, 484-93). These results suggest that steroid accumulation can contribute to ATR-101 cytotoxicity through the inhibition of cholesterol trafficking.

DETAILED DESCRIPTION OF THE INVENTION

Control of the cholesterol (e.g., unesterified cholesterol) level is essential for cell functions and viability (see, e.g., Maxfield and van Meer, 2001, Curr Opin Cell Biol, 22, 422-9). The cholesterol level of adrenocortical cells is affected by many pathways, some of which are unique to the adrenal cortex. Studies of anti-atherosclerosis agents identified compounds that cause selective degeneration of the adrenal cortex (adrenalytic activity) in several species (see, e.g., Dominick, et al., 1993 Fundam Appl Toxicol, 20, 217-24; Reindel et al., 1994, Toxicol Pathol, 22, 510-8; Sliskovic, et al., 1998 J Med Chem, 41, 682-90; Matsuo, et al., 1996 Toxicol Appl Pharmacol, 140, 387-92; Tanaka, et al., 1998 Journal of Medicinal Chemistry, 41, 4408-4420).

Experiments conducted during the course of developing embodiments for the present invention investigated the adrenalytic compound ATR-101 as a prospective agent for the treatment of adrenocortical carcinoma (ACC) because of its cytotoxicity in ACC-derived cells and its anti-xenograft and adrenalytic activities (see, e.g., Cheng Y, et al., Endocrine-Related Cancer 2016; 23(4):1-19).

ACC is a rare cancer that has few treatment options. The adrenalytic compound mitotane is a first-line drug for ACC treatment despite its poor efficacy, unfavorable pharmacokinetics, severe side effects, and potential drug interactions (see, e.g., Maiter D, et al., Ann Endocrinol (Paris) 2016; 77(5):578-85). Clinical trials of molecularly targeted agents have not demonstrated therapeutic benefit for ACC patients (see, e.g., Creemers S G, et al., Endocr Relat Cancer 2016; 23(1):R43-69). The divergence among the genetic and epigenetic changes in different ACC tumors suggests that many different molecular mechanisms underlie ACC malignancies (see, e.g., Assie G, et al., Nat Genet 2014; 46(6):607-12; Zheng S, et al., Cancer Cell 2016; 29(5):723-36). Adrenalytic compounds can potentially be used for the treatment of ACCs that are caused by different molecular mechanisms.

ATR-101 inhibits the establishment and impedes the growth of ACC cell xenografts in nude mice (see, e.g., Cheng Y, et al., Endocrine-Related Cancer 2016; 23(4):1-19). The inhibition of xenograft growth in animals that are administered ATR-101 correlates with increased apoptosis of xenograft cells. ATR-101 causes mitochondrial dysfunctions in ACC-derived cells and reactive oxygen toxicity in cultured cells and in the zona fasciculata layer of the guinea pig adrenal cortex (see, e.g., Cheng Y, et al., Endocrine-Related Cancer 2016; 23(4):1-19).

The tissue-specific toxicity of adrenalytic compounds correlates with cholesterol accumulation. The cholesterol level of guinea pig adrenal glands rises within an hour after ATR-101 administration and increases 3-fold after 24 hours (see, e.g., Wolfgang G H, et al., Life Sci 1995; 56(13):1089-93). ATR-101 toxicity in cynomologous monkeys is limited to cholesterol-rich tissues, including the adrenal cortex, the corpus luteum, and sebaceous glands (see, e.g., Reindel J F, et al., Toxicol Pathol 1994; 22(5):510-8). Low density lipoprotein (LDL) deficient WHHL rabbits are resistant to the adrenalytic effect of FR145237 (see, e.g., Matsuo M, et al., Toxicol Appl Pharmacol 1996; 140(2):387-92). The mechanisms whereby ATR-101 causes cholesterol accumulation and their roles in ATR-101 cytotoxicity were unknown.

The adrenal cortex has high rates of cholesterol uptake, synthesis, trafficking, metabolism and efflux that must be balanced over time to support steroidogenesis and to prevent the accumulation of toxic levels of cholesterol (see, e.g., Miller W L, et al., J Lipid Res 2011; 52(12):2111-35). Cholesterol is imported from low density lipoprotein particles at a steady-state rate that depends on the level of LDL receptors (see, e.g., Goldstein J L, et al., Arterioscler Thromb Vasc Biol 2009; 29(4):431-8). Cholesterol from high density lipoprotein particles enters steroidogenic cells through passive diffusion (see, e.g., Reaven E, et al., Proc Natl Acad Sci USA 2001; 98(4):1613-8). Cholesterol synthesis in the adrenal glands and testes utilizes a unique pathway that provides cholesterol for steroidogenesis (see, e.g., Mitsche M A, et al., Elife 2015; 4:e07999).

Adrenocortical cells must respond rapidly to stress and to other signals that induce steroidogenesis within minutes after a stimulus (see, e.g., Fallahsharoudi A, et al., Sci Rep 2015; 5:15345; Bose H S, et al., Nature 2002; 417(6884): 87-91). Many inhibitors of steroidogenesis cause a rapid increase in the cholesterol content of the adrenal glands or of cultured adrenocortical cells (see, e.g., Lehoux J G, et al., J Mol Endocrinol 1991; 6(3):223-30; Sbiera S, et al., Endocrinology 2015; 156(11):3895-908; DiBartolomeis M J, et al., J Biol Chem 1986; 261(10):4432-7). Some compounds increase both cholesterol and cholesteryl ester levels, indicating that that the increases in cholesterol levels do not involve the inhibition of cholesterol esterification (see, e.g., Lehoux J G, et al., J Mol Endocrinol 1991; 6(3):223-30; Pandey A, et al., Toxicology Reports 2015; 2:1075-85; Brecher P I, et al., Endocrinology 1978; 102(5):1404-13). Consequently, fluctuations in the amount of cholesterol consumed by steroidogenesis cannot be compensated for by changes in cholesterol ester storage alone.

Cholesterol trafficking is required both for the maintenance of appropriate cholesterol levels of different cell membranes and for cholesterol efflux (see, e.g., Ikonen E. Nat Rev Mol Cell Biol 2008; 9(2):125-38). ATP-binding cassette (ABC) transporters (ABCA1, ABCG1, MDR1) regulate the vesicular trafficking of cholesterol between different membranes (see, e.g.,Yamauchi Y, et al., J Biol Chem 2015; 290(39):23464-77; Tarling E J, et al., Proc Natl Acad Sci USA 2011; 108(49):19719-24; Luker G D, et al., J Biol Chem 1999; 274(11):6979-91; Debry P, et al., J Biol Chem 1997; 272(2):1026-31). Disruptions to cholesterol trafficking contribute to cholesterol accumulation and toxicity in several human diseases (see, e.g., Sahakitrungruang T. Ann Pediatr Endocrinol Metab 2015; 20(1):1-7; Vanier M T. J Rare Dis 2010; 5:16; Porto A F. Pediatr Endocrinol Rev 2014; 12 Suppl 1:125-32).

Cholesterol efflux is controlled by the active transport of cholesterol to extracellular acceptors by ABC transporters. The ABCA1 and ABCG1 transporters are thought to be the principal conduits for cholesterol export from macrophages (see, e.g., Wang X, et al., J Clin Invest 2007; 117(8):2216-24; Out R, et al., Circ Res 2008; 102(1):113-20). ABCA1 and ABCG1 are enriched in the adrenal cortex, yet no adrenocortical dysfunction was reported in Abcal/Abcgl double knockout mice (see, e.g., Out R, et al., Circ Res 2008; 102(1):113-20). Different phenotypes have been reported for Abcal single knockout mice, including either reduced or increased cholesterol levels in the adrenal cortex and either normal or enlarged adrenal glands (see, e.g., Orso E, Nat Genet 2000; 24(2):192-6; Christiansen-Weber T A, et al., Am J Pathol 2000; 157(3):1017-29; McNeish J, et al., Proc Natl Acad Sci USA 2000; 97(8):4245-50). It is possible that compensatory effects of other transporters or differences in genetic backgrounds or mouse husbandry affect the phenotypes that are produced by Abca1 and/or Abcg1 ablation.

The multiple drug resistance protein 1/P-glycoprotein (MDR1/ABCB1/P-gp) can influence both cholesterol levels and steroid secretion. Cells that overexpress MDR1 have higher levels of cholesterol uptake and cholesterol ester storage (see, e.g., Luker G D, et al., J Biol Chem 1999; 274(11):6979-91; Tessner T G, et al., Biochem Biophys Res Commun 2000; 267(2):565-71). Ectopically expressed MDR1 does not increase cholesterol efflux in HEK293, HeLa, or 77.1 cells (see, e.g., Le Goff W, et al., J Lipid Res 2006; 47(1):51-8; Morita S Y, et al., Hepatology 2007; 46(1):188-99). MDR1 is required to maintain normal circulating corticosterone levels in mice and for steroid secretion by mouse adrenocortical cells (see, e.g., Altuvia S, et al., J Biol Chem 1993; 268(36):27127-32; Muller M B, et al., Neuropsychopharmacology 2003; 28(11):1991-9) . It is not known if the effects of MDR1 on cholesterol levels and on steroid secretion are direct and independent or each other, or if these effects are indirect consequences of as single molecular function of MDR1.

Acyl-coenzyme A cholesterol: acyltransferase (ACAT) inhibition was proposed to cause adrenalytic activity and cytotoxicity in ACC cell lines related to H295R cells (see, e.g., Sbiera S, et al, Endocrinology 2015; 156(11):3895-908; LaPensee C R, et al., Endocrinology 2016; 157(5):1775-88). Most ACAT inhibitors do not cause cholesterol accumulation or cytotoxicity in the cells that have been tested, and differences in the efficiencies of ACAT inhibition do not correlate with cytotoxicity (see, e.g., Junquero D, et al., Biochem Pharmacol 2001; 61(4):387-98; Pokhrel L, et al., J Med Chem 2012; 55(20):8969-73; Rodriguez A, et al., Atherosclerosis 2002; 161(1):45-54; An S, et al., Exp Mol Med 2008; 40(4):407-17). Only a small proportion of ACAT inhibitors have adrenalytic activity, even though many of them have hypocholesterolemic activity in animals (see, e.g., Sliskovic D R, et al., Prog Med Chem 2002; 39:121-71). No adverse events related to adrenocortical damage were reported in phase II and phase III clinical trials of ACAT inhibitors (see, e.g., Meuwese M C, et al., JAMA 2009; 301(11):1131-9; Tardif J C, et al., Circulation 2004; 110(21):3372-7). Ablation of the gene encoding ACAT1 in mice eliminates cholesterol esterification in the adrenal cortex, but these mice do not exhibit adrenocortical damage, altered circulating corticosteroid levels, or cholesterol accumulation in the adrenals (see, e.g., Meiner V L, et al., Proc Natl Acad Sci USA 1996; 93(24):14041-6). It is therefore unlikely that ACAT inhibition is sufficient to cause cytotoxicity or adrenalytic activity.

The respective roles of cholesterol uptake, synthesis, trafficking, storage, metabolism and efflux in the control of the cholesterol levels in ACC cells were not well understood. The compensatory shifts in cholesterol flux through these pathways suggest that no single mechanism exerts overall control over the cholesterol level.

Experiments conducted during the course of developing embodiments for the present invention determined that combinations of compounds that caused cholesterol accumulation in ACC-derived cells were cytotoxic. Indeed, it was shown that prevention of the cholesterol accumulation suppressed the cytotoxicity. It was shown that cholesterol accumulation could be caused by single compounds such as ATR-101, or could be caused by combinations of compounds, such as verapamil, benzamil and glyburide. The enhanced cytotoxicity of verapamil, benzamil and glyburide in combination suggested that cytotoxicity required the simultaneous inhibition of ABCA1, ABCG1 and MDR1 ABC transporters. The adrenalytic compound ATR-101 also inhibited cholesterol efflux and cortisol secretion.

Accordingly, the present invention relates treatments of conditions related to adrenocortical activity (e.g., functional activity) (e.g., dysfunctional activity) and/or excessive steroid production comprising administering to a patient a therapeutically effective amount of one or more agents that simultaneously inhibit at least two of the following cellular functions: 1) cholesterol efflux; 2) cortisol secretion; and 3) mitochondrial activity or ATP synthesis. In some embodiments, the patient is a human patient.

In some embodiments, the agent capable of inhibiting cholesterol efflux is capable of inhibiting cholesterol efflux related to ABCA1 and/or ABCG1 (e.g., ABCA1/ABCG1 transporters). In some embodiments, inhibiting cholesterol efflux related to ABCA1 and/or ABCG1 results in, for example, free cholesterol accumulation, increased caspase activity, and decreased ATP.

In some embodiments, the agent capable of inhibiting cortisol secretion is capable of inhibiting MDR1 related cortisol secretion and/or inhibiting MDR1 P-glycoprotein multiple drug transporter activity. In some embodiments, inhibiting cortisol secretion and/or inhibiting MDR1 related cortisol secretion and/or inhibiting MDR1 P-glycoprotein multiple drug transporter activity results in, for example, decreased steroid circulation.

In some embodiments, the agent capable of inhibiting mitochondrial activity or ATP synthesis. In some embodiments, inhibiting mitochondrial activity or ATP synthesis includes, but is not limited to, inhibiting mitochondrial electron transport chain activity related to cholesterol accumulation, and mitochondrial F1F0 ATPase activity related to cholesterol accumulation.

Similarly, the present invention relates treatments of conditions related to adrenocortical activity and/or excessive steroid production involving co-administration of two or more of the following: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity.

Such treatments are not limited to specific conditions related to adrenocortical activity and/or excessive steroid production. Examples of such conditions include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension, virilization, congenital syndromes leading to excessive corticosteroid production, Conns or other syndromes of excessive steroid production, and adrenocortical cancer (ACC).

For example, in the case of treating ACC, in exposing ACC cells to such a treatment the co-administered agents sensitize cells to inducers of apoptosis and/or cell cycle arrest and, in some instances, themselves induce apoptosis and/or cell cycle arrest.

The invention further relates to methods of treating, ameliorating, or preventing conditions related to adrenocortical activity and/or excessive steroid production in a patient, such as those that are responsive to one or more agents capable of causing cytotoxic cholesterol accumulation comprising administering to the patient treatments involving co-administration two or more of the following agents: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity. Such conditions related to adrenocortical activity and/or excessive steroid production include, but are not limited to, aldosteronism, primary aldosteronism, secondary aldosteronism, hyperaldosteronism, primary hyperaldosteronism, secondary hyperaldosteronism, adrenal insufficiency, Addison's Disease, adrenoleukodystrophy, pheochromocytoma, Cushing's Syndrome, adrenal hyperplasia, congenital adrenal hyperplasia, cancer, adrenal cancer, hypertension, primary hypertension, secondary hypertension, virilization, congenital syndromes leading to excessive corticosteroid production, Conns or other syndromes of excessive steroid production, and adrenocortical cancer (ACC).

Such methods are not limited to a particular agent capable of causing cytotoxic cholesterol accumulation and/or capable of inhibiting cholesterol efflux related to ABCA1 and/or ABCG1 (e.g., ABCA1/ABCG1 transporters). In some embodiments, inhibiting cholesterol efflux related to ABCA1 and/or ABCG1 results in, for example, free cholesterol accumulation, increased caspase activity, and decreased ATP. In some embodiments, agents capable of causing cytotoxic cholesterol accumulation and/or capable of inhibiting cholesterol efflux related to ABCA1 and/or ABCG1 (e.g., ABCA1/ABCG1 transporters) include, but are not limited to, Valspodar, Glyburide, Cyclosporine A (see, e.g., Le Goff, et al., Arteriosclerosis, Thrombosis, and Vascular Biology. 2004; 24:2155-2161).

In some embodiments, the agent is capable of inhibiting cortisol secretion and/or inhibiting MDR1 related cortisol secretion and/or inhibiting MDR1 P-glycoprotein multiple drug transporter activity. In some embodiments, inhibiting cortisol secretion and/or inhibiting MDR1 related cortisol secretion and/or inhibiting MDR1 P-glycoprotein multiple drug transporter activity results in, for example, decreased steroid circulation. In some embodiments, agents capable of inhibiting cortisol secretion and/or inhibiting MDR1 related cortisol secretion and/or inhibiting MDR1 P-glycoprotein multiple drug transporter activity include, but are not limited to, Tariquidar, MK-571 (CAS 115103-85-0), Niguldipine hydrochloride (CAS 113317-61-6), Matairesinol (CAS 580-72-3), Reversin 121 ($C_{34}H_{47}N_3O_9$), Elacridar (CAS 143664-11-3), Pyrimethamine ($C_{12}H_{13}ClN_4$), Pyrimethamine Biotin ($C_{27}H_{39}N_7O_3S$), Pyrimethamine-d3 ($C_{12}H_{10}D_3ClN_4$), 8-isopentenylnaringenin (CAS 68682-02-0), JS-2190 (Boc-Glu(OBzl)-N,N'-dicyclohexylurea, $C_{30}H_{45}N_3O_6$), P-Glycoprotein Inhibitor C-4 ($C_{23}H_{18}ClNO_4$), PGP-4008 (CAS 365565-02-2), Sipholenol A (CAS 365565-02-2), Reversan (CAS 313397-13-6), CP 100356 hydrochloride (CAS 142716-85-6), PSC 833 (CAS121584-18-7), Zosuquidar trihydrochloride (CAS 167465-36-3), and Vismodegib (CAS 879085-55-9).

In some embodiments, the agent is capable of inhibiting mitochondrial activity or ATP synthesis. In some embodiments, the agent is capable of inhibiting mitochondrial activity or ATP synthesis includes, but is not limited to, mitochondrial electron transport chain activity related to cholesterol accumulation, and mitochondrial F1F0 ATPase activity related to cholesterol accumulation. In some embodiments, agents capable of inhibiting mitochondrial activity include, but are not limited to, rhodamine-123, MKT-077, decoquinate, isoniazid, suramin, erythrosine, toltrazuril, enilconazole, and metformin.

In some embodiments of the present invention, such co-administration of two or more agents is administered to an animal under one or more of the following conditions:

concurrently, at different periodicities, at different durations, at different concentrations, by different administration routes, etc.

In some embodiments, the methods of the present invention are used to treat diseased cells, tissues, organs, or pathological conditions and/or disease states in an animal (e.g., a mammalian patient including, but not limited to, humans and veterinary animals). In particular embodiments, such methods are used for treating, preventing and/or ameliorating conditions related to adrenocortical activity and/or excessive steroid production (e.g., ACC).

Some embodiments of the present invention provide methods for administering an effective amount of a treatment involving co-administration of two or more agents selected from the following: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

In a particular embodiment, the additional therapeutic agent is ATR-101.

In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the treatments involving co-administration of two or more agents selected from the following: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity further involve administration of at least one anti-hyperproliferative or antineoplastic agent selected from alkylating agents, antimetabolites, and natural products (e.g., herbs and other plant and/or animal derived compounds).

Alkylating agents suitable for use with the present invention include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present invention include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use with the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''- hexamethyl-1,3,5-triazine-2,4, 6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-l-triazeno)-imidazole-4-carboxamide (DTIC)) | DTIC-Dome | Bayer AG, Leverkusen, Germany |
| Dactinomycin, actinomycin D (actinomycin produced by Streptomyces parvullus, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal | DanuoXome | Nexstar |

TABLE 1-continued

| | | |
|---|---|---|
| ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | | Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |

TABLE 1-continued

| Drug | Brand | Manufacturer |
|---|---|---|
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) aminol-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |

TABLE 1-continued

| Drug | Brand | Company |
|---|---|---|
| Oxaliplatin (cis-[(1R,2R)-1,2-cyclohexanediamine-N,N'][oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |

TABLE 1-continued

| | | |
|---|---|---|
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoyl-phorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods involving co-administration of two or more agents selected from the following: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity, and further co-administering with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), anti-sense nucleic acids, membrane disruptive agents and the like, used alone or in combination. Indeed, any type of antibiotic may be used including, but not limited to, antibacterial agents, antiviral agents, antifungal agents, and the like.

The invention also provides pharmaceutical compositions comprising agents capable of causing cytotoxic cholesterol accumulation (e.g., agents capable of inhibiting cholesterol efflux related to ABCA1 and/or ABCG1; agents capable of inhibiting MDR1 related cortisol secretion and/or MDR1 P-glycoprotein multiple drug transporter activity; agents capable of inhibiting mitochondrial activity related to cholesterol accumulation) in a pharmaceutically acceptable carrier.

The invention also provides pharmaceutical compositions comprising two or more agents selected from the following: 1) an agent capable of inhibiting cholesterol efflux related to ABCA1 and/or ABCG1; 2) an agent capable of inhibiting MDR1 related cortisol secretion and/or MDR1 P-glycoprotein multiple drug transporter activity; and 3) an agent capable of inhibiting mitochondrial activity in a pharmaceutically acceptable carrier.

Such pharmaceutical compositions within the scope of this invention include all compositions wherein the agents are contained (separately or together) in an amount which is effective to achieve its intended purpose. While individual needs vary, determination of optimal ranges of effective amounts of each component is within the skill of the art. Typically, the agents may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the agent or its solvates.

In a topical formulation, the agent may be present at a concentration of about 0.01 to 100 mg per gram of carrier. In a one embodiment, the agent is present at a concentration of about 0.07-1.0 mg/ml, for example, about 0.1-0.5 mg/ml, and in one embodiment, about 0.4 mg/ml.

In addition to administering the agent as a raw chemical, the agents may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

Such pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active agents with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active agents are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active agents with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active agents in water-soluble form, for example, water-soluble salts and alkaline solutions. In addition, suspensions of the active agents as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXPERIMENTAL

The following examples are provided to demonstrate and further illustrate certain preferred embodiments of the present invention and are not to be construed as limiting the scope thereof.

Example I

This example provides the materials and methods utilized in Examples II-XI.

Cell Culture Conditions

H295R and BD140C cells were cultured in DMEM without glucose (Gibco) supplemented with 10 mM galactose, 5% FBS, 0.1 mg/ml penicillin-streptomycin, 2 mM L-glutamine, 5 mM sodium HEPES, 1 mM sodium pyruvate, and the compounds indicated in each experiment. To examine the effects of serum cholesterol, the medium of cells that were cultured under standard conditions was replaced with serum-free medium containing the indicated compounds. The cells were cultured in serum-free medium for the indicated time, and were analyzed using the same protocols that were used for cells that were cultured in serum-containing medium.

Visualization of Cholesterol Levels and of Cholesterol Esterification

The cells were seeded in 96-well ibiTreat μ-Plates and allowed to adhere for 48 h prior to the start of each experiment. Cholesterol was detected in fixed cells by incubating with 100 μg/ml filipin III at 37 C for 2 h. The bound filipin III was imaged by fluorescence microscopy using 377/11 nm excitation and 447/60 nm emission wavelengths. Images were captured using either a 4× or a 60× objective. Cholesterol esterification was visualized by culturing the cells with 1 μM NBD-cholesterol for 2 h following incubation with the indicated compounds. NBD-cholesterol esters were imaged by fluorescence microscopy using 485/20 nm excitation wavelengths. Images were captured using either a 20× or a 60× objective.

ATP and Caspase 3/7 Assays

The ATP levels of cells were measured by lysis in CellTiter-Glo reagent (Promega), and measurement of the luminescence. The caspase 3/7 activities of cells were measured by lysis in Apo-ONE reagent (Promega) and measurement of the fluorescence.

media with and without 50 μM glibenclamide, which inhibits ABCA1 activity. The total amount of cell-associated cholesterol that was released into the wash medium was measured using a fluorometric enzyme-linked assay (Cayman Chemical). Cholesterol esters were hydrolyzed using cholesterol esterase. Cholesterol was oxidized by cholesterol oxidase, producing hydrogen peroxide. The hydrogen peroxide was reacted with 10-acetyl-3,7-dihydroxyphenoxazine (ADHP) in the presence of horseradish peroxidase to produce resorufin. Resorufin fluorescence was measured using 555 nm exitation and 590 nm emission wavelengths in a SpectraMax M5 microplate reader (Molecular Devices).

Cholesterol efflux was measured by replacing the culture medium with serum-free medium supplemented with 5 μg/ml apoA1 (Sigma) and the indicated compounds. After the indicated time, the serum-free medium was collected, and the cholesterol concentration was measured using the fluorometric enzyme-linked assay (Cayman Chemical).

Cortisol secretion was measured by replacing the culture medium with fresh medium containing the indicated compounds. The medium was collected at the indicated times. The cortisol concentration in the medium was measured using indirect ELISA (Arbor Assays).

Doxorubicin was imaged by fluorescence microscopy in live cells using 485/20 nm excitation wavelengths and either a 10× or 20× objective.

Transcript Measurement mRNA was isolated (Qiagen), and was reverse transcribed using the Transcriptor First Strand cDNA synthesis kit (Roche). The relative amounts of cDNAs corresponding to the indicated transcripts were quantified using qPCR assays with specific primers (Table 2).

TABLE 2

Primer sequences used for qPCR

| gene | SEQ ID NO: | forward primer | SEQ ID NO: | reverse primer |
| --- | --- | --- | --- | --- |
| ABCA1 | 1 | ACAATCCTGCAGTGCTTCCT | 2 | GGCAGGTACAGCGTGAAGTAG |
| ABCG1 | 3 | TGCTTCCACACTGTTGTCCT | 4 | CTTGACCATTTCCCTTCTGC |
| IDOL | 5 | CGAGGACTGCCTCAACCA | 6 | TGCAGTCCAAAATAGTCAACTTCT |
| ACTHR | 7 | CATGGGCTATCTCAAGCCAC | 8 | GAGATCTTCCTGGTGTGGGATC |
| CYP17A1 | 9 | GCATCATAGACAACCTGAGCAA | 10 | GGGTTTTGTTGGGGAAAATC |
| SULT2A1 | 11 | AAGCTGATCTGCCTGTAGCTG | 12 | TGGTGTGAGGGTTTCAACTG |
| HSD3B2 | 13 | CCAGTAGCATAGAGGTAGCC | 14 | TCAGATTCCACCCGTTAGC |
| CYP21A2 | 15 | TTGTGGACATGATTCCCTTTC | 16 | CTGCTTCTCCTCGTTGTGGT |
| CHOP | 17 | TGTTCAAGAAGGAAGTGTATCTTCA | 18 | TGATGCCTGTTTTTGTAGGTAAAG |

Cholesterol Crystallization and Efflux, Cortisol Secretion and Doxorubicin Clearance To quantify cholesterol crystallization, experiments were conducted that measured the total extracellular cholesterol that was associated with the cells. After culturing cells with the indicated compounds, the culture medium was removed. Medium lacking cholesterol was added to the cells, and the extracellular cholesterol that was released into the wash medium was collected after 30 seconds. To establish if the cholesterol that was released from the cells was exported by ABCA1, the wash step was performed in parallel using Data Analysis The data were analyzed using GraphPad Prism v7.00 software. Data are shown as means±2 SDs. The number of samples included in each analysis is indicated in each figure legend and refers to separate cultures of cells from more than one experiment. Groups that were used for statistical analysis include at least five samples. Technical replicates were performed to ensure the reliability of the measurements, and were not included in the data analysis and presentation. A P value <0.05 was interpreted to indicate statistical significance. The results of all statistical tests are shown in the supplementary information.

Pharmacological Reagents

ATR-101 was synthesized and purified as described (see, e.g., Trivedi B K, et al., J Med Chem 1994; 37(11):1652-9; Cheng Y, et al., Endocrine-Related Cancer 2016; 23(4):1-19). Other compounds were purchased from the vendors listed in the supplemental information.

Sources of Cultured Cells

H295R cells were obtained from ATCC and were validated by analysis of their corticosteroid profile. BD140C cells were obtained from Kimberly Bussey (Tgen, Ariz.).

Nomenclature of Targets and Ligands

Key protein targets and ligands in this article are hyperlinked to corresponding entries in http://www.guidetopharmacology.org, the common portal for data from the IUPHAR/BPS Guide to PHARMACOLOGY (see, e.g., Southan, et al., 2016 Nucleic Acids Res, 44, D1054-68), and are permanently archived in the Concise Guide to PHARMACOLOGY 2015/16 (see, e.g., Alexander, et al., 2015 Br J Pharmacol, 172, 5729-43).

Reagents

ATR101, PD129337 (Sigma #PH001507), glyburide (Abcam #ab120267), zosuquidar (Sigma #SML1044), benzamil (Sigma #B2417), cyclosporin A (Cayman #12088), rhodamine 123 (Cayman #16672), olesoxime (ToCris #2906), doxorubicin (Cayman #15007), ketoconazole (Sigma #K1003), abiraterone acetate (Cayman #15148), metyrapone (Cayman #14994), trilostane (Cayman #14164), anastrozole (Cayman #11987), and U18666A (Sigma #U3633) were dissolved in DMSO at concentrations ranging from 50 to 250 mM. The final concentration of DMSO for all samples within each experiment was the same and ranged from 0.1 to 0.4% for all experiments. NBD-cholesterol (Molecular Probes #N1148), cholesterol (Sigma #C3045), cholesterol linoleate (Sigma #CO289), and α-tocopherol (Sigma #T3251) were dissolve in ethanol at concentrations ranging from 20 to 240 mM. The final concentration of ethanol for all samples within each experiment was the same and ranged from 0.02 to 0.2% for all experiments. Verapamil (Sigma #V4629), methyl-β-cyclodextrin (Sigma #C4555), and methyl-β-cyclodextrin:cholesterol complexes (Sigma #C4951) were dissolved in the cell culture media.

Cell Culture

The H295R adrenocortical carcinoma cell line was obtained from ATCC. The cells were tested and confirmed to be free of mycoplasma by Radil Inc. The BD140C adrenocortical carcinoma cell line was kindly provided by Dr. Kimberly Bussey (TGen, Pheonix, Ariz.). The cell lines were cultured in DMEM/F12 media (Gibco #11330) supplemented with 10% FBS (Atlanta Biologicals #S11595, lots E12069, H1030), and 1% penicillin-streptomycin (Gibco #15140). 7-9 days before each experiment the cells were passed 2 times in DMEM without glucose (Gibco#11966) supplemented with 10 mM galactose, 5% FBS (Atlanta Biologicals # S11595, lots E12069, H1030), 1% penicillin-streptomycin (Gibco #15140), 1% L-glutamate (Gibco #25030), 5 mM sodium HEPES, and 1 mM sodium pyruvate. The total serum cholesterol concentration in the culture medium was 42.7 µM. The cells were allowed to adhere to the tissue culture plates for 48 h after the second passage before the start of each experiment.

Visualization of Cholesterol in Cells

The cells were seeded in 96-well ibiTreat µ-Plates (Ibidi #89626) in 100 µl at a density of 50,000 cells per well. After 48 h, 20-80 µl media was removed from each well and replaced with 20 µl of each compound diluted to 6× of the final concentration in the culture medium to produce a final volume of 120 µl. The cells were incubated at 37 C in 5% $CO_2$ atmosphere for a time ranging from 15 min to 24 h. The medium was removed and immediately replaced with 100 µl of 4% paraformaldehyde and the cells were fixed at room temperature for 20 min. The cells were washed twice with 200 µl PBS. The freshly prepared filipin III (Cayman #70440) stock solution (10 mg/ml in DMSO) was diluted 100× in PBS for a final concentration of 100 µg/ml and added directly to cells. The fixed cells were incubated with filipin III at 37 C in the dark for 2 h. The cells were washed twice with 100 µl PBS, and the bound filipin III was visualized by fluorescence microscopy using 377/11 nm excitation and 447/60 nm emission wavelengths and a 60× oil objective.

Visualization of Cholesterol Esterification in Cells

The cells were seeded in 96-well ibiTreat µ-Plates (Ibidi) in 100 µl at a density of 50,000 cells per well. After 48 h, 20-80 µl media was removed from each well and replaced with 20 µl of each compound diluted to 6× of the final concentration in the culture medium to produce a final volume of 120 µl. The cells were incubated at 37 C in 5% $CO_2$ atmosphere for either 2 or 22 h. 5 µl of NBD-cholesterol was added to each well to produce a final concentration of 1 µM. When NBD-cholesterol is esterified and localized to cytoplasmic lipid droplets, it produces bright fluorescent foci in the cell. The inhibition of ACAT activity prevents fluorescent focus formation by NBD-cholesterol (see, e.g., Lada, et al., 2004 J Lipid Res, 45, 378-86). After 1.5 h, 5 µl of Hoechst 33342 was added to each well to produce a final concentration of 3 µg/ml. After 30 min, the medium was replaced with fresh medium. NBD-cholesterol esterification was visualized by fluorescence microscopy using either 485/20 nm (NBD) or 387/11 nm (Hoechst) excitation wavelengths and images were captured using either a 60× oil objective or a 20× objective.

Cellular ATP Level

The cells were seeded in 96-well tissue culture plates (Corning #3585) in 100 µl at a density of 25,000 cells per well. After 48 h, 20-80 µl of medium was removed from each well and replaced with 20 µl of each compound diluted to 6× of the final concentration in the culture medium to produce a final volume of 120 µl. The cells were incubated at 37 C in 5% $CO_2$ atmosphere for a time ranging from 15 min to 24 h. The medium was removed and immediately replaced with 50 µl of CellTiter-Glo luminescence cell viability assay reagent (Promega). The cells were lysed by agitation at room temperature for 20 min in the dark. The luminescence was measured using a SpectraMax M5 microplate reader (Molecular Devices) with a 0.5 s acquisition time. The luminescence (RLU) values for control cells ranged from 5000 to 20000 RLU in all experiments, and were scaled by a factor of 0.001 to plot all graphs.

Caspase 3/7 Activity

The cells were seeded in 96-well tissue culture plates (Corning #3585) in 100 µl at a density of 25,000 cells per well. After 48 h, 20-80 µl of medium was removed from each well and replaced with 20 µl of each compound diluted to 6× of the final concentration in the culture medium to produce a final volume of 120 µl. The cells were incubated at 37 C in 5% $CO_2$ atmosphere for a time ranging from 15 min to 24 h. The medium was removed and immediately replaced with 50 µl of Apo-ONE homogenous caspase-3/7 assay reagent diluted in buffer according to the manufacturer's protocol (Promega). The samples were incubated for 18 h at room temperature in the dark. The fluorescence was measured using a SpectraMax M5 microplate reader with a 0.5 s acquisition time. The fluorescence values (RFU) for control cells ranged from 500 to 1000 RFU in all experiments and were scaled by a factor of 0.001 to plot all graphs.

Extracellular Cholesterol Associated with Cells

The cells were seeded in 96-well tissue culture plates (Corning #3585) in 100 µl at a density of 100,000 cells per well. After 48 h, 60 µl of medium was removed from each well and replaced with 10 µl of each compound diluted to 6× of the final concentration in the culture medium to produce a final volume of 60 µl. The cells were incubated at 37 C in 5% CO2 atmosphere for 4 h. The medium was removed and replaced with 50 µl serum-free medium supplemented with 5 µg/mL apo-AI (without or with 50 µM glyburide to detect ABCA1 transporter-dependent efflux) for either 30 sec or 1 h at 37 C in 5% CO2 atmosphere. After the indicated time, the supernatant, was transferred to a new 96-well plate and a fluorometric-base cholesterol detection assay cocktail was added.

Cholesterol Efflux

The cells were seeded in 96-well tissue culture plates (Corning #3585) in 100 µl at a density of 100,000 cells per well. After 48 h, the medium was removed and replaced with 50 µl serum-free medium supplemented with 5 µg/mL apoA1. After the indicated time, the supernatant containing the effluxed cholesterol, was transferred to a new 96-well plate. A cholesterol detection reagent (Cayman Chemical) consisting of cholesterol assay buffer, cholesterol assay detector (10-acetyl-3,7-dihydroxyphenoxazine [ADHP]), horseradish peroxidase, cholesterol oxidase, and cholesterol esterase was added, and the reactions were incubated for 30 min at 37 C. The fluorescence intensities were measured using ex. 555 nm/em. 590 nm. The cholesterol concentrations were calculated by interpolation between the values produced by cholesterol standards that were analyzed in parallel.

To measure the ATP levels in the same cells that were used to measure cholesterol efflux, 100 µl of CellTiter-Glo ATP detection reagent was added, and the cells were lysed by agitation at room temperature for 20 min in the dark. The luminescence was measured using a SpectraMax M5 microplate reader (Molecular Devices) with a 0.5 s acquisition time. The luminescence (RLU) values for control cells ranged from 5000 to 20000 RLU in all experiments, and were scaled by a factor of 0.001 to plot all graphs.

Cortisol Secretion

The cells were seeded in 96-well tissue culture plates (Corning #3585) in 100 µl at a density of 100,000 cells per well. After 48 h, the medium was removed and replaced with 50 µl of fresh medium. After the indicated incubation time, aliquots of the supernatant ranging from 0.5 to 10 µl were diluted in 50 µl of medium were used to measure the amount of cortisol secreted. Cortisol detection and quantification were performed by indirect ELISA according to the manufacturer's protocol (Arbor Assays #K003).

Doxorubicin Clearance

The cells were seeded in 96-well ibiTreat µ-Plates (Ibidi #89626) in 100 µl at a density of 50,000 cells per well. After 48 h, 40-60 µl of medium was removed from each well and replaced with 20 µl of 150 µM doxorubicin and the indicated compounds diluted to 6× of the final concentration in the culture medium, to produce a final volume of 120 µl (final doxorubicin concentration of 25 µM). The cells were incubated at 37 C in 5% CO2 atmosphere until significant doxorubicin accumulation could be detected in the ATR-101 treated samples relative to control samples (2 h). The medium was removed and immediately replaced with 100 µl of fresh media and intracellular doxorubicin fluorescence was visualized by fluorescence microscopy using a 20× objective.

Transcript Measurement

H295R cells were seeded in 6-well tissue culture plates (Corning #3506) at a density of 5 X105 per well. After 48 h, the compound(s) indicated were added, and the cells were cultured for the indicated time. The cells were harvested in 1.35 ml culture medium with trypsin. The cells were collected by centrifugation and lysed in 350 µl of RLT buffer (Qiagen) with β-mercaptoethanol. mRNA extraction and DNase treatment were performed according to the manufacturer's protocol (Qiagen). All RNA samples had 260/280 ratios greater than 1.5. The same amount of RNA ranging from 0.1 to 0.5 µg was used for reverse transcription using the Roche Transcriptor First Strand cDNA synthesis kit (Roche #04897030001) using the manufacturer's protocol. SYBR Green I-based real-time qPCR assays were performed using a Roche LightCycler480 instrument. The levels of transcripts in different samples were normalized by the levels of RPL9 transcripts.

Molecular Docking Simulations

A web-based docking engine (http://swissdock.eu) was used to simulate ATR-101 and PD129337 binding to LXRa (PDB ID: 1UHL). ChemBioOffice was used to create mol2 files of the compounds for docking. The UCSF Chimera dockprep plugin was used to prepare PDB files for docking.

Abbreviations

ATR-101: N-(2,6-bis(1-methylethyl)phenyl)-N'-((1-(4-(dimethylamino) phenyl)cyclopentyl)methyl)urea hydrochloride PD129337: N-(2,6-bis(1-methylethyl)phenyl)-N'-((1-(phenyl)cyclopentyl)methyl)urea hydrochloride DMSO: dimethyl sulfoxide ACAT: acyl-CoA: cholesterol acyltransferase NBD-cholesterol: 22-(N-(7-Nitrobenz-2-oxa-1,3-diazol-4-yl)amino)-23,24-bisnor-5-cholen-3β-ol ATP: adenosine 5'-triphosphate MβCD: methyl-β-cyclodextrin ABCA1: ATP-binding cassette subfamily A member 1

ABCG1 ATP-binding cassette subfamily G member 1

MDR1: Multiple Drug Resistance Protein 1

CHOP: CCAAT-enhancer-binding protein homologous protein qPCR: quantitative real-time PCR LXR: liver X receptor PDB: Protein Data Bank Example II This example demonstrates the kinetics and specificity of cholesterol accumulation, ATP depletion and caspase activation in response to ATR-101 addition to ACC-derived cell lines.

Figure 1A:
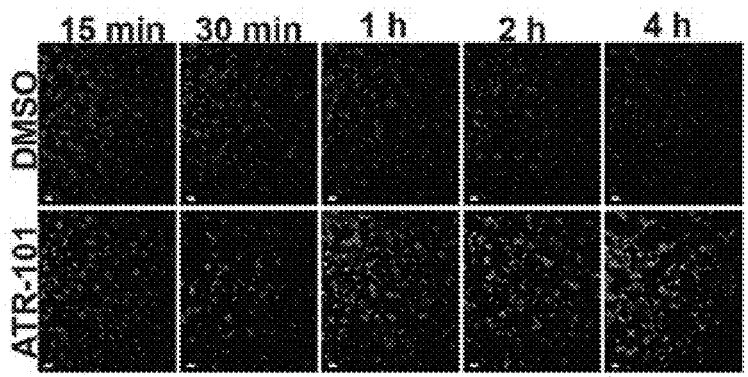
FIG. 1A: Time-dependence of the effect of ATR-101 on the cholesterol levels in H295R cells. The cells were cultured with DMSO vehicle or with 60 µM ATR-101 for the times indicated above the images. The images show filipin III binding to cholesterol in fields containing 5,500-7,800 cells. The scale bars denote 100 µm. The fluorescence intensities of the cell populations and the statistical significance of the differences are shown in FIG. 2A.
Figure 1B:
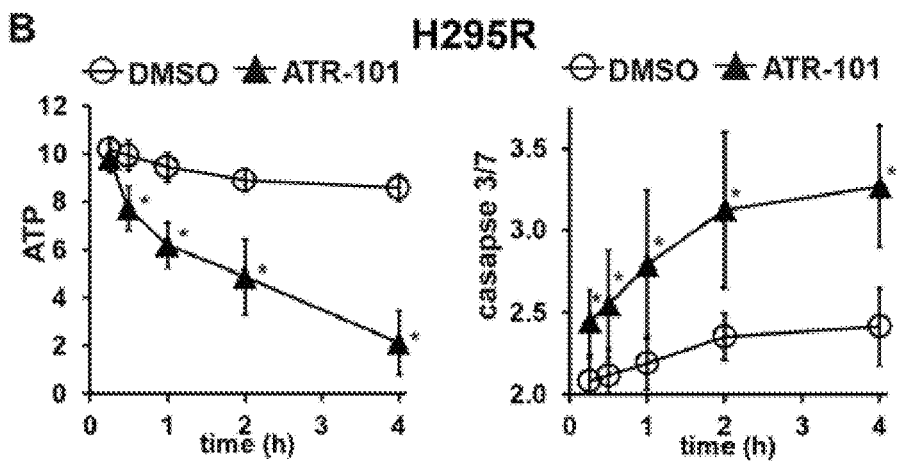
FIG. 1B: Time-dependence of the effects of ATR-101 on the ATP levels and on the caspase 3/7 activities in H295R cells. The cells were cultured with DMSO vehicle or with 100 µM ATR-101 for the indicated times. The ATP levels (left graphs) and the caspase 3/7 activities (right graphs) were measured in cells that were grown in parallel. The graphs show the means and the standard deviations of five samples from three experiments. The statistical significance of the differences in ATP levels and the caspase 3/7 activities at each time after ATR-101 addition were evaluated by using two-way analysis of variance followed by Sidak's post hoc tests (ATR-101 vs. DMSO control, *$P<0.05$).

Since ATR-101 causes cholesterol accumulation and ATP depletion in the adrenal glands of guinea pigs as a harbinger of adrenalytic activity, experiments were conducted that examined the effects of ATR-101 on cholesterol and ATP levels as well as on caspase 3/7 activities in ACC-derived cells. Cholesterol accumulation was detected 15 minutes after ATR-101 addition to H295R cells (FIGS. 1A, 2A). ATP depletion and caspase activation were detected 30 and 15 minutes after ATR-101 addition, respectively (FIG. 1B). The rapid accumulation of cholesterol, ATP depletion, and caspase activation upon ATR-101 addition to cells indicate that these effects of ATR-101 were causes rather than consequences of ATR-101 cytotoxicity.

To investigate the specificity of the effect of ATR-101 on cholesterol accumulation, experiments were conducted that compared the effects of ATR-101 and PD129337 in ACC-derived cell lines. ATR-101 and PD129337 have closely related molecular structures and both of them inhibit ACAT activity, but only ATR-101 has adrenalytic activity (see, e.g., Trivedi, et al., 1993, J Med Chem, 36, 3300-7; Trivedi, et al., 1994, J Med Chem, 37, 1652-9). ATR-101 caused cholesterol accumulation in or near the plasma membrane of both H295R and BD140C cells (FIG. 1C). PD129337 did not cause cholesterol accumulation, even when it was added at a five-fold higher concentration than ATR-101 (FIG. 1C).

Figure 1D:
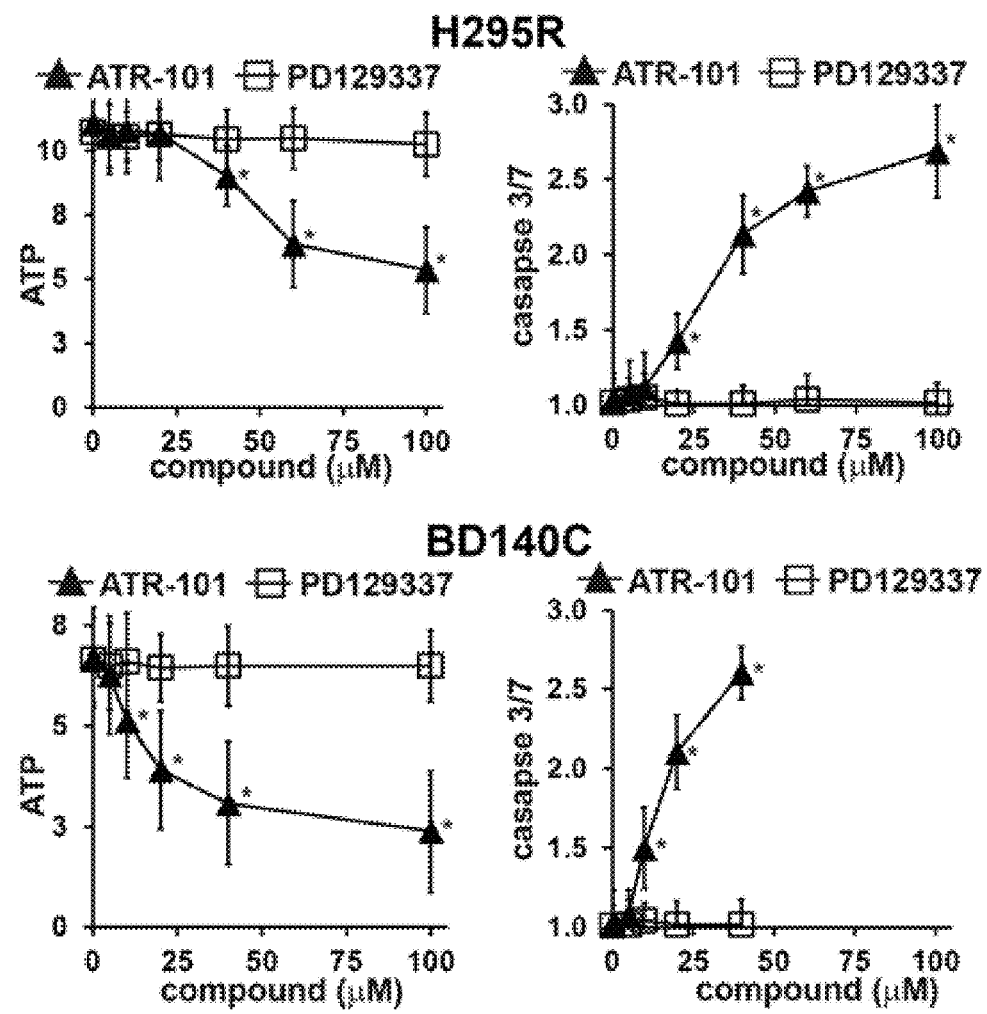
FIG. 1D: Effects of different concentrations of ATR-101 versus PD132997 effects on the ATP levels and caspase activities in H295R and BD140C cells. H295R (upper panels) and BD140C (lower panels) were cultured with the indicated concentrations of ATR-101 or PD129337 for 4 h. The ATP levels (left graphs) and the caspase 3/7 activities (right graphs) were measured in cells that were grown in parallel. The graphs show the means and the standard deviations of eight samples from four experiments and five samples from three experiments in H295R and BD140C cells, respectively. The statistical significance of the differences in ATP levels and the caspase 3/7 activities of cells that were cultured with different compounds were evaluated by using two-way analysis of variance followed by Sidak's post hoc tests (ATR-101 vs. PD129337, *$P<0.05$). The ATP levels and the caspase activities of H295R and BD140C cells that were cultured with ATR-101 versus PD132997 for 24 hours are shown in FIG. 2B.

To evaluate the specificity of the effects of ATR-101 on ATP depletion and caspase activation, experiments were conducted that compared the effects of ATR-101 and PD129337 in ACC-derived cell lines. ATR-101 reduced the ATP level and increased the caspase 3/7 activity of H295R and BD140C cells (FIG. 1D). The concentrations of ATR-101 that caused ATP depletion and caspase activation were similar to those that caused cholesterol accumulation both in H295R and in BD140C cells. PD129337 did not reduce the ATP level or increase the caspase 3/7 activity, even when it was added at a five-fold higher concentration than ATR-101 for up to 24 hours (FIGS. 1D, 2B). ATR-101 therefore caused cholesterol accumulation, ATP depletion and caspase activation by specific mechanisms that required structural determinants that are not present in PD129337.

To evaluate the potential roles of cholesterol accumulation versus ACAT inhibition in ATR-101 cytotoxicity, experiments were conducted that compared the effects of ATR-101 and PD129337 on cholesterol esterification, the ATP level, and caspase 3/7 activity in ACC-derived cell lines. Both ATR-101 and PD129337 inhibited NBD-cholesterol esterification and accumulation in lipid droplets in H295R and BD140C cells (FIG. 1E). PD129337 inhibited cholesterol esterification more efficiently than ATR-101 did, consistent with its lower ACAT inhibitory coefficient (FIG. 2C) (see, e.g., Trivedi, et al., 1993, J Med Chem, 36, 3300-7; Trivedi, et al., 1994, J Med Chem, 37, 1652-9). However, PD129337 did not cause ATP depletion or caspase activation at any concentration tested (FIG. 1D). The concentration of ATR-101 that was required for ATP depletion and caspase activation was more than two orders of magnitude higher than the concentration that inhibited cholesterol esterification (FIG. 1D). ACAT inhibition alone therefore did not cause cytotoxicity in these ACC-derived cells.

Example III

This example demonstrates the suppression of ATR-101 cytotoxicity by compouds that prevent cholesterol accumulation in cells that are cultured with ATR-101.

To determine if cholesterol accumulation was required for ATR101 cytotoxicity, experiments were conducted that evaluated the effects of cholesterol sequestration by methyl-β-cyclodextrin (MβCD) on ATP depletion and caspase activation by ATR-101. Addition of MβCD together with ATR-101 prevented cholesterol accumulation in H295R cells (FIGS. 3A, 4A). MβCD also prevented ATP depletion and caspase activation by ATR-101 both at 4 h and 24 h after addition to H295R cells (FIGS. 3B, 4B). Cells that were cultured with ATR-101 alone were small and rounded, whereas cells that were cultured with ATR-101 in the presence of MβCD remained flat and adherent for at least 30 h (FIG. 4E). MβCD alone had little effect on the ATP level, the caspase 3/7 activity, or the morphology of H295R cells (FIGS. 3B, 4B, 4E). MβCD did not eliminate all effects of ATR-101, indicating that it did not prevent ATR-101 entry into cells or effects that were independent of cholesterol accumulation (FIGS. 4F, 5D).

Experiments were conducted that examined the effects of adding exogenous cholesterol together with ATR-101 to H295R cells. Unexpectedly, cells that were cultured with ATR-101 together with exogenous cholesterol had lower cholesterol levels than cells that were cultured with ATR-101 alone for 4 h or 24 h (FIGS. 3C, 4A). Consistent with the decrease in intracellular cholesterol, the addition of exogenous cholesterol partially restored the ATP level of cells that were cultured with ATR-101 (FIGS. 3D, 4C). Exogenous cholesterol also reduced caspase activation in cells that were cultured with ATR-101 for 24 (FIG. 3D). Cells that were cultured with ATR-101 in the presence of exogenous cholesterol remained flat and adherent for at least 30 h, whereas cells that were cultured with ATR-101 alone were small and rounded (FIG. 4E). Exogenous cholesterol alone had no detectable effect on the cholesterol level, the ATP level, the caspase 3/7 activity, or morphology of H295R cells (FIGS. 3C, 3D, 4A, 4C, 4E). The reduction in the intracellular cholesterol level of cells that were cultured with ATR-101 upon addition of exogenous cholesterol correlated with an increase in cell-associated extracellular cholesterol (see FIGS. 3E, 3F below). In contrast to exogenous cholesterol, exogenous cholesterol linoleate did not prevent the accumulation of cholesterol or ATP depletion caused by ATR-101 (FIGS. 4A, 4D). Moderate cholesterol:MβCD concentrations also reduced ATP depletion by ATR-101, whereas high cholesterol:MβCD concentrations increased the cholesterol level and caused ATP depletion both alone and in combination with ATR-101 (FIGS. 4H, 4I). The suppression of ATR-101 dependent cholesterol accumulation, ATP depletion and caspase activation by exogenous cholesterol corroborated the essential role of cholesterol accumulation in ATR-101 cytotoxicity.

To establish if exogenous cholesterol affected ATR-101 entry into the cells or cholesterol esterification, experiments were conducted that tested the effects of exogenous cholesterol on NBD-cholesterol esterification in the presence and absence of ATR-101. There was no significant difference in NBD-cholesterol esterification, or in its inhibition by ATR-101, between cells that were cultured in the presence and in the absence of exogenous cholesterol (FIG. 4G).

The consistent relationship between cholesterol accumulation and ATP depletion in cells that were cultured with ATR-101 alone, and the suppression of cholesterol accumulation and prevention of ATP depletion by MβCD as well as by exogenous cholesterol support the hypothesis that cholesterol accumulation is necessary for ATR-101 cytotoxicity.

Example IV

The example demonstrates cholesterol crystallization at the plasma membrane of cells that are cultured with ATR-101.

Experiments were conducted that observed that H295R cells that were cultured with ATR-101 were associated with crystals that emanated from the cell membrane (FIG. 3E). These needle-shaped crystals were similar to cholesterol crystals that are associated with cholesterol-loaded macrophages as well as other cells with high cholesterol levels (see, e.g., Kellner-Weibel, et al., Arterioscler Thromb Vasc Biol 1999; 19(8):1891-8). H295R cells that were grown with ATR-101 in combination with MβCD did not produce crystals, consistent with sequestration of the cholesterol by MβCD (FIG. 4A).

H295R cells that were cultured with ATR-101 in combination with exogenous cholesterol produced more extracellular crystals than cells that were cultured with ATR-101 or exogenous cholesterol separately (FIG. 4G). Experiments were conducted that quantified the total extracellular cholesterol that was associated with cells that were cultured with ATR-101 and exogenous cholesterol separately and in combination as described in the methods. ATR-101 and extracellular cholesterol increased the total extracellular cholesterol that was associated with H295R cells (FIG. 3F). The concurrent increase in cholesterol crystals and decrease in intracellular cholesterol caused by exogenous cholesterol in the presence of ATR-101 suggests that exogenous cholesterol reduced intracellular cholesterol accumulation by facilitating cholesterol crystallization at the plasma membrane. The total extracellular cholesterol that was associated with cells after 4 h culture with ATR-101 and exogenous cholesterol was larger than the total amount of cholesterol that was exported from control cells in the same time (FIG. 3F). The passive discharge of cholesterol was therefore sufficient to prevent intracellular cholesterol accumulation in the presence, but not in the absence of exogenous cholesterol.

Example V

This example demonstrates ATR-101 effects on cholesterol accumulation and on the ATP levels of cells that are cultured without serum cholesterol.

Experiments were conducted that examined the effects of ATR-101 on cholesterol accumulation, ATP depletion and caspase activation in H295R cells that were cultured in serum-free medium to determine the influence of serum cholesterol on ATR-101 cytotoxicity. The medium was replaced with serum-free medium with or without ATR-101, and the cells were cultured for 4 h. Cells that were cultured in with ATR-101 in serum-free medium had higher cholesterol levels than cells that were cultured in serum-free medium lacking ATR-101 (FIG. 3A). ATR-101 caused ATP depletion and caspases activation with the same potency in cells that were cultured in serum-free medium (FIG. 6B). MβCD suppressed ATP depletion and caspase activation by ATR-101 in serum-free medium. Cholesterol accumulation was therefore required for ATP depletion and for caspase activation by ATR-101 also in cells that were cultured in serum-free medium. Excess cellular cholesterol can therefore mediate ATR-101 cytotoxicity even when the cells are cultured with ATR-101 in the absence of serum cholesterol.

Example VI

This example demonstrates ATR-101 effects on cholesterol efflux.

To identify potential causes of cholesterol accumulation in cells that were cultured with ATR-101, experiments were conducted that measured the rates of cholesterol efflux from H295R cells in the presence and in the absence of ATR-101. H295R cells produced a linear increase in the total cholesterol concentration of the culture medium over 4 hours (FIG. 6C). ATR-101 inhibited cholesterol efflux, and there was no detectable increase in the cholesterol concentration of the medium of cells that were cultured with ATR-101 (FIG. 6C). The concentration of ATR-101 that inhibited cholesterol efflux was similar to the concentrations that caused cholesterol accumulation, ATP depletion, and caspase activation (FIG. 6D). In contrast, PD129337 had no detectable effect on cholesterol efflux. The concurrent decrease in total soluble cholesterol that was exported to the culture medium and the increase in cell-associated cholesterol indicate that ATR-101 redirected cholesterol discharge from cells. ATR-101 inhibited cholesterol efflux to soluble lipoprotein particles, which requires active export by ABC transporters, and caused an increase in passive extrusion of crystalline and cell-associated cholesterol (FIGS. 6D, 3F).

Experiments were conducted that compared the effect of ATR-101 on cholesterol efflux with the effects of known ABC transporter inhibitors. Glibenclamide blocked cholesterol efflux in H295R cells at a concentration that inhibits ABCA1 (50 µM; FIG. 3D) (see, e.g., Nieland T J, et al., J Lipid Res 2004; 45(7):1256-65). Benzamil did not reduce cholesterol efflux from H295R cells at concentrations that inhibit ABCG1 and that caused cholesterol accumulation in H295R cells (50 µM; FIG. 6D, 7C) (see, e.g., Cserepes J, et al., Biochem Biophys Res Commun 2004; 320(3):860-7). Verapamil inhibited cholesterol efflux at a concentration that inhibits MDR1 and that caused doxorubicin accumulation in H295R cells (50 µM; FIGS. 6D, 8C) (see, e.g., Bentz J, et al., Drug Metab Dispos 2013; 41(7):1347-66). Verapamil and benzamil inhibited cholesterol efflux and caused ATP depletion separately at concentrations that were 10 to 100 fold higher than the concentrations that are required to inhibit MDR1 and ABCG1, respectively.

Experiments were conducted that compared the effects of individual ABC transporter inhibitors on cholesterol accumulation and on the ATP level of H295R cells. Glibenclamide did not cause cholesterol accumulation and did not reduce the ATP level of cells (FIGS. 6D, 9A). Verapamil and benzamil caused cholesterol accumulation, but did not reduce the ATP levels of H295R cells at the concentrations that inhibit ABCG1 and MDR1 activity, respectively (FIGS. 9A, 7C, 6D, 8C) (see, e.g., Cserepes J, et al., Biochem Biophys Res Commun 2004; 320(3):860-7; Bentz J, et al., Drug Metab Dispos 2013; 41(7):1347-66). The inhibition of cholesterol efflux was neither sufficient nor necessary to cause cholesterol accumulation, and cholesterol accumulation was not sufficient to cause ATP depletion in ACC-derived cells.

Experiments were conducted that tested if the inhibition of cholesterol efflux required ATP depletion. Olesoxime reduced ATP depletion by ATR-101, but it had no detectable effect on the inhibition of cholesterol efflux from the same cells, indicating that the restoration of a nearly normal ATP level did not restore any detectable cholesterol efflux (FIG. 6E). Glucose and α-tocopherol also restored the ATP level, and did not restore cholesterol efflux (FIG. 9C).

Example VII

This example demonstrates ATR-101 effects on cortisol secretion and on doxorubicin clearance.

Experiments were conducted that tested the effect of ATR-101 on cortisol secretion to determine the effect of ATR-101 on ABC transporters that export cholesterol metabolites. H295R cells produced a linear increase in the cortisol concentration of the medium over 8 hours (FIG. 5A). ATR-101 inhibited cortisol secretion at the earliest time when cortisol secretion was detected 4 h after ATR-101 addition to the cells. ATR-101 blocked both basal and forskolin-stimulated cortisol secretion as efficiently as the MDR1 inhibitor verapamil (FIGS. 5A, 8A). The same concentration of ATR-101 inhibited cortisol secretion as was required to cause cholesterol accumulation, caspase activation and ATP depletion in H295R cells (FIG. 5B). PD129337 did not reduce, but rather increased, cortisol secretion at concentrations that were up to 5-fold higher than the concentration of ATR-101 that inhibited cortisol export. ACAT inhibition was not sufficient to inhibit cortisol secretion. ATR-101 therefore inhibited cortisol secretion by mechanisms that required specific functional groups that are not present in PD129337.

Experiments were conducted that investigated if the inhibition of cortisol secretion ATR-101 required ATP depletion. Exogenous cholesterol as well as α-tocopherol restored normal or nearly normal ATP levels, but neither compound prevented the inhibition of cortisol secretion by ATR-101 in the same cells (FIG. 5C).

To determine if ATR-101 inhibits MDR1 activity using an independent assay, experiments were conducted that measured the accumulation of doxorubicin in H295R cells that were cultured in medium containing doxorubicin with or without ATR-101. The level of doxorubicin fluorescence was 5-fold higher in H295R cells that were cultured with doxorubicin in the presence of ATR-101 for 2 h (FIG. 5D). ATR-101 caused doxorubicin accumulation in the presence of MβCD, indicating that ATR-101 inhibited doxorubicin clearance independently of cholesterol accumulation or ATP depletion.

Example VIII

This example demonstrates cytotoxicity and cholesterol accumulation by combinations of ABC transporter inhibitors.

Since ATR-101 inhibited both cholesterol, cortisol and doxorubicin export, and since the inhibition of individual ABC transporters did not cause ATP depletion, experiments were conducted that hypothesized that the simultaneous inhibition of several ABC transporters was required ATR-101 cytotoxicity. Experiments were conducted that tested the effects of different combinations of ABC transporter inhibitors on the ATP levels and the caspase 3/7 activities of H295R cells. Glibenclamide, benzamil and zosuquidar in combination reduced the ATP level and increased the caspase 3/7 activity of the cells (FIG. 10A). When any one of the ABC transporter inhibitors was omitted, no decrease in the ATP level was detected, and the caspase 3/7 activity was reduced. Similarly, glibenclamide, benzamil and verapamil in combination caused ATP depletion in H295R cells, but the pairwise combinations had only a partial effect (FIG. 7A). Thus, the simultaneous inhibition of ABCA1, ABCG1, MDR1, and potentially other targets of verapamil, zosuquidar, benzamil and glibenclamide, was required to mimic the effects of ATR-101 on the ATP level and on the caspase 3/7 activity of H295R cells.

Glibenclamide, benzamil, and zosuquidar increased the cholesterol level of H295R cells (FIG. 10B). PD129337 further increased the cholesterol level together with these ABC inhibitors, but it did not enhance ATP depletion or caspase 3/7 activation (FIG. 10A). MβCD reduced the cholesterol level and suppressed the effects on the ATP level and on the caspase 3/7 activity (FIGS. 10A, 10B). Several other combinations of ABC transporter inhibitors and PD129337 increased the cholesterol level, but had little or no effect on the ATP level or on the caspase 3/7 activity (FIGS. 10A, 10B). Cholesterol accumulation was necessary for ATP depletion and for caspase activation by these ABC inhibitors, but it was not sufficient for cytotoxicity. It is possible that the accumulation of other steroids or cholesterol metabolites requires all three ABC transporter inhibitors, and is necessary for their cytotoxicity.

Example IX

This example demonstrates cytotoxicity of ATR-101 in combination with ABC transporter inhibitors and substrate.

Experiments were conducted that investigated if the potency of ATR-101 was enhanced when it was applied in combination with compounds that targeted individual ABC transporters. Experiments were conducted that tested ATR-101 in combination with individual ABC transporter inhibitors and substrates at concentrations that were not cytotoxic when tested separately. ATR-101 in combination with glibenclamide did not increase the efficiency of ATP depletion (FIGS. 10C, 7B). In contrast, ATR-101 in combination with each of benzamil, cyclosporin A, verapamil and rhodamine 123 caused ATP depletion at concentrations that did not deplete ATP individually (FIGS. 10C, 7B). ATR-101 and the MDR1 substrate rhodamine-123 in combination reduced the ATP level of H295R cells at concentrations that were 10-fold and 5-fold lower than the ATR-101 and rhodamine-123 concentrations that were required to reduce the ATP level separately (FIGS. 10C, 7B). MβCD suppressed ATP depletion by ATR-101 in combination with these ABC transporter inhibitors and substrates, suggesting that ATP depletion by these combinations of inhibitors required cholesterol accumulation (FIG. 7B). The potency of ATR-101 can therefore be enhanced by combining it with individual ABC inhibitors or substrates.

Example X

This example demonstrates the roles of steroids and steroidogenesis in ATR-101 cytotoxicity.

ATR-101 inhibition of MDR1 is predicted to cause the accumulation of steroids and other products of cholesterol metabolism. Experiments were conducted that examined the effects of several structurally dissimilar inhibitors of steroidogenic enzymes on ATP depletion by ATR-101. Most of these inhibitors reduced ATP depletion by ATR-101, suggesting that steroid accumulation contributed to ATR-101 cytotoxicity (FIG. 11A). The concentrations of the inhibitors that reduced ATP depletion by ATR-101 were consistent with their inhibitory coefficients for specific steroidogenic enzymes (see, e.g., Garrido, et al., 2014 J Steroid Biochem Mol Biol, 143, 1-10; Johansson, et al., 1998 Pharmacol Toxicol, 83, 225-30; Takahashi, et al., 1990 J Steroid Biochem Mol Biol, 37, 231-6). The reduction of ATP depletion by many different inhibitors of steroidogenesis is consistent with the hypothesis that steroid accumulation contributes to ATR-101 cytotoxicity.

To investigate potential mechanisms whereby steroid accumulation could contribute to ATR-101 cytotoxicity, experiments were conducted that tested the effects of ATR-101 in combination with 3β-(2-diethylaminoethoxy)-5-androsten-17-one (U18666A). ATR-101 and U18666A in combination caused a greater than additive increase in cholesterol accumulation (FIG. 11B). ATR-101 and U18666A in combination also caused ATP depletion at concentrations that had no detectable effect on the ATP level separately (FIG. 11C). MβCD suppressed ATP depletion by ATR-101 in combination with U18666A, suggesting that their combined effect on the ATP level required cholesterol accumulation (FIG. 11D). U18666A as well as endogenous steroids can inhibit cholesterol trafficking, suggesting that steroid accumulation could contribute to ATR-101 cytotoxicity by inhibiting cholesterol trafficking.

Example XI

This example demonstrates the effects of ATR-101 on ABC transporter and steroidogenic gene transcription.

Experiments were conducted that investigated the effects of ATR-101 on transcription of genes whose products modulate cholesterol levels and steroidogenesis. ATR-101 reduced the levels of ABCA1, ABCG1 and IDOL transcripts within an hour after addition to H295R cells (FIG. 12A). Transcription of these genes was repressed by lower ATR-101 concentrations than were required for the cytotoxic effects of ATR-101 or for the activation of CHOP transcription, indicating that their repression was not due to general cell stress. Similar changes in transcript levels were observed 4 and 8 hour after ATR-101 addition. The levels of several steroid biosynthetic gene transcripts, including SULT2A1, HSD3B2 and CYP17A1 were reduced in cells cultured with ATR-101 (FIG. 12B).

PD129337 and ATR-101 had equivalent effects on the levels ABCA1 as well as ABCG1 transcripts (FIG. 13A). They repressed transcription of these genes by mechanisms that were distinct from the selective inhibition of cholesterol and cortisol export by ATR-101. The transcription of ABCA1, ABCG1 and IDOL genes is activated by liver X receptor complexes in response to hydroxysterol binding (see, e.g., Wollam J, Annu Rev Biochem 2011; 80:885-916). Molecular dynamics simulations predicted that ATR-101 and PD129337 can bind to the ligand binding pocket of liver X receptor a (FIG. 13B). ATR-101 and PD129337 binding to liver X receptor a could displace hydroxysterol ligands in a manner similar to that which has been described for unsaturated fatty acids (see, e.g., Ou J, et al., Proc Natl Acad Sci USA 2001; 98(11):6027-32).

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of treating or ameliorating adrenocortical cancer comprising co-administering to said patient a therapeutically effective amount of two or more agents selected from
   1) an agent capable of inhibiting cholesterol efflux related to ABCA1 and/or ABCG1;
   2) an agent capable of inhibiting MDR1 related cortisol secretion and/or MDR1 P-glycoprotein multiple drug transporter activity; and
   3) an agent capable of inhibiting mitochondrial activity, and further comprising administering to said patient one or more anticancer agents, wherein said anticancer agent is a chemotherapeutic agent and/or radiation therapy.

2. The method of claim 1,
wherein the agent capable of inhibiting cholesterol efflux related to ABCA1 and/or ABCG1 is selected from Valspodar, Glyburide, Cyclosporine A,
wherein the agent capable of inhibiting MDR1 related cortisol secretion and/or MDR1 P-glycoprotein multiple drug transporter activity is selected from Tariquidar, MK-571, Niguldipine hydrochloride, Matairesinol, Reversin 121 ($C_{34}H_{47}N_3O_9$), Elacridar, Pyrimethamine ($C_{12}H_{13}ClN_4$), Pyrimethamine Biotin ($C_{27}H_{39}N_7O_3S$), Pyrimethamine-d3 ($C_{12}H_{10}D_3ClN_4$), 8-isopentenylnaringenin, JS-2190 (Boc-Glu(OBzl)-N,N'-dicyclohexylurea, $C_{30}H_{45}N_3O_6$), P-Glycoprotein Inhibitor C-4 ($C_{23}H_{18}ClNO_4$), PGP-4008, Sipholenol A, Reversan, CP 100356 hydrochloride, PSC 833, Zosuquidar trihydrochloride, and Vismodegib,
wherein the agent capable of inhibiting mitochondrial activity is selected from rhodamine-123, MKT-077, decoquinate, isoniazid, suramin, erythrosine, toltrazuril, enilconazole, and metformin.

3. The method of claim 1, wherein said patient is a human patient.

* * * * *

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
acaatcctgc agtgcttcct                                                   20

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
ggcaggtaca gcgtgaagta g                                                 21

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
tgcttccaca ctgttgtcct                                                   20

<210> SEQ ID NO 4
<211> LENGTH: 20
<212> TYPE: DNA
<213> ORGANISM: Artificial Sequence
<220> FEATURE:
```

<223> OTHER INFORMATION: Synthetic

<400> SEQUENCE: 4
cttgaccatt tcccttctgc                                               20

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
cgaggactgc ctcaacca                                                 18

<210> SEQ ID NO 6
<211> LENGTH: 24
<212> TYPE: DNA
<213> ORGANISM: Artificial Sequence
<220> FEATURE:
<223> OTHER INFORMATION: Synthetic

<400> SEQUENCE: 6
tgcagtccaa aatagtcaac ttct                                          24

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
catgggctat ctcaagccac                                               20

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
gagatcttcc tggtgtggga tc                                            22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
gcatcataga caacctgagc aa                                            22

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
gggttttgtt ggggaaaatc                                               20

```
<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
aagctgatct gcctgtagct g                                              21

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tggtgtgagg gtttcaactg                                                20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ccagtagcat agaggtagcc                                                20

<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
tcagattcca cccgttagc                                                 19

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
ttgtggacat gattcccttt c                                              21

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
ctgcttctcc tcgttgtggt                                                20

<210> SEQ ID NO 17
<211> LENGTH: 25
<212> TYPE: DNA
<213> ORGANISM: Artificial Sequence
<220> FEATURE:
<223> OTHER INFORMATION: Synthetic
```

```
<400> SEQUENCE: 17
tgttcaagaa ggaagtgtat cttca                                            25

<210> SEQ ID NO 18
<211> LENGTH: 24
<212> TYPE: DNA
<213> ORGANISM: Artificial Sequence
<220> FEATURE:
<223> OTHER INFORMATION: Synthetic

<400> SEQUENCE: 18
tgatgcctgt ttttgtaggt aaag                                             24
```